US008017386B2

(12) United States Patent
Howe et al.

(10) Patent No.: US 8,017,386 B2
(45) Date of Patent: *Sep. 13, 2011

(54) DIVINYL ETHER SYNTHASE GENE AND PROTEIN, AND USES THEREOF

(75) Inventors: Gregg A. Howe, East Lansing, MI (US); Aya Itoh, Tsuruoka (JP)

(73) Assignee: Board of Trustees of Michigan State University, East Lansing, MI (US)

( * ) Notice: Subject to any disclaimer, the term of this patent is extended or adjusted under 35 U.S.C. 154(b) by 1279 days.

This patent is subject to a terminal disclaimer.

(21) Appl. No.: 11/644,264

(22) Filed: Dec. 22, 2006

(65) Prior Publication Data

US 2010/0075397 A1     Mar. 25, 2010

Related U.S. Application Data

(63) Continuation of application No. 10/381,870, filed as application No. PCT/US01/31296 on Oct. 5, 2001, now Pat. No. 7,154,022.

(60) Provisional application No. 60/238,415, filed on Oct. 6, 2000.

(51) Int. Cl.
*C12N 15/00* (2006.01)
*C07H 21/04* (2006.01)

(52) U.S. Cl. ............... 435/320.1; 536/23.1; 536/23.2; 536/23.6

(58) Field of Classification Search .................. None
See application file for complete search history.

(56) References Cited

U.S. PATENT DOCUMENTS 7,154,022 B2 * 12/2006 Howe et al. .................. 800/281

OTHER PUBLICATIONS

Itoh and Howe, The Journal of Biological Chemistry, 201, vol. 276, No. 5, pp. 3620-3627.*

* cited by examiner

*Primary Examiner* — Eileen B O'Hara
(74) *Attorney, Agent, or Firm* — Medlen & Carroll, LLP

(57) ABSTRACT

The present invention relates to divinyl ether synthase genes, proteins, and methods of their use. The present invention encompasses both native and recombinant wild-type forms of the synthase, as well as mutants and variant forms, some of which possess altered characteristics relative to the wild-type synthase. The present invention also relates to methods of using divinyl ether synthase genes and proteins, including in their expression in transgenic organisms and in the production of divinyl ether fatty acids, and to methods of suing divinyl ether fatty acids, including in the protection of plants from pathogens.

12 Claims, 8 Drawing Sheets

```
ACATCACCTACAATGTTAATAAAACTCACTAAACCAAAATAACAACACCAAAACTTGTTA  -   60
AGAAAAATGTCTTCTTATTCAGAGCTATCAAATCTTCCGATTCGTGAAATTCCAGGGGAC  -  120
           M  S  S  Y  S  E  L  S  N  L  P  I  R  E  I  P  G  D     18
TATGGTTTCCCTATAATTAGCGCGATTAAAGATCGATACGATTATTTCTATAACCAAGGT  -  180
 Y  G  F  P  I  I  S  A  I  K  D  R  Y  D  Y  F  Y  N  Q  G       38
GAAGATGCTTGGTTCCATAACAAAGCTGAAAAATACAAATCTACTGTTGTCAAAATCAAC  -  240
 E  D  A  W  F  H  N  K  A  E  K  Y  K  S  T  V  V  K  I  N       58
ATGGCACCAGGTCCATTCACATCTAATGACTACAAATTGGTAGCCTTTTTAGATGCCAAT  -  300
 M  A  P  G  P  F  T  S  N  D  Y  K  L  V  A  F  L  D  A  N       78
AGCTTTGTTTGCATGTTTGATAATTCCCTCATTGATAAAACTGACACTCTTGGTGGTACA  -  360
 S  F  V  C  M  F  D  N  S  L  I  D  K  T  D  T  L  G  G  T       98
TTTAAGCCTGGTAAAGAATACTACGGTGGTTATCGTCCCGTCGCGTTTATCGATACCAAA  -  420
 F  K  P  G  K  E  Y  Y  G  G  Y  R  P  V  A  F  I  D  T  K      118
GATCCAAACCACGCAGCATTAAAAGGCTACATTTTATCATCATTCGCAAAGCGACATAAC  -  480
 D  P  N  H  A  A  L  K  G  Y  I  L  S  S  F  A  K  R  H  N      138
TTATTCATTCCTCTGTTCAGAAACACGTTATCCGATCATCTTTTTAATAATCTCGAAAAA  -  540
 L  F  I  P  L  F  R  N  T  L  S  D  H  L  F  N  N  L  E  K      158
CAGGTTACTGAACAGGGGAAAGCAGATTTCAATGCTTTGCTTCCGACTATGACGTTTGAT  -  600
 Q  V  T  E  Q  G  K  A  D  F  N  A  L  L  P  T  M  T  F  D      178
TTCATTTTTCGTTTGCTTTGTGATCAGAAAAATCCGTCTGATACAGTTCTTGGCGCTCAA  -  660
 F  I  F  R  L  L  C  D  Q  K  N  P  S  D  T  V  L  G  A  Q      198
GGACCAGAACATCTACGTAAATGGCTTTTCCCACAGCTAATTCCGTCCTTGAGCGCCAAG  -  720
 G  P  E  H  L  R  K  W  L  F  P  Q  L  I  P  S  L  S  A  K      218
AAACTTCCTAACATCATAGAAGATATGCTCTTCCATAATTTTTTAATACCATTTGGTTTT  -  780
 K  L  P  N  I  I  E  D  M  L  F  H  N  F  L  I  P  F  G  F      238
ATAAAGAGTGATTACAACAAACTTGTTGATGCATTTAGCAAGTCTGCTGTGTCCATGTTG  -  840
 I  K  S  D  Y  N  K  L  V  D  A  F  S  K  S  A  V  S  M  L      258
GATGAAGCAGAAAAACTTGGAATCAAAAGAGAAGAAGCTGTACAAAACATTCTTTTTCTC  -  900
 D  E  A  E  K  L  G  I  K  R  E  E  A  V  Q  N  I  L  F  L      278
GTGGGGATCAATATGTTTGCGGGGCTGAACGCCTTTTTCCCTCATCTATTCAGGTTTGTG  -  960
 V  G  I  N  M  F  A  G  L  N  A  F  F  P  H  L  F  R  F  V      298
GGCGAAGCAGGGGCTAGTCTACACACACAACTTGCTAAAGAAATCAGGAGTGTTATTAAA  - 1020
 G  E  A  G  A  S  L  H  T  Q  L  A  K  E  I  R  S  V  I  K      318
GAAGAAGGTGGTGCAATCACATTATCAGCGATTAACAAAATGAGTTTGGTCAAATCGGTA  - 1080
 E  E  G  G  A  I  T  L  S  A  I  N  K  M  S  L  V  K  S  V      338
GTGTACGAGACATTGAGACTTCGCCCACCAGTACCATTACAGTATGGTAAGGCGAAGAAA  - 1140
 V  Y  E  T  L  R  L  R  P  P  V  P  L  Q  Y  G  K  A  K  K      358
GAGTTCATGGTTCAAAGCCACGATGCATCTTACAAGATCAATAAAGGACAATTCGTAGTT  - 1200
 E  F  M  V  Q  S  H  D  A  S  Y  K  I  N  K  G  Q  F  V  V      378
GGATATCAGCCCATGGCTAGTAGGGACCCTAAGATTTTCGCAAACCCGGATGAGTTTGTA  - 1260
 G  Y  Q  P  M  A  S  R  D  P  K  I  F  A  N  P  D  E  F  V      398
CCTGATAGGTTCATGAATGATGGTGAGAAAATGCTGAAACATGTCCTATGGTCTAATGGA  - 1320
 P  D  R  F  M  N  D  G  E  K  M  L  K  H  V  L  W  S  N  G      418
AGGGAAACAGAGAGTCCAGCACCAGATAACAAGCAATGTCCAGGCAAAGATTTGGTGCAC  - 1380
 R  E  T  E  S  P  A  P  D  N  K  Q  C  P  G  K  D  L  V  H      438
CTATTGGGTAGGTTAATATTGGTTGAATTTTTCATCAGATACGATACATTCACCCTGGAA  - 1440
 L  L  G  R  L  I  L  V  E  F  F  I  R  Y  D  T  F  T  L  E      458
ATTACACCTCTATTTCGTGCACCAAATGTTGCGTTCAACACATTAACTAAAGCAAGTAAA  - 1500
 I  T  P  L  F  R  A  P  N  V  A  F  N  T  L  T  K  A  S  K      478
TAGTTTGTTATGTGATCAAACTGTGTGTGCCCGCTCACGTTGCATATTCTCTTATTGATT  - 1560
ATTTTATTTTTTTGGTTGTATTTATTTAGTTTTTGTTGTAAATCTTCTTTATGATTCAAA  - 1620
TGAATAAACGTTGATTCTAGATCGGATCAAAAAAAAAAAAAAAAAAAAAAAAAAAAAAA   - 1679
```

Figure 2

| | | |
|---|---|---|
| CYP74D1 | 1 | ------------------------------------------------------------- |
| LeAOS1 | 1 | ---MASTSLSLPSLKLQFPPSHTSSSSRKNSSSYRVSIRPIQASVSEIPPYISSPSQSPSS |
| LeAOS2 | 1 | MALTLSFSLPLPSLHQKIPSKYS-----------TFRPIIVSLSDK------------- |
| LeHPL | 1 | -----------------------------------------------------MNS |

| | | |
|---|---|---|
| CYP74D1 | 1 | -MSSYSELSNLPIREIPGDYGFPKISAIKDRYDYFYNQGEDAWFHNKAEKYKSTVVKINM |
| LeAOS1 | 58 | SSSPPVKQAKLPAQKVPGDYKLPLVGPWKDRLDYFYNQGKNEFFKSRHQKHQSTVFRTNM |
| LeAOS2 | 36 | STIEITQPIKLSTRTIPGDYGLPGTGPWKDRLDYFYNQGKNDFFESRIAKYKSTFFRTNM |
| LeHPL | 4 | APLSTPAPVTLPVRSIPGSYGLPEVGPIADRLDYFNFQKPENFFTKRLEKHKSTVFRTNV |

| | | |
|---|---|---|
| CYP74D1 | 60 | APGP--FTSNDYKLVAFLDRNSFVCMFDNSLIDKTDTLGGTFKPGKRYYGGYRPVAEIDT |
| LeAOS1 | 118 | PPGP--FISFNPNVVVLLDGKSFPVLFDVSKVEKKDEFTGTFMPSTILTGGYRVLSYLDP |
| LeAOS2 | 96 | PPGP--FITSNPKVIVLLDGKSFPVLFDASKVEKKDEFTGTFVPSTELTGGYRTISYLDP |
| LeHPL | 64 | PPCFPFFGSVNPNVVAYLDVKSESHLFDMEIVEKANVLVGDEMPSVVYTGDMRVCAYLDT |

| | | |
|---|---|---|
| CYP74D1 | 118 | KDPNHAALKGYILSSFAKRENLFIPLPENTLSDHLFNNLEKQVEBQGKADFNALLPTMTF |
| LeAOS1 | 176 | SEPNHAKLKKLMPYLLSSRKNEVIPEGHNSYS-ELFETLENEFSTKGKAGLNAANDQAAV |
| LeAOS2 | 154 | SEPNHBKLKKLMPFLLSSRRDHVIPEGHETYT-ELFETLDKKEMBEKGTVGFNSGSDQAAF |
| LeHPL | 124 | SEPKHAQIKNFSQDILKRGSKTWYIPTLLKELD-TMFTTFEADDGKSNTASLLPALQKFLE |

| | | |
|---|---|---|
| CYP74D1 | 178 | DFIFRLLCDQKNFSDTVLGAQGFEHIRKWIFPQLIPSISAAKKLPNITEDMLFHNFLIPFG |
| LeAOS1 | 235 | NFDARSLYG-INPQDTELGTDGFKLJGKWVLFQLHPLHIEG-LPKVLEDIVHTFRTPPA |
| LeAOS2 | 213 | NFDARSLFG-VNPVEBKLGTDGFALIGKWILLQHPVSIG-LPKFLDDVILETFRDPPI |
| LeHPL | 183 | NFFSLITLGADSSVSPEIANSGYIFDSWEAIQLAPTVSLG-VLQPLEETLVHSRAYPPF |

| | | |
|---|---|---|
| CYP74D1 | 238 | FIKSDYNKLVDAFSKSAVSMLDEAEKLG-IKREEAVQNELFLVGINMFAGLNAFPPHIPR |
| LeAOS1 | 293 | LVKKDYQRLYNEFYENSTSYLDEAEKIG-IERREACHNLLFATCFNSFGGIKIFFPNMLK |
| LeAOS2 | 271 | LVKKDYQRLYDFFYTNSANDFIEAEKLG-ISKDEACHNLLFATCFNSFGGMKIFFPNLLK |
| LeHPL | 242 | LVKGNYEKLVQBFVKNBAKEVLSRAQTBFQTNEQELIHNLLFILGFNAFGGFSIFLPTLLG |

| | | |
|---|---|---|
| CYP74D1 | 297 | FVG-EAGASIHTQLAKEIRSVIKEEGGAITLSAINKMSLVKSVVYETLRERPPVPLQYGK |
| LeAOS1 | 352 | WIG-RAGAKLESQLAQEIRSVISSNSGKYTMAAHEKPPLEKSVVYETLRIEPPVASQYGK |
| LeAOS2 | 330 | STA-KAGVETHIRLANEIRSEVKSAGGKITMSAMEKMPLMKSVVYEALRVDPPVASQYGR |
| LeHPL | 302 | NDLGDEKNADMQEKLRKEVRDKYGVNPENDSFEEWKEMELVQSFVYETLRLSPPVPSQYAR |

| | | |
|---|---|---|
| CYP74D1 | 356 | AKEEFMVQSHDASFKINKGQFVVGYQPMASRDPKIFANPDEFVPDRFMNE-GEKMLKHVL |
| LeAOS1 | 411 | AKHDMVDESHDASFEIKEGEELYGYQPFATKDPKIFDRSEEFVADRFKGEEGEKLLKHVL |
| LeAOS2 | 389 | AKQDLKIESHDAVFEVKKGETLFGYQPFATKDPKIFDRPGEFVADRFVGEEGEKLLKHVL |
| LeHPL | 362 | ARKDPKLSSHDSVYEIKKGEDLCGYQPLVMKDPKYFDEPEKFVLERFTKEKGKELLNYTFF |

| | | |
|---|---|---|
| CYP74D1 | 415 | WSNGRETESPAPDNKQCPGKDLVELLGRLIIVEFFERYDIFTLETPLPRAPNVAFNTLT |
| LeAOS1 | 471 | WSNGSETENASINNKQCAGKDFVVLYSRLEEVELFLRYDSFELEVGASPLQAAATETSLR |
| LeAOS2 | 449 | WSNGPETESPTVGNKQCAGKDFVVLYSRLFYTFFFLRYGLLNVDVCTSALGSSLEETSLK |
| LeHPL | 422 | WSNGPQTGRFTESNKQCAAKDMVTLTASLEVAYIEQKYDEVSFSSG--------SLTSVK |

| | | |
|---|---|---|
| CYP74D1 | 475 | KASK |
| LeAOS1 | 531 | RASP |
| LeAOS2 | 509 | KA-- |
| LeHPL | 474 | KAS- |

Figure 3

DIVINYL ETHER SYNTHASE GENE AND PROTEIN, AND USES THEREOF

The present application is a Continuation of U.S. patent application Ser. No. 10/381,870, filed Nov. 17, 2003, now U.S. Pat. No. 7,154,022 issued on Dec. 26, 2006, which is a National Entry of International Patent Application No. PCT/US01/31296, filed Oct. 5, 2001, now abandoned, which claims priority to U.S. Provisional Application Ser. No. 60/238,415, filed on Oct. 6, 2000, now abandoned, each of which are incorporated herein by reference in their entireties.

This invention was made in part during work partially supported by the United States Department of Energy grant no. 61-4224 and United States Department of Agriculture grant no. 61-3200-010. The United States government may have certain rights in the invention.

FIELD OF THE INVENTION

The present invention relates to isolated divinyl ether synthase genes and polypeptides. The present invention also provides methods for using divinyl ether synthase genes, polypeptides, and synthase products.

BACKGROUND OF THE INVENTION

Plant-pest interactions play an important role in shaping both natural and agricultural ecosystems. Crop losses due to pest attack remain a serious problem in the U.S., despite intensified use of chemical pesticides. As an example, late blight (*Phytophthora infestans*) is one of the most important diseases of potato (*Solanum tuberosum* L.) worldwide causing both the destruction of plants in the field and rotting of tubers during storage. Currently, there are no late blight resistant potato cultivars that meet US commercial standards (Douches et al., Amer. Potato J. 74: 75-86 [1997]). Although late blight has been effectively controlled for many years with both protective and systemic fungicides, more aggressive, fungicide resistant genotypes of *P. infestans* now predominate in many parts of North America making control more difficult (Deahl et al., Phytophthora infestans 150. Boole Press Ltd., pp 362 [1995]; Goodwin et al., Phytopathology 85: 473-479 [1995]). In fact, it is estimated that *P. infestans* cost US growers $155 million in 1999 (Sender, Agricultural Genomics 3: 4-6 [2000]). Additional problems associated with the use of chemical pesticides, which include environmental contamination, increase production costs, and threats to human health, have resulted in increasing demand for decreased use of chemical pesticide.

Therefore, an attractive alternative to pesticides, and possible resolution of the environmental and economic problems they pose, is the development of crop protection strategies that maximize the plant's "built-in" defense capabilities, or phytochemical defense mechanisms. One set of such defense mechanisms, as revealed by recent evidence, is the synthesis of oxylipins (oxygenated fatty acids), which are a critical component of both constitutive and induced mechanisms for plant defense against a broad spectrum of pests (Farmer and Ryan, Proc. Natl Acad. Sci. USA 87: 7713-7718 [1990]; Farmer and Ryan, Plant Cell 4: 29-134 [1992]).

Oxylipin metabolism in plants, although complex in its details, can be viewed as a simple two-step process. The first step involves the addition of molecular oxygen to polyunsaturated fatty acids such as linoleic acid and linolenic acid. This reaction is performed enzymatically by lipoxygenase (LOX). Plant LOXs catalyze the stereospecific addition of $O_2$ to either the 9 or the 13 position of $C_{18}$ fatty acids, thus generating 9- or 13-fatty acid hydroperoxides, respectively. Fatty acid hydroperoxides are also generated non-enzymatically by free radical-catalyzed lipid peroxidation; this route of hydroperoxide formation is likely to be an important part of the hypersensitive response of plants to avirulent pathogens.

The second phase of oxylipin metabolism involves the metabolism of fatty acid hydroperoxide intermediates to different classes of bioactive oxylipins. Four major sub-branches of fatty acid hydroperoxide metabolism have been described, all of which convert 13-hydroperoxy linolenic (and in some cases other hydroperoxides) to defense-related compounds. Of these four branches, the most well known is the synthesis of jasmonic acid and related cyclopenta(e)ones. Much less is known about another branch, which is the synthesis of divinyl ether fatty acids.

SUMMARY OF THE INVENTION

Therefore, it would be desirable to be able to generate large quantities of divinyl ether fatty acids, which could be exogenously applied to plants to protect them against pathogens. Alternatively, it would be desirable to effect protection by generating increased amounts of endogenous divinyl ether fatty acids in plants.

The present invention relates to compositions comprising divinyl ether synthase ("DES") genes and polypeptides. The present invention is not limited to any particular nucleic acid or amino acid sequence. The present invention also provides methods for using DES genes, polypeptides, and synthase products.

Accordingly, in some embodiments, the present invention provides compositions comprising an isolated nucleic acid sequence encoding a DES or portions thereof; preferably, the nucleic acid sequence encodes a tomato DES or a portion thereof; more preferably, the tomato is *Lycopersicon esculentum*, and most preferably, the isolated nucleic acid sequence comprises SEQ ID NO: 1. The present invention is not limited to nucleic acid sequences encoding DES; indeed, it is contemplated that the present invention encompasses nucleic acid sequences encoding homologs, variants, and portions or fragments of DES. Accordingly, in some embodiments, the present invention provides isolated nucleic acid sequences that hybridize under conditions of low to high stringency to a nucleic sequence comprising SEQ ID NO: 1; in some preferred embodiments, a hybridizing sequence encodes a polypeptide that catalyzes the conversion of hydroperoxide fatty acids to divinyl ether fatty acids that contain an oxygen within the hydrocarbon chain. In other embodiments, the present invention provides isolated nucleic acid sequences encoding a DES, wherein the synthase competes for binding to a dihydroperoxide fatty acid substrate with a protein encoded by a nucleic acid sequence comprising SEQ ID NO: 1. In yet other embodiments, the present invention provides isolated antisense sequences corresponding to a nucleic acid sequence encoding a DES.

In some embodiments of the present invention, the nucleic acid sequences described above are operably linked to a heterologous promoter. In further embodiments, the sequences described above are contained within a vector.

In other embodiments, the invention provides purified polypeptides encoded by any of the nucleic acid sequences described above. In other embodiments, the present invention provides a purified DES or portions thereof. In some preferred embodiments, DES is purified from tomato; in other preferred embodiments, the DES is purified from *Lycopersicon esculentum*.

In other embodiments of the present invention, compositions are provided comprising at least one divinyl ether fatty acid and a carrier suitable for applying the fatty acid to a plant, a plant part, or a plant seed. In some preferred embodiments, the divinyl ether fatty acid is a product of DES when incubated with at least one hydroperoxide fatty acid substrate selected from the group consisting of mono-, di-, and tri-hydroxy fatty acids with variable chain length and from none to one or more additional functional group selected from the group consisting of acetylenic bonds, conjugated acetylenic and ethylenic bonds, allenic groups, cyclopropane, cyclopropene, cyclopentene and furan rings, epoxy-, hydroxy- and keto-groups and double bonds of both the cis and trans configuration and separated by more than one methylene group, wherein the substrates are either free fatty acids, or fatty acids incorporated into a larger molecule; in particularly preferred embodiments, the divinyl ether fatty acids are selected from the group consisting of colneleic acid and colnelenic acid. In other preferred embodiments, the compositions further comprise components which aid plant growth and protection; such components include but are not limited to fertilizer, insecticide, fungicide, nematocide, and herbicide. In yet other preferred embodiments, compositions further comprise components which facilitate application of the composition to the plant, the plant part or the plant seed; such components include but are not limited to buffering agents, wetting agents, coating agents, and abrading agents. In yet other preferred embodiments, compositions further comprise components which aid seed storage and germination; such components include but are not limited to clays and polysaccharides.

In further embodiments, the present invention provides organisms transformed with any of the nucleic acid sequences described above. In other embodiments, the present invention provides organisms transformed with a heterologous gene encoding a DES or a portion thereof; in some preferred embodiments, the gene is a tomato gene; in other preferred embodiments, the gene is a *Lycopersicon esculentum* gene; in other preferred embodiments, the gene comprises SEQ ID NO: 1.

In other embodiments, the present invention provides organisms co-transformed with a first heterologous gene encoding a DES and with a second heterologous gene encoding a LOX. In yet other embodiments, the present invention provides organisms co-transformed with a heterologous gene encoding a fusion polypeptide comprising a DES and a LOX.

In other embodiments of the present invention, transformed organisms as described above are either plants or a microorganisms. In a preferred embodiment, the organisms are plants. In other embodiments, plant cells are transformed with any of the heterologous genes described above. In yet other embodiments, plant seeds are transformed with any of the heterologous genes described above. In yet other embodiments, the invention provides oils from plants transformed as described above.

In other embodiments, the present provides methods for expressing a synthase in a plant, comprising providing plant tissue and a vector comprising any of the nucleic acid sequences described above which encode a DES, and transfecting the plant tissue with the vector under conditions such that the synthase is expressed. In other embodiments, the present invention provides methods for expressing an antisense sequence in plants, comprising providing plant tissue and a vector comprising an antisense sequence corresponding to any of the nucleic acid sequences described above which encode a DES, and transfecting the plant tissue with the vector under conditions such that the antisense sequence is expressed.

In further embodiments, the invention provides methods for producing a variant of DES; comprising providing a nucleic acid sequence encoding a DES, and mutagenizing the nucleic acid sequence so as to produce a variant; in still other embodiments, the methods further comprise screening the variant for activity.

In other embodiments, the present invention provides methods of producing divinyl ether fatty acids in vitro, comprising providing a purified DES and at least one fatty acid substrate of the enzyme, and incubating the synthase with the substrate under conditions such that divinyl ether fatty acids are produced. In preferred embodiments, the substrate of DES is selected from the group consisting of mono-, di-, and tri-hydroperoxide fatty acids with variable chain length and from none to one or more additional functional group selected from the group consisting of acetylenic bonds, conjugated acetylenic and ethylenic bonds, allenic groups, cyclopropane, cyclopropene, cyclopentene and furan rings, epoxy-, hydroxy- and keto-groups and double bonds of both the cis and trans configuration and separated by more than one methylene group, wherein the substrates are either free fatty acids, or fatty acids incorporated into a larger molecule; in other preferred embodiments, the substrate is selected from the group consisting of 9-hydroperoxystearidonic acid, 13-hydroperoxystearidonic acid, 9-hydroperoxylinoleic acid, 9-hydroperoxylinolenic acid, 13-hydroperoxylinoleic acid, 9-hydroperoxylinolenic acid, 13 hydroperoxylinolenic acid, 9-hydroperoxyarachidonic acid, and 13-hydroperoxyarachidonic acid.

In other embodiments, the present invention provides methods of producing divinyl ether fatty acids in vitro, comprising providing an isolated nucleic sequence encoding a DES and at least one fatty acid substrate of the enzyme, and incubating the sequence with the substrate in a transcription/translation system under conditions such that the sequence is expressed and divinyl ether fatty acids are produced. In preferred embodiments, the substrate of DES is selected from the group as described above.

In other embodiments, the invention provides methods of producing divinyl ether fatty acids in vitro, comprising providing a purified DES, a purified LOX and at least one fatty acid substrate of the LOX, and incubating the DES and the LOX with the substrate(s) under conditions such that divinyl ether fatty acids are produced. In preferred embodiments, the fatty acid substrate(s) of LOX is selected from the group consisting of polyunsaturated fatty acids with at least two double bonds in a 1Z,4Z-pentadiene structure and with variable chain length and from none to more than one additional functional group selected from the group consisting of acetylenic bonds, conjugated acetylenic and ethylenic bonds, allenic groups, cyclopropane, cyclopropene, cyclopentene and furan rings, epoxy-, hydroxy- and keto-groups and double bonds of both the cis and trans configuration and separated by more than one methylene group, wherein the substrates are either free fatty acids or fatty acids incorporated into a larger molecule. In particularly preferred embodiments, the substrate(s) is selected from the group consisting of stearidonic acid, linoleic acid, linolenic acid and arachidonic acid.

In further embodiments, the present invention provides methods of producing divinyl ether fatty acids by fermentation, comprising providing a microorganism transformed with a heterologous gene encoding a DES and at least one substrate of the DES, and incubating the microorganism with the substrate under conditions such that divinyl ether fatty acids are produced. In preferred embodiments, the fatty acid substrate of DES is selected from the group as described above.

In other embodiments, the present invention provides methods of producing divinyl ether fatty acids by fermentation, comprising providing a microorganism co-transformed with a first heterologous gene encoding a DES and with a second heterologous gene encoding a LOX and at least one substrate of the LOX, and incubating the microorganism with the substrate under conditions such that divinyl ether fatty acids are produced. In preferred embodiments, the fatty acid substrate of LOX is selected from the group described above.

In further embodiments, the present invention provides methods of producing divinyl ether fatty acids by fermentation, comprising providing a microorganism transformed with a heterologous gene encoding a fusion polypeptide comprising a DES and a LOX and at least one substrate of the LOX, and incubating the microorganism with the substrate under conditions such that divinyl ether fatty acids are produced. In preferred embodiments, the fatty acid substrate of LOX is selected from the group described above.

In other embodiments, the present invention provides methods of producing divinyl ether fatty acids in a plant comprising providing a plant and a heterologous gene encoding a DES, and transforming the plant with the heterologous gene such that divinyl ether fatty acids are produced. In other embodiments, the present invention provides methods of producing divinyl ether fatty acids in a plant comprising growing a plant transformed with a heterologous gene encoding a DES under conditions such that divinyl ether fatty acids are produced. In yet other embodiments, the present invention provides methods of producing divinyl ether fatty acids in a plant comprising providing a plant, a first heterologous gene encoding a DES, and a second heterologous gene encoding a LOX, and co-transforming the plant with the first heterologous gene and with the second heterologous gene such that divinyl ether fatty acids are produced. In other embodiments, the present invention provides methods of producing divinyl ether fatty acids in a plant comprising growing a plant transformed with a first heterologous gene encoding a DES, and with a second heterologous gene encoding a LOX under conditions such that divinyl ether fatty acids are produced. In still other embodiments, the present invention provides methods of producing divinyl ether fatty acids in a plant comprising providing a plant and a heterologous gene encoding a fusion polypeptide comprising a DES and a LOX, and transforming a plant with the heterologous gene, such that divinyl ether fatty acids are produced. In other embodiments, the present invention provides methods of producing divinyl ether fatty acids in a plant comprising growing a plant with a heterologous gene encoding a fusion polypeptide comprising a DES and a LOX under conditions such that divinyl ether fatty acids are produced.

In yet other embodiments, the present invention provides methods of protecting a plant from a pathogen comprising growing a plant transformed with a heterologous gene encoding a DES under conditions such that the plant is protected from the pathogen. In still further embodiments, the present invention provides methods of protecting a plant from a pathogen comprising growing a plant transformed with a first heterologous gene encoding a DES and with a second heterologous gene encoding a LOX under conditions such that the plant is protected from the pathogen. In still other embodiments, the present invention provides methods of protecting a plant from a pathogen comprising growing a plant transformed with a heterologous gene encoding a fusion polypeptide comprising a DES and a LOX under conditions such that the plant is protected from the pathogen. In preferred embodiments, plant is a potato plant, and the pathogen is *Phyotphora infestans*.

In other preferred embodiments, the present invention provides transgenic plants comprising any of the nucleic acid sequences described above, where the nucleic acid sequences are under control of promoters that control expression of the nucleic acid sequence in a target or specific tissue of the plant or in a target or specific developmental phase of the plant, or promoters that are inducible. It is contemplated that such transgenic plants may be used for any of the methods described above for producing divinyl ether fatty acids in plants or for protecting plants from pathogens.

Other embodiments of the present invention provide methods of protecting plants from a pathogen comprising providing a transgenic plant transformed with a heterologous gene encoding a DES, and growing the transgenic plant under conditions effective to protect the plant from the pathogens. Yet other embodiments of the present invention provide methods of protecting plants from a pathogen comprising providing a transgenic seed transformed with a heterologous gene encoding a DES, and growing a transgenic plant from the transgenic seed under conditions effective to protect the plant from the pathogens. Still other embodiments of the present invention provide methods of protecting plants from a pathogen comprising providing a transgenic plant material transformed with a heterologous gene encoding a DES, and growing a transgenic plant from the transgenic plant material under conditions effective to protect the plant from the pathogens.

Further embodiments of the present invention provide methods of protecting plants from pathogens comprising applying a composition comprising at least one divinyl ether fatty acid such that the plant is protected from the pathogen. Preferably, the divinyl ether fatty acid is a product of DES when incubated with hydroperoxide fatty acid substrates selected from the group consisting of mono-, di-, and tri-hydroxy fatty acids fatty acids with variable chain length and from none to one or more additional functional group selected from the group consisting of acetylenic bonds, conjugated acetylenic and ethylenic bonds, allenic groups, cyclopropane, cyclopropene, cyclopentene and furan rings, epoxy-, hydroxy- and keto-groups and double bonds of both the cis and trans configuration and separated by more than one methylene group, wherein the substrates are either free fatty acids, or fatty acids incorporated into a larger molecule; more preferably, the divinyl ether fatty acids is a colneleic acid or colnelenic acid.

In yet other embodiments, the present invention provides methods for screening DESs comprising providing a candidate DES and analyzing said candidate DES for the presence of the motif AGxxAF in the I-helix consensus sequence.

In yet other aspects, the present invention provides a computer readable medium encoding a representation of any of the nucleic acid sequences as described above. In yet other embodiments, the present invention provides a computer readable medium encoding a representation of any of the polypeptides as described above.

In yet other embodiments, the present invention provides a method of catalyzing a reaction, comprising combining a purified divinyl ether synthase and a hydroperoxy substrate under conditions effective to convert the hydroperoxy substrate to a divinyl ether product. In yet other embodiments, the present invention provides a method of catalyzing a reaction, comprising combining a transgenic organism and a hydroperoxy substrate under conditions effective to convert the hydroperoxy substrate to a divinyl ether product, wherein the transgenic organism comprises a heterologous gene encoding a divinyl ether synthase.

DESCRIPTION OF THE FIGURES

FIG. 2 shows the nucleic acid sequence (SEQ ID NO:1) and deduced amino acid sequence (SEQ ID NO:2) of *Lycopersicon esculentum* DES (LeDES).

FIG. 3 shows a comparison of cDNA-deduced protein sequences of CYP74 P450s in tomato. Sequences were aligned using the ClustalW 1.7 program. The CYP74D1 sequence (SEQ ID NO:2) is that predicted from the open reading frame of clone cLEC3817 (EST277670). *Lycopersicon esculentum* allene oxide synthase 1 (LeAOS1 (GenBank™ accession no. AJ271093; SEQ ID NO:3) and *Lycopersicon esculentum* allene oxide synthase 2 (LeAOS2 (GenBank™ accession no. AF23037; SEQ ID NO:4) are members of the CYP74A subfamily, whereas *Lycopersicon esculentum* fatty acid hydroperoxide lyase (LeHPL) (GenBank™ accession no. AF230372; SEQ ID NO:5) belongs to the CYP7B subfamily. Black boxes indicate amino acid residues that are identical between all four CYP74 members. Shaded boxes indicate positions that contain a conserved amino acid substitution. The hexapeptide motif within I-helix region is underlined. The ☐ symbol denotes the position of the conserved threonine found in the I-helix of P450 monooxygenases. The CYP74 consensus sequence surrounding the cysteinyl heme ligand (*) is underlined.

GENERAL DESCRIPTION OF THE INVENTION

Figure 1:
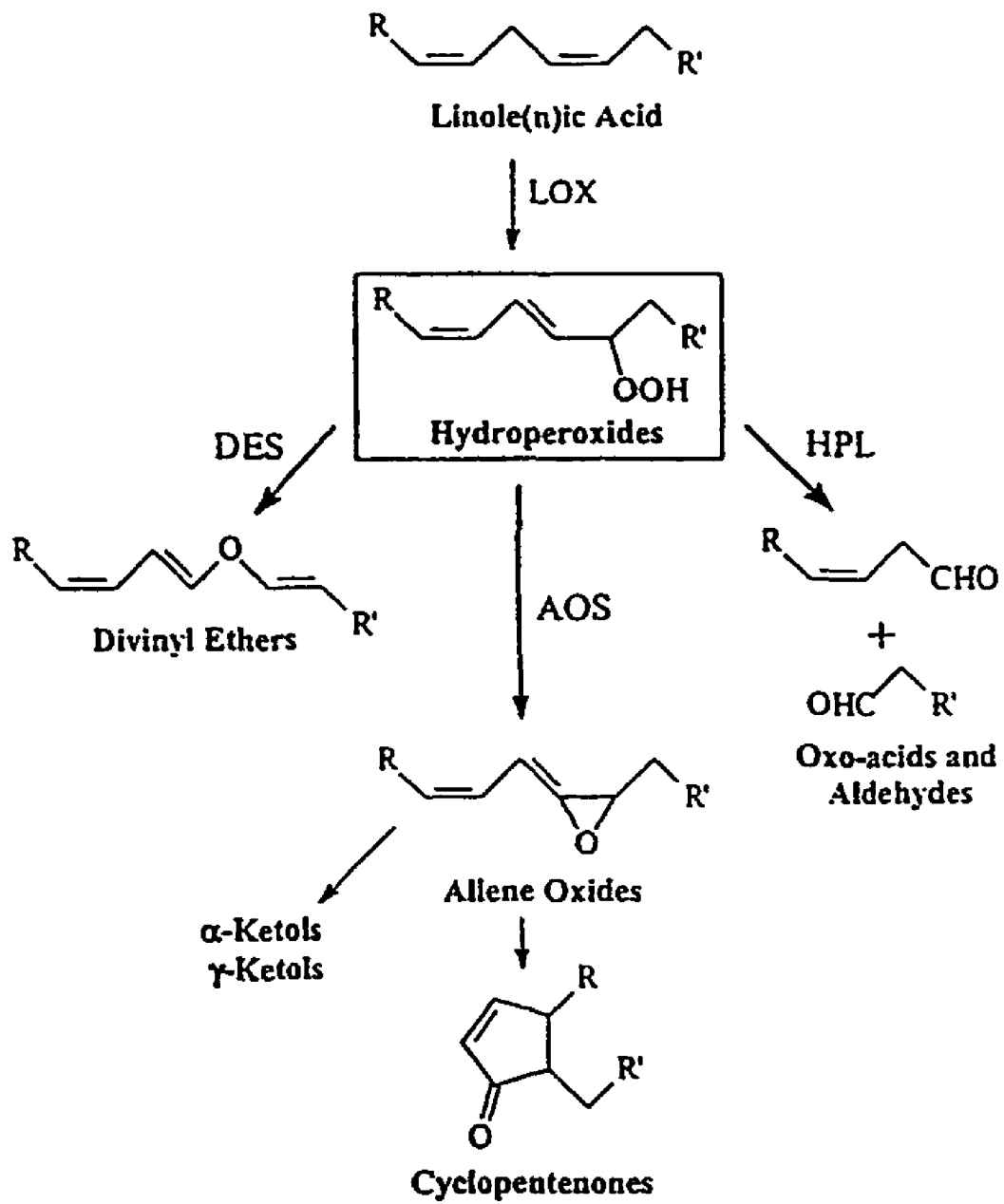
FIG. 1 shows pertinent pathways for oxylipin metabolism. Linolenic and linoleic acids are converted to 9- and 13-hydroperoxides by LOX (R and R' will differ depending on the particular hydroperoxide formed). Hydroperoxide products of LOX are then metabolized by allene oxide synthase, fatty acid hydroperoxide lyase, and DES to various oxylipin intermediates or end products.

The present invention relates to compositions comprising DES genes and polypeptides. The present invention encompasses compositions comprising both native and recombinant forms of the enzyme, as well as mutant and variant forms, some of which possess altered characteristics relative to the wild-type. The present invention also provides methods for using DES genes, polypeptides, and synthase products.

In some embodiments, the present invention provides novel isolated nucleic acid sequences encoding a divinyl ether synthase. In other embodiments, the invention provides isolated nucleic acid sequences encoding mutants, variants, homologs, chimeras, and fusions of divinyl ether synthase. In other embodiments, the present invention provides methods of generating such sequences. In other embodiments, the present invention provides methods of cloning and expressing such sequences, as well as methods of purifying and assaying the expression product of such sequences.

In additional embodiments, the invention provides purified DES polypeptides. In other embodiments, the present invention provides mutants, variants, homologs, chimeras, and fusion proteins of DES. In some embodiments, the present invention provides methods of purifying, and assaying the biochemical activity of wild type as well as mutants, variants, homologs, chimeras, and fusions of divinyl ether synthase polypeptides, as well as methods of generating antibodies to such proteins.

In some embodiments, the present invention provides methods of using novel isolated nucleic acid sequences encoding a divinyl ether synthase to produce products of the synthase activity. In some embodiments, the methods involve adding the sequences to in vitro transcription and translations systems which include the substrates of the synthase, such that the products of the synthase may be recovered. In other embodiments, the methods involve transforming organisms with the sequences such that the sequences are expressed and products of the synthase are produced. In particular embodiments, the products are recovered. In other embodiments, the products remain in situ.

In some embodiments, the present invention provides methods of using recombinant DES polypeptides to produce products of the synthase activity. In some embodiments, the methods involve adding the polypeptides to in vitro systems which include the substrates of the synthase, such that the products of the synthase may be recovered.

In some embodiments, the present invention provides methods of using divinyl ether fatty acids to protect plants against pathogens. In some embodiments, the methods involve applying exogenous divinyl ether fatty acids to a plant to provide protection.

In other embodiments, the methods involve transforming a plant with a novel isolated nucleic acid sequence encoding a divinyl ether synthase such that products of the synthase are produced.

In some embodiments, the present invention provides an organism transformed with heterologous gene encoding a divinyl ether synthase. In some embodiments, the organism is a microorganism. In other embodiments, the organism is a plant.

In some embodiments, the present invention also provides a cell transformed with an heterologous gene encoding a divinyl ether synthase. In some embodiments, the cell is a microorganism. In other embodiments, the cell is a plant cell.

In yet other embodiments, the present invention provides a computer readable medium encoding a representation of any of the nucleic acid sequences described above; preferably, the nucleic acid sequences encode DES or a protein comprising DES. In other embodiments, the present invention provides a computer readable medium encoding a representation of any of the polypeptides described above; preferably, the polypeptides are DES or comprise DES.

DEFINITIONS

To facilitate an understanding of the present invention, a number of terms and phrases are defined below:

As used herein, the term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure or a plant tissue. The term "plant material" as used herein refers to material obtained from a plant or from a plant source, such as plant cell or plant tissue cultures; the material may comprise primarily plant organs or plant tissues, or plant parts.

As used herein, the term "crop" or "crop plant" is used in its broadest sense. The term includes, but is not limited to, any species of plant or algae edible by humans or used as a feed for animals or used, or consumed by humans, or any plant or algae used in industry or commerce.

As used herein, "oil-producing species" refers to plant species which produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

As used herein, the term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

As used herein, the term "host cell" refers to any cell capable of replicating and/or transcribing and/or translating a heterologous gene.

As used herein, the term "divinyl ether synthase" (DES) refers to a polypeptide with the capacity to convert fatty acid hydroperoxides to divinyl ether fatty acids that contain an oxygen within the hydrocarbon chain. Substrates of DES comprise mono-, di-, and tri-hydroperoxy fatty acids; the chain length of such hydroperoxy fatty acids is variable, but is preferably 16 to 20 carbons in length. The hydroperoxy fatty acids may also comprise additional functional groups. The substrates are either free fatty acids, or are fatty acids incorporated into a larger molecule, such as a glycerolipid. The term "recombinant divinyl ether synthase" (recombinant DES) refers to the expression product of a recombinant nucleic acid molecule or of a heterologous gene encoding DES.

As used herein, the term "lipoxygenase" (LOX) refers to a polypeptide with the capacity to add molecular oxygen to polyunsaturated fatty acids which contain at least two double bonds, appropriately spaced, such as linoleic and linolenic acid, to generate fatty acid hydroperoxides. More specifically, lipoxygenase catalyzes incorporation of dioxygen into polyunsaturated fatty acids containing a 1Z,4Z-pentadiene structure. The chain length of the fatty acid substrates is variable, but is preferably 16 to 20 carbons in length. The unsaturated fatty acids may also comprise additional functional groups. The substrates are either free fatty acids, or are fatty acids incorporated into a larger molecule, such as a glycerolipid. The term "recombinant lipoxygenase" refers to the expression product of a recombinant nucleic acid molecule or of a heterologous gene encoding lipoxygenase.

As used herein, the term "competes for binding" is used in reference to a first polypeptide with enzymatic activity which binds to the same substrate as does a second polypeptide with enzymatic activity, where the second polypeptide is variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides.

The term "carrier" when used in reference to the application of a divinyl ether fatty acid to a plant of other organism refers to compounds with which divinyl ether fatty acid can be combined or mixed, or into which they can be dissolved or suspended or mixed. Suitable carriers which are well known include but are not limited to water, solvents, aqueous solutions, slurries, or dry powders; additional carriers include petrolatum products and diatomaceous earth (see e.g. U.S. Pat. No. 5,326,560). Other additional components, which may facilitate application of the composition to plants or seeds and which are well known, include but are not limited to buffering agents, wetting agents, coating agents, abrading agents and other adjuvants, including but not limited to petroleum based materials or vegetable based materials, corn-starch encapsulated herbicide granules, citric acid, and complex polysaccharides (see e.g., U.S. Pat. No. 5,945,377) and alkali metal silicates (see e.g. U.S. Pat. No. 5,183,477).

The term "components which aid seed storage and germination" refer to compounds which tend to increase the proportion of seeds which germinate after storage for any given period of time. The most effective compounds for any combination of a particular seed and storage condition and period of storage are well known, and include but are not limited to components of conventional seed formulations and treatment materials, such as clays and polysaccharides.

As used herein, the term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

As used herein, the term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

As used herein, the term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As used herein, the terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

As used herein, the term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

As used herein, the term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarily between nucleic acid strands has significant effects on the efficiency and strength of hybridization between nucleic acid strands. This is of particular importance in amplification reactions, as well as detection methods which depend upon binding between nucleic acids.

As used herein, the term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

As used herein, the term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q_replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" refers to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue-, organ-, or cell-specific, as well as developmentally-specific. The term "tissue specific" as it applies to a promoter refers to a promoter that is capable of directing selective expression of a nucleotide sequence of interest in a specific type of tissue (e.g., xylem) compared to the relative absence of expression of the same nucleotide sequence of interest in a different type of tissue (e.g., phloem). Similarly, the term "organ specific" as it applies to a promoter refers to a promoter that is capable of directing selective expression of a nucleotide sequence of interest in a specific organ (e.g., leaves) compared to the relative absence of expression of the same nucleotide sequence of interest in a different type of tissue (e.g., roots) Tissue- and organ-specificity of a promoter may be evaluated by, for example, operably linking a reporter gene to the promoter sequence to generate a reporter construct, introducing the reporter construct into the genome of a plant such that the reporter construct is integrated into every tissue or organ of the resulting transgenic plant, and detecting the expression of the reporter gene (e.g., detecting mRNA, protein, or the activity of a protein encoded by the reporter gene) in different tissues or organs of the transgenic plant. The detection of a greater level of expression of the reporter gene in one or more tissues or organs relative to the level of expression of the reporter gene in other tissues or organs shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

A promoter may also be specific to a particular "developmental phase" of an organism. Such a promoter is capable of directing selective expression of a nucleotide sequence of interest at a particular period or phase in the life of an organism (e.g., seed formation), compared to the relative absence of expression of the same nucleotide sequence of interest in a different phase (e.g., seed germination). For example, in plants, seed-specific promoters are promoters are typically active during the development of seeds; germination promoters are typically active during germination of the seeds.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap, Plant Mol. Biol. 24:119-127 [1994]) promoters.

Such promoters have been used successfully to direct the expression of heterologous nucleic acid sequences in transformed plant tissue.

In contrast, a "regulatable" or "inducible" promoter is one which is capable of directing a level of transcription of an operably linked nuclei acid sequence in the presence of a stimulus (e.g., heat shock, chemicals, light, etc., where such stimuli are referred to as inducers) which is different from the level of transcription of the operably linked nucleic acid sequence in the absence of the stimulus.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

As used herein, the term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

As used herein, the term "vector" refers to nucleic acid molecules that transfer DNA segment(s) from one cell to another. The term "vehicle" is sometimes used interchangeably with "vector."

As used herein, the terms "expression vector" or "expression cassette refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the terms "transfect," "transform," and variations refer to the introduction of foreign DNA into cells. The terms "cotransfect," "cotransform" and variations refer to the introduction of at least two different foreign DNA molecules into a single host cell; the DNA molecules may differ, for example, in the coding sequence, or in regulatory sequences. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

As used herein, the terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208, GV3101) are referred to as "nopaline-type" Agrobacteria; *Agrobacterium* strains which cause production of octopine (e.g., strain LBA4404, Achy, B6) are referred to as "octopine-type" Agrobacteria; and *Agrobacterium* strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

As used herein, the term "transgenic" when used in reference to a plant or fruit or seed (i.e., a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

As used herein, the terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

As used herein, the term "overexpression" refers to the production of a gene product in transgenic organisms that exceeds levels of production in normal or non-transformed organisms. As used herein, the term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

As used herein, the term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

As used herein, the terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, NY, pp 9.31-9.58).

As used herein, the term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used Northern blots are a standard tool of molecular biologists (J. Sambrook, et al. [1989] supra, pp 7.39-7.52).

As used herein, the terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

As used herein, the terms "protein" and "polypeptide" refer to compounds comprising amino acids joined via peptide bonds and are used interchangeably.

As used herein, where "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule; furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

As used herein, the term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a DES includes, by way of example, such nucleic acid in cells ordinarily expressing a DES, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

As used herein, the term "purified" refers to molecules, as for example either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of molecule, as for example a polypeptide, of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, the term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DETAILED DESCRIPTION OF THE INVENTION

The presently claimed invention provides compositions comprising isolated DES genes and polypeptides, and in particular to compositions comprising isolated plant DES genes and polypeptides. The present invention also provides methods for using DES genes, polypeptides, and synthase products; such methods include but are not limited to protecting plants from pathogens, and using DES genes and polypeptides in the production of divinyl ether fatty acids. The description below provides specific, but not limiting, illustrative examples of embodiments of the present invention.

I. Divinyl Ether Synthase Genes

The biosynthesis of most plant oxylipins is initiated by lipoxygenases (LOXs) that add molecular oxygen to polyunsaturated fatty acids to generate hydroperoxy fatty acids, such as to either the 9 or 13 position of linolenic acid or linoleic acid (FIG. 1). Hydroperoxide products of LOX are then committed to various branches of oxylipin metabolism. For example, allene oxide synthase (AOS) transforms 13-hydroperoxy linolenic (13-HPOT) to an unstable allene oxide that either converts spontaneously to (alpha and gamma ketols, or serves as the precursor for enzymatic synthesis of JA and related cyclopentenones (Vick and Zimmerman, Plant Physiol. 79: 490-494 [1979]; Brash et al., Proc. Natl. Acad. Sci. U.S.A. 85: 3382-3386 [1988]). A second well-studied enzyme, hydroperoxide lyase (HPL), cleaves 13-HPOT into short chain aldehydes.

AOS and HPL are members of a family (CYP74) of cytochrome P450s that are specialized for the metabolism of fatty acid hydroperoxides (Song et al., Proc. Natl. Acad. Sci. U.S.A. 90: 8519-8523 [1993]; Matsui, et al., FEBS Lett. 394: 21-224 [1996]). In contrast to P450 monooxygenases that use NADPH and molecular oxygen for hydroxylation reactions, AOS (CYP74A) and HPL (CYP74B and C) utilize an acyl hydroperoxide both as the oxygen donor and as the substrate in which the new carbon-oxygen bonds are formed. Consistent with this, AOS and HPL do not require $O_2$ or NADPH for activity, and have reduced affinity for CO (Song and Brash, Science 252: 781-784 [1991]; Lau et al., Biochemistry 32: 945-1950 [1993]; Shibata et al., Biochem. Biophys. Res. Commun. 207: 438-443 [1995]; Shibata, et al., Plant Cell Physiol. 36: 147-156 [1995]).

In addition to the AOS and HPL pathways, fatty acid hydroperoxides are converted by divinyl ether synthase (DES) to divinyl ethers that contain an oxygen within the hydrocarbon chain (FIG. 1). In potato, divinyl ethers called colneleic acid (CA) and colnelenic acid (CnA) are produced from linoleic and linolenic acids, respectively, by the sequential action of 9-LOX and a DES that is specific for 9-hydroperoxides (Gallard and Phillips Biochem. J. 129: 743-753 [1972]; Gallard and Phillips, Chem. Phys. Lipids 11: 173-180 [1973]). Divinyl ethers derived from 13-hydroperoxides are synthesized by a similar two-step pathway in garlic bulb and green leaves of meadow buttercup (Grechkin et al., FEBS Lett. 371: 159-162 [1995]; Hamberg, Lipids 33: 1061-1071 [1998]). The structure of divinyl ether fatty acids in the marine alga *Laminaria sinclairii* suggests the involvement of a DES that metabolizes 13- and 15-hydroperoxides of C18 and C20 polyunsaturated fatty acids (Proteau and Gerwick, Lipids 28: 783-787 [1993]). *Polyneura latissima*, a red alga, accumulates an eicosanoid divinyl ether whose structure and co-existence with 9-hydroxy-eicosatetraenoic acid suggest a biosynthetic route from 9-LOX (Jaing and Gerwick, Lipids 32: 231-235 1997]).

Although the biosynthesis of divinyl ether oxylipins in various plant tissues has been reported, purification of DES or cloning of a DES-encoding nucleic acid sequences has not been reported.

A. Divinyl Synthase Genes

Some embodiments of the present invention contemplate methods to isolate nucleic acid sequences encoding DES, based upon the hypothesis that DES is also be a member of the CYP74 family of cytochrome P450s. The methods involve first an examination of a plant expressed sequence tag (EST) database, in order to discover novel potential CYP74 encoding sequences. These methods next involve sequencing likely candidate sequences, and characterizing the expression products of such sequences so discovered.

Employing these methods resulted in the discovery of a full-length cDNA from tomato that defined a new subfamily of CYP74 P450s, as described in illustrative Examples 1-3. The nucleotide (SEQ ID NO:1) and deduced amino acid sequence (SEQ ID NO:2) of the LeDES cDNA are shown in FIG. 2. This new family of CYP74 P450s is classified as CYP74D, and the novel tomato CYP74D is classified as the first member of this family, as CYP74D1, according to guidelines for cytochrome p450 nomenclature. The isolated novel cDNA was demonstrated to encode DES, as described in Examples 1-3, and is referred to as LeDES cDNA, which indicates both the source (*Lycopersicon esculentum*) and the activity of the encoded polypeptide (DES). Thus, in some embodiments of the present invention, isolated nucleic acid sequences encoding DES are provided (for example, SEQ ID NO:1).

The LeDES cDNA can be used as to locate and isolate the tomato DES gene, by methods well known in the art. For example, as described in Examples 1-3, LeDES is a single copy gene located on the distal half of the long arm of chromosome 1. To isolate the gene, a $^{32}$P-radiolabeled LeDES cDNA is used to screen, by DNA-DNA hybridization, a genomic library constructed from tomato genomic DNA. Single isolated clones that test positive for hybridization are proposed to contain part or all of the LeDES gene, and are sequenced. The sequence of these positive cloned tomato genomic DNA is used to confirm the identity of the gene as LeDES. If a particular clone encodes only part of the gene, additional clones that test positive for hybridization to the LeDES cDNA are isolated and sequenced. Comparison of the full-length sequence of the LeDES gene to the cDNA are used to determine the location of introns, if they are present.

Other methods provided by the present invention to isolate nucleic acid sequences encoding DES include providing a candidate sequence encoding a polypeptide. Such candidates are obtained by any of several procedures; some are as described above, by examining a plant expressed sequence tag (EST) database, in order to discover novel potential CYP74 encoding sequences, and determining the sequence of likely candidate sequences. Other methods for obtaining candidate sequences include examining plant gene databases to discover sequences encoding novel potential CYP74 proteins by methods well known in the art. The methods involve next deducing the encoded amino acid sequence, and analyzing the candidate polypeptide for the presence of characteristics of the DES protein. These characteristics include the motif AGxxAF in the I-helix consensus sequence, as described in greater detail below.

B. Additional Divinyl Ether Synthase Genes

The present invention provides nucleic acid sequences encoding DES. For example, some embodiments of the present invention provide polynucleotide sequences that are capable of hybridizing to SEQ ID NO: 1 under conditions of low to high stringency as long as the polynucleotide sequence capable of hybridizing encodes a protein that retains a desired biological activity of the naturally DES. In preferred embodiments, hybridization conditions are based on the melting temperature ($T_m$) of the nucleic acid binding complex and confer a defined "stringency" as explained above (See e.g., Wahl et al., Meth. Enzymol., 152:399-407 [1987], incorporated herein by reference).

In other embodiments of the present invention, alleles of DES are provided. In preferred embodiments, alleles result from a mutation, (i.e., a change, in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In other embodiments of the present invention, the polynucleotide sequence encoding DES is extended utilizing the nucleotide sequences (e.g., SEQ ID NO:1) in various methods known in the art to detect upstream sequences such as promoters and regulatory elements. For example, it is contemplated that polymerase chain reaction (PCR) finds use in the present invention. This is a direct method that uses universal primers to retrieve unknown sequence adjacent to a known locus (Gobinda et al., PCR Methods Applic., 2:318-22 [1993]). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR is used to amplify or extend sequences using divergent primers based on a known region (Triglia et al., Nucleic Acids Res., 16:8186 [1988]). The primers may be designed using Oligo 4.0 (National Biosciences Plymouth Minn.), or another appropriate program, to be, for example, 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In yet another embodiment of the present invention, capture PCR (Lagerstrom et al., PCR Methods Applic., 1:111-19 [1991]) is used. This is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR. In still other embodiments, walking PCR is utilized. Walking PCR is a method for targeted gene walking that permits retrieval of unknown sequence (Parker et al., Nucleic Acids Res., 19:3055-60 [1991]). The PROMOTERFINDER kit (Clontech) uses PCR, nested primers and special libraries to "walk in" genomic DNA. This process avoids the need to screen libraries and is useful in finding intron/exon junctions. In yet other embodiments of the present invention, add TAIL PCR is used as a preferred method for obtaining flanking genomic regions, including regulatory regions (Lui and Whittier, [1995]; Lui et al., [1995]), as described in Examples 1A and 2B.

Preferred libraries for screening for full length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

C. Generation of Mutant Divinyl Ether Synthases

In some embodiments, the present invention provides isolated variants of the disclosed nucleic acid sequence encoding DES, and the polypeptides encoded thereby; these variants include mutants, fragments, fusion proteins or functional equivalents of DES. Thus, nucleotide sequences of the present invention are engineered in order to alter a DES coding sequence for a variety of reasons, including but not limited to alterations that modify the cloning, processing and/or expression of the gene product (such alterations include inserting new restriction sites, altering glycosylation patterns, and changing codon preference) as well as varying the enzymatic activity (such changes include but are not limited to differing substrate affinities, differing substrate preferences and utilization, differing inhibitor affinities or effectiveness, differing reaction kinetics, varying subcellular localization, and varying protein processing and/or stability). For example, mutations are introduced which alter the substrate specificity, such that the preferred substrate is changed from 9-HPOD to 13-HPOD, in an analogous manner to that observed for LOX, in which a single amino acid substitution resulted in a change in the substrate specificity to the 9-10 double bond from the 13-14 double bond (Hornung, Proc. Natl. Acad. USA 96: 4192-4197 [1999]).

In other embodiments, the present invention provides isolated nucleic acid sequences encoding a divinyl ether synthase, where the encoded synthase competes for binding to a dihydroperoxide fatty acid substrate with a protein encoded by a nucleic acid sequence comprising SEQ ID NO: 1.

Mutants of DES can be generated by any suitable method well known in the art, including but not limited to site-directed mutagenesis, randomized "point" mutagenesis, and domain-swap mutagenesis in which portions of the LeDES cDNA are "swapped" with the analogous portion of other CYP74 P450-encoding cDNAs (Back and Chappell, PNAS 93: 6841-6845, [1996]).

1. Variants of Divinyl Ether Synthase a. Mutants

Some embodiments of the present invention provide mutant or variant forms of DES (i.e., muteins). In preferred embodiments, variants result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that is possible to modify the structure of a peptide having an activity (e.g., DES activity) for such purposes as increasing synthetic activity or altering the affinity of the DES for a particular fatty acid substrate. Such modified peptides are considered functional equivalents of peptides having an activity of an DES as defined herein. A modified peptide can be produced in which the nucleotide sequence encoding the polypeptide has been altered, such as by substitution, deletion, or addition. In some preferred embodiments of the present invention, the alteration increases synthetic activity or alters the affinity of the DES for a particular fatty acid substrate. In particularly preferred embodiments, these modifications do not significantly reduce the synthetic activity of the modified enzyme. In other words, construct "X" can be evaluated in order to determine whether it is a member of the genus of modified or variant DES of the present invention as defined functionally, rather than structurally. In preferred embodiments, the activity of variant DES is evaluated by the methods described in Example 1D. Accordingly, in some embodiments the present invention provides nucleic acids encoding DES that complement the coding region of SEQ ID NO: 1. In other embodiments, the present invention provides nucleic acids encoding DES that compete for the binding of fatty acid substrates with the protein encoded by SEQ ID NO: 1.

Moreover, as described above, variant forms of DES are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of ACSs disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

b. Directed Evolution

Variants may be produced by methods such as directed evolution or other techniques for producing combinatorial libraries of variants. Thus, the present invention further contemplates a method of generating sets of combinatorial mutants of the present DES proteins, as well as truncation mutants, and is especially useful for identifying potential variant sequences (i.e., homologs) that possess the biological activity of DES (e.g., synthesis of divinyl ether fatty acids). In addition, screening such combinatorial libraries is used to generate, for example, novel DES homologs that possess novel substrate specificities or other biological activities all together, examples of substrate specificities are described subsequently.

It is contemplated that the DES nucleic acids (e.g., SEQ ID NO: 1, and fragments and variants thereof) can be utilized as starting nucleic acids for directed evolution. These techniques can be utilized to develop DES variants having desirable properties such as increased synthetic activity or altered affinity for a particular fatty acid substrate.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 [1996]; Leung et al., Technique, 1:11-15 [1989]; Eckert and Kunkel, PCR Methods Appl., 1:17-24 [1991]; Caldwell and Joyce, PCR Methods Appl., 2:28-33 (1992); and Zhao and Arnold, Nuc. Acids. Res., 25:1307-08 [1997]). After mutagenesis, the resulting clones are selected for desirable activity (e.g., screened for DES activity as described subsequently). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324-25 [1994]; U.S. Pat. Nos. 5,837,458; 5,830,721; 5,811,238; 5,733,731). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398-91 [1994]; Stemmer, Proc. Natl. Acad. Sci. USA, 91, 10747-51 [1994]; Crameri et al., Nat. Biotech., 14:315-19 [1996]; Zhang et al., Proc. Natl. Acad. Sci. USA, 94:4504-09 [1997]; and Crameri et al., Nat. Biotech., 15:436-38 [1997]). Variants produced by directed evolution can be screened for DES activity by the methods described subsequently (see Example 1H).

c. Homologs

Still other embodiments of the present invention provide isolated nucleic acid sequence encoding DES homologs, and the polypeptides encoded thereby. Some homologs of DES have intracellular half-lives dramatically different than the corresponding wild-type protein. For example, the altered protein are rendered either more stable or less stable to proteolytic degradation or other cellular process that result in destruction of, or otherwise inactivate DES. Such homologs, and the genes that encode them, can be utilized to alter the activity of DES by modulating the half-life of the protein. For instance, a short half-life can give rise to more transient DES biological effects. Other homologs have characteristics which are either similar to wild-type DES, or which differ in one or more respects from wild-type DES.

The cDNA deduced amino acid sequence of LeDES (CYP74D1) is compared to the cDNA deduced amino acid sequences of other known tomato CYP74 P450s as shown in FIG. 3. The underlined portion of the amino acid sequences correspond to the consensus sequence in P450 monooxygenases within the I-helix that forms part of the oxygen-binding pocket. The position of an invariant threonine in bacterial and mammalian P450s is indicated by the inverted carrot (^); this residue is believed to play a critical role in the binding and activation of oxygen. All reported CYP74 sequences have an isoleucine or valine in place of the conserved threonine, and conform to the consensus sequence GGxx(I/V)(L/F) (where the underlining indicates the position of the conserved threonine). The corresponding region of LeDES has the sequence AGxxAF which differs from all other CYP74 sequences in two positions, which are indicated in bold type (the underlining again indicates the position of the conserved threonine) Accordingly, in some embodiments, the present invention provides DES comprising at least the motif AGxxAF in the I-helix consensus sequence, or the nucleic acid sequences encoding such polypeptides. In yet other embodiments of the present invention, it is contemplated that nucleic acid sequences suspected of encoding a DES homolog is screened by comparing motifs. In some embodiments, the deduced amino acid sequence can be analyzed for the presence of the motif AGxxAF in the I-helix consensus sequence.

In some embodiments of the combinatorial mutagenesis approach of the present invention, the amino acid sequences for a population of DES homologs are aligned, preferably to promote the highest homology possible. Such a population of variants can include, for example, DES homologs from one or more species, or DES homologs from the same species but which differ due to mutation. Amino acids that appear at each position of the aligned sequences are selected to create a degenerate set of combinatorial sequences.

In a preferred embodiment of the present invention, the combinatorial DES library is produced by way of a degenerate library of genes encoding a library of polypeptides that each include at least a portion of candidate DES-protein sequences. For example, a mixture of synthetic oligonucleotides is enzymatically ligated into gene sequences such that the degenerate set of candidate DES sequences are expressible as individual polypeptides, or alternatively, as a set of larger fusion proteins (e.g., for phage display) containing the set of DES sequences therein.

There are many ways by which the library of potential DES homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential DES sequences. The synthesis of degenerate oligonucleotides is well known in the art (See e.g., Narang, Tetrahedron Lett., 39:3 9 [1983]; Itakura et al., Recombinant DNA, in Walton (ed.), Proceedings of the 3rd Cleveland Symposium on Macromolecules, Elsevier, Amsterdam, pp 273-289 [1981]; Itakura et al., Annu. Rev. Biochem., 53:323 [1984]; Itakura et al., Science 198: 1056 [1984]; Ike et al., Nucl. Acid Res., 11:477 [1983]). Such techniques have been employed in the directed evolution of other proteins (See e.g., Scott et al., Science, 249:386-390 [1980]; Roberts et al., Proc. Natl. Acad. Sci. USA, 89:2429-2433 [1992]; Devlin et al., Science, 249: 404-406 [1990]; Cwirla et al., Proc. Natl. Acad. Sci. USA, 87: 6378-6382 [1990]; as well as U.S. Pat. Nos. 5,223,409, 5,198,346, and 5,096,815).

d. Screening Gene Products

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of DES homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in one embodiment of the present invention, the candidate DES gene products are displayed on the surface of a cell or viral particle, and the ability of particular cells or viral particles to synthesize divinyl ether fatty acids is assayed using the techniques described in Example 1E. In other embodiments of the present invention, the gene library is cloned into the gene for a surface membrane protein of a bacterial cell, and the resulting fusion protein detected by panning (WO 88/06630; Fuchs et al., BioTechnol., 9:1370-1371 [1991]; and Goward et al., TIBS 18:136-140 [1992]). In other embodiments of the present invention, fluorescently labeled molecules that bind DES can be used to score for potentially functional DES homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (See e.g., WO 90/02909; WO 92/09690; Marks et al., J. Biol. Chem., 267:16007-16010 [1992]; Griffiths et al., EMBO J., 12:725-734 [1993]; Clackson et al., Nature, 352:624-628 [1991]; and Barbas et al., Proc. Natl. Acad. Sci., 89:4457-4461 [1992]).

In another embodiment of the present invention, the recombinant phage antibody system (e.g., RPAS, Pharmacia Catalog number 27-9400-01) is modified for use in expressing and screening of DES combinatorial libraries. The pCANTAB 5 phagemid of the RPAS kit contains the gene that encodes the phage gIII coat protein. In some embodiments of the present invention, the DES combinatorial gene library is cloned into the phagemid adjacent to the gIII signal sequence such that it is expressed as a gIII fusion protein. In other embodiments of the present invention, the phagemid is used to transform competent E. coli TG1 cells after ligation. In still other embodiments of the present invention, transformed cells are subsequently infected with M13KO7 helper phage to rescue the phagemid and its candidate DES gene insert. The resulting recombinant phage contain phagemid DNA encoding a specific candidate DES-protein and display one or more copies of the corresponding fusion coat protein. In some embodiments of the present invention, the phage-displayed candidate proteins that are capable of, for example, metabolizing a hydroperoxide, are selected or enriched by panning. The bound phage is then isolated, and if the recombinant phage express at least one copy of the wild type gIII coat protein, they will retain their ability to infect E. coli. Thus, successive rounds of reinfection of E. coli and panning will greatly enrich for DES homologs, which can then be screened for further biological activities in order to differentiate agonists and antagonists.

In light of the present disclosure, other forms of mutagenesis generally applicable will be apparent to those skilled in the art in addition to the aforementioned rational mutagenesis based on conserved versus non-conserved residues. For example, DES homologs can be generated and screened using, for example, alanine scanning mutagenesis and the like (Ruf et al., Biochem., 33:1565-1572 [1994]; Wang et al., J. Biol. Chem., 269:3095-3099 [1994]; Balint Gene 137:109-118 [1993]; Grodberg et al., Eur. J. Biochem., 218:597-601 [1993]; Nagashima et al., J. Biol. Chem., 268:2888-2892 [1993]; Lowman et al., Biochem., 30:10832-10838 [1991]; and Cunningham et al., Science, 244:1081-1085 [1989]), by linker scanning mutagenesis (Gustin et al., Virol., 193:653-660 [1993]; Brown et al., Mol. Cell. Biol., 12:2644-2652 [1992]; McKnight et al., Science, 232:316); or by saturation mutagenesis (Meyers et al., Science, 232:613 [1986]).

2. Truncation Mutants of Divinyl Ether Synthase

In addition, the present invention provides isolated nucleic acid sequences encoding fragments of DES (i.e., truncation mutants), and the polypeptides encoded by such nucleic acid sequences. In preferred embodiments, the DES fragment is biologically active. In some embodiments of the present invention, when expression of a portion of a DES protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al., J. Bacteriol., 169:751-757 [1987]) and Salmonella typhimurium and its in vitro activity has been demonstrated on recombinant proteins (Miller et al., Proc. Natl. Acad. Sci. USA, 84:2718-1722 [1990]). Therefore, removal of an N-terminal methionine, if desired, can be achieved either in vivo by expressing such recombinant polypeptides in a host that produces MAP (e.g., E. coli or CM89 or S. cerevisiae), or in vitro by use of purified MAP.

3. Fusion Proteins Containing DES

The present invention also provides nucleic acid sequences encoding fusion proteins incorporating all or part of DES, and the polypeptides encoded by such nucleic acid sequences. In some embodiments, the fusion proteins have a DES functional domain with a fusion partner. Accordingly, in some embodiments of the present invention, the coding sequences for the polypeptide (e.g., a DES functional domain) is incorporated as a part of a fusion gene including a nucleotide sequence encoding a different polypeptide. For example, the coding sequence for DES is fused to the coding sequence for LOX, resulting in expression of a single polypeptide with two enzymatic activities, in an analogous manner as occurs naturally in coral for a fusion protein containing both LOX and allene oxide synthase (Koljak et al., Science 277: 1994-1996 [1997]; Boutand and Brash, J. Biol. Chem. 274: 33764-33770 [1999]). It is contemplated that such a single fusion product polypeptide converts a polyunsaturated fatty acid to a divinyl ether fatty acid.

In some embodiments of the present invention, chimeric constructs code for fusion proteins containing a portion of DES and a portion of another gene. In some embodiments, the fusion proteins have biological activity similar to the wild type DES (e.g., have at least one desired biological activity of DES). In other embodiments, the fusion protein have altered biological activity In addition to utilizing fusion proteins to alter biological activity, it is widely appreciated that fusion proteins can also facilitate the expression and/or purification of proteins, such as the DES protein of the present invention. Accordingly, in some embodiments of the present invention, DES is generated as a glutathione-S-transferase (i.e., GST fusion protein). It is contemplated that such GST fusion proteins enables easy purification of DES, such as by the use of glutathione-derivatized matrices (See e.g., Ausabel et al. (eds.), Current Protocols in Molecular Biology, John Wiley & Sons, NY [1991]).

In another embodiment of the present invention, a fusion gene coding for a purification leader sequence, such as a poly-(His)/enterokinase cleavage site sequence at the N-terminus of the desired portion of DES allows purification of the expressed DES fusion protein by affinity chromatography using a $Ni^{2+}$ metal resin. In still another embodiment of the present invention, the purification leader sequence is then subsequently removed by treatment with enterokinase (See e.g., Hochuli et al., J. Chromatogr., 411:177 [1987]; and Janknecht et al., Proc. Natl. Acad. Sci. USA, 88:8972). In yet other embodiments of the present invention, a fusion gene coding for a purification sequence appended to either the N or the C terminus allows for affinity purification; one example is addition of a hexahistidine tag to the carboxy terminus of DES which was optimal for affinity purification, as described in Example 3A.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See e.g., Current Protocols in Molecular Biology, supra).

D. Expression of Cloned Divinyl Ether Synthase

In other embodiment of the present invention, nucleic acid sequences corresponding to the DES genes, homologs and mutants as described above may be used to generate recombinant DNA molecules that direct the expression of the encoded protein product in appropriate host cells.

As will be understood by those of skill in the art, it may be advantageous to produce DES-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) can be selected, for example, to increase the rate of DES expression or to produce recombinant RNA transcripts having desirable properties, such as a longer half-life, than transcripts produced from naturally occurring sequence.

1. Vectors for Production of DES

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above (e.g., SEQ ID NO: 1). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, the nucleic acid sequence in the expression vector is operatively linked to an appropriate expression control sequence(s) (promoter) to direct mRNA synthesis. Promoters useful in the present invention include, but are not limited to, the LTR or SV40 promoter, the $E.\ coli$ lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in $E.\ coli$).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of Divinyl Ether Synthase

In a further embodiment, the present invention provides host cells containing the above-described constructs. In some embodiments of the present invention, the host cell is a higher eukaryotic cell (e.g., a plant cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomyces cerivisiae, Schizosaccharomyces pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), 293T, C127, 3T3, HeLa and BHK cell lines, NT-1 (tobacco cell culture line), root cell and cultured roots in rhizosecretion (Gleba et al., Proc Nail Acad Sci USA 96: 5973-5977 [1999])

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of Divinyl Ether Synthase

The present invention also provides methods for recovering and purifying DES from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

In some embodiments of the present invention, the protocol of Example 1E is used to purify recombinant DES. In this illustrative example, DES was purified from bacterial extracts using affinity chromatography.

The present invention further provides nucleic acid sequences having the coding sequence (e.g., SEQ ID NO: 1) fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminal of DES and which results in expression of the polypeptide in the case of a bacterial host, and more preferably by vector PT-23B, which adds a hexahistidine tag to the C terminal of DES and which results in improved ease of purification of the polypeptide fused to the marker in the case of a bacterial host (see Example 1C), or, for example, the marker sequence may be a hemagglutinin (HA) tag when a mammalian host is used. The HA tag corresponds to an epitope derived from the influenza hemagglutinin protein (Wilson et al., Cell, 37:767 [1984]).

II. Divinyl Ether Synthase Polypeptides

The present invention provides DES polypeptides as well as variants, homologs, mutants or fusion proteins thereof. In some embodiments of the present invention, the polypeptide may be a naturally purified product, while in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment (as described in Example 3), DES encoded by a *Lycopersicon esculentum* gene has a molecular weight of about 55,250, as calculated from the amino acid sequence and as determined from SDS gel electrophoresis. The enzyme activity of a recombinant enzyme appears to be associated with membranes, even though the DES amino acid sequence appears to lack an ER targeting domain typically found in other cytochrome P450 proteins. These proteins are usually associated with ER membranes, with a single transmembrane domain at the N terminus such that the bulk of the enzyme faces the cytosol. DES may thus associate with membranes through another mechanism. Recombinant DES was active with both 9-HPOD and 9-HPOT, where the apparent $K_m$ for these substrates was about 67 and 48 µM, respectively. The spectral properties of the recombinant enzyme were typical of low spin cytochrome P450.

A. Purification of Divinyl Ether Synthase

In some embodiments of the present invention, DES polypeptides purified from recombinant organisms as described above are provided. In other embodiments, DES polypeptides purified from recombinant bacterial extracts transformed with tomato LeDES cDNA are provided (as described in Example 1E). The present invention provides purified DES polypeptides as well as variants, homologs, mutants or fusion proteins thereof, as described above.

Thus, the present invention provides DES purified from naturally occurring sources, as well as from transgenic sources, wherein the source is an organism comprises a nucleic acid sequence encoding a DES as described above. The purified DES is preferably purified to at least about 50%, more preferably purified to at least about 75%, even more preferably purified to at least about 90%, and most preferably purified to at least about 95%. Thus, in Example 1, recombinant DES expressed in *E. coli*, represents approximately 10% of total *E. coli* protein. The crude *E. coli* supernatant (containing about 10% DES protein), is highly active in terms of DES activity, and alone represents a significant purification. For utilization in the synthesis of divinyl ether fatty acids and other divinyl ether products, this level of purification is contemplated to be sufficient. Further purification of the recombinant DES, as described in Example 1E, results in DES representing about 50% of total membrane protein, about 50% of total detergent-solubilized membrane protein, and greater than about 95% of protein eluting from the cobalt affinity column.

B. Chemical Synthesis of Divinyl Ether Synthase

In an alternate embodiment of the invention, the coding sequence of DES is synthesized, whole or in part, using chemical methods well known in the art (See e.g., Caruthers et al., Nucl. Acids Res. Symp. Ser., 7:215-233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807-2817 [1981]). In other embodiments of the present invention, the protein itself is produced using chemical methods to synthesize either an entire DES amino acid sequence or a portion thereof. For example, peptides are synthesized by solid phase techniques, cleaved from the resin, and purified by preparative high performance liquid chromatography (See e.g., Creighton, Proteins Structures And Molecular Principles, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science, 269:202-204 [1995]) and automated synthesis may be achieved, for example, using ABI 431A Peptide Synthesizer (Perkin Elmer) in accordance with the instructions provided by the manufacturer. Additionally, the amino acid sequence of DES, or any part thereof, may be altered during direct synthesis and/or combined using chemical methods with other sequences to produce a variant polypeptide.

C. Generation of Divinyl Ether Synthase Antibodies

In some embodiments of the present invention, antibodies are generated to allow for the detection and characterization of DES protein. The antibodies may be prepared using various immunogens. In one embodiment, the immunogen is a tomato DES peptide (e.g., an amino acid sequence as depicted in SEQ ID NO:2, or fragments thereof) to generate antibodies that recognize tomato DES. Such antibodies include, but are not limited to polyclonal, monoclonal, chimeric, single chain, Fab fragments, and Fab expression libraries.

Various procedures known in the art may be used for the production of polyclonal antibodies directed against DES. For the production of antibody, various host animals can be immunized by injection with the peptide corresponding to the DES epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward DES, it is contemplated that any technique that provides for the production of antibody molecules by continuous cell lines in culture finds use with the present invention (See e.g., Harlow and Lane, Antibodies: A Laboratory Manual, Cold Spring Harbor Laboratory Press, Cold Spring Harbor, N.Y.). These include but are not limited to the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies may be generated by human hybridomas (Cote et al., Proc. Natl. Acad. Sci. USA, 80:2026-2030 [1983]) or by transforming human B cells with EBV virus in vitro (Cole et al., in Monoclonal Antibodies and Cancer Therapy, Alan R. Liss, pp. 77-96 [1985]).

In addition, it is contemplated that techniques described for the production of single chain antibodies (U.S. Pat. No. 4,946,778) find use in producing DES-specific single chain antibodies. An additional embodiment of the invention utilizes the techniques described for the construction of Fab expression libraries (Huse et al., Science, 246:1275-1281 [1989]) to allow rapid and easy identification of monoclonal Fab fragments with the desired specificity for DES.

It is contemplated that any technique suitable for producing antibody fragments finds use in generating antibody fragments that contain the idiotype (antigen binding region) of the antibody molecule. For example, such fragments include but are not limited to: $F(ab')_2$ fragment that can be produced by pepsin digestion of the antibody molecule; Fab' fragments that can be generated by reducing the disulfide bridges of the $F(ab')_2$ fragment, and Fab fragments that can be generated by treating the antibody molecule with papain and a reducing agent.

In the production of antibodies, it is contemplated that screening for the desired antibody is accomplished by techniques known in the art (e.g., radioimmunoassay, ELISA (enzyme-linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of DES (e.g., for Western blotting), measuring levels thereof in appropriate biological samples, etc. The antibodies can be used to detect DES in a biological sample from a plant. The biological sample can be an extract of a tissue, or a sample fixed for microscopic examination.

The biological samples are then be tested directly for the presence of DES using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of DES detected by immunoblotting (Western blotting). Immunoblotting techniques are generally more effective with antibodies generated against a peptide corresponding to an epitope of a protein, and hence, are particularly suited to the present invention.

III. Production of Large Quantities of Divinyl Ether Fatty Acids

In one aspect of the present invention, methods are provided for producing large quantities of divinyl ether fatty acids. In some embodiments, divinyl ether fatty acids are produced in vivo, in organisms transformed with a heterologous gene encoding a polypeptide exhibiting divinyl ether synthase activity and grown under conditions sufficient to effect production of divinyl ether fatty acids. In other embodiments, divinyl ether fatty acids are produced in vitro in plant tissue homogenates. In yet other embodiments, divinyl ether fatty acids are produced in vitro, from either nucleic acid sequences encoding a DES or from polypeptides exhibiting divinyl ether synthase activity.

A. In Vivo in a Transgenic Organism

In some embodiments of the present invention, divinyl ether fatty acids are produced in vivo, by providing an organism transformed with a heterologous gene encoding a DES activity and growing the transgenic organism under conditions sufficient to effect production of divinyl ether fatty acids. In other embodiments of the present invention, divinyl ether fatty acids are produced in vivo by transforming an organism with a heterologous gene encoding a DES and growing the transgenic organism under conditions sufficient to effect production of divinyl ether fatty acids.

Organisms which are transformed with a heterologous gene encoding a divinyl ether synthase include preferably those which naturally synthesize and store in some manner fatty acids, and those which are commercially feasible to grow and suitable for harvesting the fatty acid products. Such organisms include but are not limited to bacteria and plants. Non-limiting examples of bacteria include *E. coli* and related bacteria which can be grown in commercial-scale fermenters. Non-limiting examples of plants include preferably oil-producing plants, such as soybean, rapeseed and canola, sunflower, cotton, corn, cocoa, safflower, oil palm, coconut palm, flax, castor, and peanut. Non-commercial cultivars of plants can be transformed, and the trait for expression of DES moved to commercial cultivars by plant breeding techniques well-known in the art. In other embodiments, the plants possess high levels of endogenous LOX activity; examples include but are not limited to tomato and corn. These plants possess the capacity to produce high levels of the hydroperoxide fatty acid substrates of DES.

A heterologous gene encoding a DES, which includes mutants or variants of DES, includes any suitable sequence as described previously Preferably, the heterologous gene is provided within an expression vector such that transformation with the vector results in expression of the polypeptide; suitable vectors are described previously and subsequently.

A transgenic organism is grown under conditions sufficient to effect production of divinyl ether fatty acids. In some embodiments of the present invention, a transgenic organism is supplied with exogenous substrates of the DES. Such substrates comprise mono-, di-, and tri-hydroperoxy fatty acids; the chain length of such hydroperoxy fatty acids is variable, but is preferably 16 to 20 carbons in length. The hydroperoxy fatty acids may also comprise additional functional groups, including but not limited to acetylenic bonds, conjugated acetylenic and ethylenic bonds, allenic groups, cyclopropane, cyclopropene, cyclopentene and furan rings, epoxy-, and keto-groups and double bonds of both the cis and trans configuration and separated by more than one methylene group; two or more of these functional groups may be found in a single fatty acid. The substrates are either free fatty acids, or are fatty acids incorporated into a larger molecule, such as a glycerolipid. Most preferably, such substrates are selected from the group consisting of 9-hydroperoxy linoleic acid, 13-hydroperoxy linoleic acid, 9-hydroperoxy linolenic acid, and 13-hydroperoxy linolenic acid. Substrates may be supplied in various forms as are well known in the art; such forms include aqueous suspensions prepared by sonication, aqueous suspensions prepared with detergents and other surfactants, dissolution of the substrate into a solvent, and dried powders of substrates. Such forms may be added to organisms or cultured cells or tissues grown in fermenters, or may be applied to larger organisms, such as pot- or field-grown plants, by any of several known techniques, such as by irrigating, spraying, or fumigating.

In yet other embodiments of the present invention, a transgenic organism comprises a heterologous gene encoding a DES operably linked to an inducible promoter, and is grown either in the presence of the an inducing agent, or is grown and then exposed to an inducing agent. In still other embodiments of the present invention, a transgenic organism comprises a heterologous gene encoding a DES operably linked to a promoter which is either tissue- or organ-specific or developmentally specific, and is grown to the point at which the tissue or organ is developed or the developmental stage at which the developmentally-specific promoter is activated; preferably, the tissue or organ is one which is easily or typically harvested, such as leaves, fruits, or seeds.

In alternative embodiments, a transgenic organism as described above is engineered to produce greater amounts of the hydroperoxide substrate. Preferably, a transgenic organism is co-transformed with a heterologous gene encoding a polypeptide which exhibits LOX activity, such that the LOX is expressed. More preferably, the DES and the LOX are targeted to the same intracellular location; most preferably, such a location serves to store oil, such as a microsome in plants. These co-transformants are then grown under conditions sufficient to effect production of divinyl ether fatty acids. In some embodiments of the present invention, a co-transformant is supplied with exogenous substrates of the LOX; such substrates comprise poly-unsaturated fatty acids with at least two unsaturated double bonds. More specifically, LOX catalyzes incorporation of dioxygen into polyunsaturated fatty acids containing a 1Z,4Z-pentadiene structure. The chain length of such fatty acids is variable, but is preferably 16 to 20 carbons in length. The unsaturated fatty acids may also comprise additional functional groups, including but not limited to acetylenic bonds, conjugated acetylenic and ethylenic bonds, allenic groups, cyclopropane, cyclopropene, cyclopentene and furan rings, epoxy-, hydroxy- and keto-groups and double bonds of both the cis and trans configuration and separated by more than one methylene group; two or more of these functional groups may be found in a single fatty acid. The substrates are either free fatty acids, or are fatty acids incorporated into a larger molecule, such as a glycerolipid. Most preferably, such substrates are selected from the group consisting of linoleic and linolenic acid. Substrates may be supplied, added, or applied as described above.

In other embodiments, the heterologous genes are under control of promoters which are either inducible, tissue-specific, or developmentally specific, and the organism is grown as described above, such that the heterologous genes encoding polypeptides with LOX and DES activities are expressed.

In yet further embodiments of the invention, an organism is transformed with a nucleotide sequence coding for a fusion protein comprising both LOX and DES, as previously described, such that both enzymatic activities are expressed. Such transgenic organisms are grown as described above.

In other embodiments of the present invention, the methods for producing large quantities of divinyl ether fatty acids further comprise collecting the divinyl ether fatty acids produced. Such methods are known generally in the art, and include harvesting the transgenic organisms or parts of the organisms, and extracting the divinyl ether fatty acids. Thus, the collected divinyl ether fatty acids are thus purified from the source of production; purification is preferably at least about 50%, more preferably at least about 90%, and even more preferably at least about 95%. Extraction procedures preferably include solvent extraction, and typically include disrupting cells, as by chopping, mincing, grinding, and/or sonicating, prior to solvent extraction. In an embodiment of the present invention, solvent extraction comprises acidifying a disrupted cell mixture, as for example to pH 4.0 with 1 M sodium citrate, extracting the fatty acid products with an appropriate solvent, as for example twice with diethyl ether, drying the solvent extracts, preferably under nitrogen, and redissolving the dried ether fatty acid extracts in a suitable solvent, for example in methanol. In yet other embodiments of the present invention, the divinyl ether fatty acids are further purified, as for example by thin layer liquid chromatography, gas-liquid chromatography, or high pressure liquid chromatography.

B. In Vitro Homogenates

In other embodiments, divinyl ether fatty acids are produced in vitro, from homogenates obtained from organisms; in some embodiments, the organisms are transgenic, and comprise at least one heterologous gene encoding DES or LOX, or two heterologous genes encoding both DES and LOX. In some preferred embodiments, the organisms are plants. Homogenates are obtained by disrupting an organism, as by chopping, mincing, grinding, sonicating, and/or freeze-thawing; typically, these procedures occur in an aqueous suspension of material subjected to the procedures. The homogenate is then incubated for a period of time. Although it is not necessary to understand the mechanism in order to use the present invention, and it is not intended that the invention be so limited, it is believed that disruption of cells results in the release of fatty acid substrates from membrane lipids by the action of acyl-hydrolases; the substrates then enter the LOX-DES pathway, to result in the production of divinyl ether fatty acid products.

In some embodiments, the initial homogenate may be purified to various degrees; such purification steps include filtration and low-speed centrifugation to remove tissue and cellular debris. In other embodiments, various compounds are added to the homogenate, such as protease inhibitors to prevent protein degradation, and anti-oxidants to prevent degradation of or increased toxicity due to synthesis of the divinyl fatty acid products. In some embodiments, the incubation is from one to several hours, and the temperature ranges from about ten degrees to about room temperature.

Some homogenates are obtained from a transgenic organism comprising heterologous nucleic acid sequence encoding DES. In some embodiments, exogenous LOX is added to the homogenate. In other embodiments, the transgenic organism has high levels of endogenous levels LOX; in preferred embodiments, the transgenic organism is a plant, and in particularly preferred embodiments, the transgenic organism is a tomato or a corn plant, in which endogenous levels of 9-LOX are very high. 9-LOX converts linoleic and linolenic acids to 9-hydroperoxy linoleic acid and 9-hydroperoxy linolenic acid, which are substrates for DES. In other embodiments, the organism is co-transfected with both heterologous DES and heterologous LOX; in preferred embodiments, the transgenic organism is a plant. In other preferred embodiments, the heterologous genes are under control of promoters resulting in a high level of expression of the encoded enzymes. In yet other embodiments, the heterologous genes are under control of tissue- or organ-specific promoters, where the tissue or organ is easily harvested; for example, in corn and in tomato, the heterologous genes are preferably expressed in seeds and fruits. In preferred embodiments, the heterologous genes are under control of promoters which are both tissue- and organ-specific and which result in high levels of expression of the genes under control of the promoters.

In homogenates obtained from any of the organisms above, appropriate fatty acid substrates are optionally added at the initiation of or during the incubation of the homogenates. Thus, for example, in transgenic plants comprising heterologous DES and high levels of endogenous LOX activity, linoleic and linoleic acid may be added, to result in increased production of colneleic and colnelenic acids over levels observed in the absence of added exogenous substrates.

In other embodiments of the present invention, the methods for producing large quantities of divinyl ether fatty acids further comprise collecting the divinyl ether fatty acids produced, as described above.

In yet other embodiments of the present invention, the homogenates may be furthered processed for use as dietary supplements, as for example for animal feed or for food products for human consumption. For example, tomato homogenates may be used in sauces and condiments, whereas corn homogenates may be used for flours and for oils.

Thus, in an exemplary embodiment, the present invention provides a transgenic tomato plant comprising a heterologous gene encoding DES under control of a fruit-specific promoter which expresses DES at high levels; the plant is grown until mature tomato fruits are set; the tomato fruits are harvested, and the fruits are homogenized, and the homogenate incubated as described above. In alternative embodiments, the divinyl ether fatty acids are extracted as described above, or the homogenate is further processed for use in a feed or food product.

C. In Vitro Systems

In yet other embodiments of the present invention, divinyl ether fatty acids are produced in vitro, from either nucleic acid sequences encoding a DES or from polypeptides exhibiting divinyl ether synthase activity.

1. Using Nucleic Acid Sequences Encoding Divinyl Ether Synthase

In some embodiments of the present invention, methods for producing large quantities of divinyl ether fatty acids comprise adding an isolated nucleic acid sequence encoding a DES to in vitro expression systems under conditions sufficient to cause production of divinyl ether fatty acids. The isolated nucleic acid sequences encoding a DES is any suitable sequence as described previously, and preferably is provided within an expression vector such that addition of the vector to an in vitro transcription/translation system results in expression of the polypeptide. The system further comprises the substrates for DES, as previously described. Alternatively, the system further comprises the means for generating the substrates for DES. Such means include but are not limited to the provision of at least one protein exhibiting LOX activity, and substrates for LOX, as described previously.

In other embodiments of the present invention, the methods for producing large quantities of divinyl ether fatty acids further comprise collecting the divinyl ether fatty acids produced. Such methods are known generally in the art, and include for example acidifying the reaction system, as for example to pH 4.0 with 1 M sodium citrate, extracting the fatty acid products with an appropriate solvent, as for example twice with diethyl ether, drying the solvent extracts, preferably under nitrogen, and redissolving the dried fatty acid extracts in a suitable solvent, for example in methanol. In yet other embodiments of the present invention, the divinyl ether fatty acids are further purified, as for example by thin layer liquid chromatography, gas-liquid chromatography, or high pressure liquid chromatography.

2. Using Divinyl Ether Synthase Polypeptides

In some embodiments of the present invention, methods for producing large quantities of divinyl ether fatty acids comprise incubating a DES under conditions sufficient to result in the synthesis of divinyl ether fatty acids; generally, such incubation is carried out in a mixture which comprises the DES.

A DES, as described previously, is obtained by purification of either naturally occurring DES or recombinant DES from an organism transformed with heterologous gene encoding a DES, as previously described. A source of naturally occurring DES includes but is not limited to plants, as for example tomato, potato, garlic, meadow buttercup, marine alga including *Laminaria sinclairi*, and red alga including *Polyneura latissima*. A source of recombinant DES is either plant, bacterial or other transgenic organisms, transformed with heterologous gene encoding DES as described previously. The recombinant DES may include means for improving purification, as for example a 6×-His tag added to the C-terminus of the protein as described in Example 3A. Alternatively, DES is chemically synthesized.

The incubation mixture further comprises the substrates for DES, as described previously. Alternatively, the mixture further comprises the means for generating the substrates for DES. Such means include but are not limited to the provision of at least one protein exhibiting LOX activity, and appropriate substrates for LOX, as described previously.

In other embodiments of the present invention, the methods for producing large quantities of divinyl ether fatty acids further comprise collecting the divinyl ether fatty acids produced; such methods are described previously.

IV. Protection of Plants from Pathogens and Pests

The present invention also provides compositions and methods for protecting plants from pathogens. These methods and compositions are effective against a wide variety of plant pathogens and pests. Available evidence indicates that the present invention is effective against *Phytophthora infestans* (Weber et al., Plant Cell 11: 485-493 [1999]). It is further contemplated that the present invention is effective against a broad range of infective diseases and pests, including but not limited to nematode diseases (e.g., root knot), viral diseases (e.g., tobacco and tomato mosaic virus), bacterial diseases (e.g., *Pseudomonas* leaf spot, leaf speck, canker, stem rot, bacterial wilt), fungal diseases (e.g., *Alternaria* sten canker, black root rot, early blight, *Fusarium* wilt, Powdery mildew, *Pithium* diseases, *Verticillium* wilt), and herbivore pests (spider mites, aphids, caterpillars, whitefly, thrips). Collectively, this group of pathogens and allied species represent an economically important set of pathogens currently known for vegetables and other crop pests world-wide.

A. Exogenonsly Applied Divinyl Ether Fatty Acids

In an embodiment of the present invention, plants, seeds, or plant parts are protected against pathogens by application of a composition comprising at least one divinyl ether fatty acid to the plants or seeds or plant parts; preferably, the divinyl ether fatty acid is purified. Divinyl ether fatty acids are produced and purified as described previously. Preferably, the divinyl ether fatty acid is selected from the group consisting of CA and CnA, produced as described previously.

The method of the present invention relating to application of a composition comprising at least one divinyl ether fatty acid can be carried out through a variety of procedures when all or part of a plant is treated including leaves, stems, roots, etc. This may (but need not) involve infiltration of divinyl ether fatty acids into the plant. Suitable application methods include high or low pressure spraying, injection, dusting, and leaf abrasion proximate to when application of divinyl ether fatty acids occurs. When treating plant seeds, in accordance with the application embodiment of the present invention, a composition comprising at least one divinyl ether fatty acid can be applied by low or high pressure spraying, coating, immersion, dusting, or injection. Other suitable application procedures can be envisioned by those skilled in the art, provided the procedures are able to effect contact of the divinyl ether fatty acids with cells of the plant or plant seed. Once treated with divinyl ether fatty acids, the seeds can be planted in natural or artificial soil and cultivated using conventional procedures to produce plants.

After plants have been propagated from seeds treated in accordance with the present invention, the plants may be treated with one or more applications of composition comprising at least one divinyl ether fatty acid to protect the plants against pathogens. Such propagated plants may, in turn, be useful in producing seeds or propagules (e.g., cuttings) that produce plants capable of insect control.

A composition comprising at least one divinyl ether fatty acid can be applied to plants or plant seeds in accordance with the present invention alone or in a mixture with other materials. Alternatively, a composition comprising at least one divinyl ether fatty acid can be applied separately to plants with other materials being applied at different times.

A composition suitable for treating plants or plant sees in accordance with an embodiment of the present invention comprises at least one divinyl ether fatty acid, and may further comprise at least one suitable carrier which is well known in the art; non-limiting examples of suitable carriers include water, solvents, aqueous solutions, slurries, or dry powders; additional carriers include petrolatum products and diatomaceous earth (see e.g. U.S. Pat. No. 5,326,560). Such compositions may further preferably comprise low concentrations of detergents or surfactants, in order to solubilize divinyl ether fatty acids in an aqueous solution. Alternatively, the divinyl ether fatty acid can be suspended in an aqueous solution by mechanical means, such as sonication.

A composition may further comprise one or more additional components. Such additional components, which may aid plant growth and protection, include but are not limited to fertilizers, nutrients, hormones, insecticides, fungicides, nematocides, and herbicides. Suitable fertilizers include $(NH_4)NO_3$. Suitable nutrients are well known, and include but are not limited to at least one sugar, at least one macronutrient including but not limited to nitrogen, phosphorous, potassium and calcium, at least one micronutrient including but not limited to zinc, iron, and manganese, and at least one vitamin or cofactor (see e.g., U.S. Pat. Nos. 5,549,729 and 5,797,976). Suitable hormones include but are not limited to auxins (see e.g., U.S. Pat. No. 5,614,467). Suitable insecticides include Malathion. Suitable fungicides include Captan. Suitable herbicides include but are not limited to post-emergent herbicides such as nicosulfuron, isopropylamine salt, primisufluron, imidazolene, and glyphosphate (see e.g., U.S. Pat. No. 5,945,377).

Other additional components, which may facilitate application of the composition to plants or seeds and which are well known, include but are not limited to buffering agents, wetting agents, coating agents, abrading agents and other adjuvants, including but not limited to petroleum based materials or vegetable based materials, corn-starch encapsulated herbicide granules, citric acid, and complex polysaccharides (see e.g., U.S. Pat. No. 5,945,377) and alkali metal silicates (see e.g. U.S. Pat. No. 5,183,477). Other additional components, which may aid seed storage and germination, include but are not limited to components of convention seed formulations and treatment materials, such as clays and polysaccharides.

B. Endogenously Generated Divinyl Ether Fatty Acids

In an alternative embodiment of the present invention, plants, seeds, or plant parts are protected against pathogens by providing transgenic plants, seeds, or plant parts which comprise a heterologous gene encoding a DES and which produce levels of divinyl fatty acids sufficient to provide protection. In an embodiment of the present invention, transgenic plants comprise levels of divinyl ether fatty acids sufficient to provide protection. In another embodiment, transgenic plants, seeds, or plant parts which comprise a heterologous gene encoding a DES are grown, stored, or utilized under conditions which allow the plants, seeds or plant parts to produce or to contain levels of divinyl fatty acids sufficient to provide protection.

In a further embodiment of the present invention, transgenic plants, seeds, or plant parts which comprise a heterologous gene encoding a DES and which produce levels of divinyl fatty acids sufficient to provide protection may be further treated by application of divinyl ether fatty acids as described above. In an alternative embodiment, transgenic plants, seeds, or plant parts which comprise a heterologous gene encoding a DES may be further treated by application of substrates of DES, which substrates are hydroperoxy fatty acids and which application is similar to that described above for applying exogenous divinyl ether fatty acids.

In an alternative embodiment of the present invention, plants, seeds, or plant parts are protected against pathogens by providing transgenic plants, seeds, or plant parts which comprise a heterologous gene encoding a DES and which further comprise an endogenously high level of LOX activity. By "high level" it is meant that the level of LOX activity is at least about twice the average level of activity observed in a population of plants, where the population comprises either the same variety or cultivar, or the same crop, or a variety of crops; preferably, the level of LOX activity is at least about five times the average level of activity, and most preferably the level of LOX activity is at least about ten times the average level of activity. In a further embodiment of the present invention, transgenic plants, seeds, or plant parts which comprise a heterologous gene encoding DES and high endogenous levels of LOX activity and which produce levels of divinyl fatty acids sufficient to provide protection may be further treated by application of divinyl ether fatty acids as described above. In an alternative embodiment, transgenic plants, seeds, or plant parts which comprise a heterologous gene encoding DES and endogenously high levels of LOX activity may be further treated by application of fatty acid substrates of LOX, which substrates are hydroperoxy fatty acids and which application is similar to that described above for applying exogenous divinyl ether fatty acids.

In an alternative embodiment of the present invention, plants, seeds, or plant parts are protected against pathogens by providing transgenic plants, seeds, or plant parts which comprise a first heterologous gene encoding a DES and which further comprise a second heterologous gene encoding a LOX. In a further embodiment of the present invention, transgenic plants, seeds, or plant parts which comprise these two heterologous gene and which produce levels of divinyl fatty acids sufficient to provide protection may be further treated by application of divinyl ether fatty acids as described above. In an alternative embodiment, transgenic plants, seeds, or plant parts which comprise these two heterologous genes may be further treated by application of fatty acid substrates of LOX, which substrates are hydroperoxy fatty acids and which application is similar to that described above for applying exogenous divinyl ether fatty acids.

In yet another alternative embodiment of the present invention, plants, seeds, or plant parts are protected against pathogens by providing transgenic plants, seeds, or plant parts which comprise a heterologous gene encoding a fusion polypeptide comprising DES/LOX.

1. Transgenic Plants, Seeds, and Plant Parts

Plants are transformed with a heterologous gene encoding a DES or co-transformed with a first heterologous gene encoding DES and with a second heterologous gene encoding LOX or transformed with a fusion gene encoding a fusion polypeptide expressing DES and LOX activities ("a fusion DES/LOX") according to procedures well known in the art. It is contemplated that the heterologous genes are utilized to increase the level of the enzyme activities encoded by the heterologous genes.

a. Plants

The methods of the present invention are not limited to any particular plant. Indeed, a variety of plants are contemplated, including but not limited to tomato, potato, tobacco, pepper, rice, corn, barley, wheat, *Brassica, Arabidopsis*, sunflower, soybean, poplar, and pine. In some embodiments, plants with high endogenous levels of LOX activity are transformed with a heterologous gene encoding DES.

b. Vectors

The methods of the present invention contemplate the use of a heterologous gene encoding a DES, as described previously. The methods of the present invention further contemplate the use of a second heterologous gene which encodes a LOX; such polypeptides are known (Siedow, Annu Rev Plant Physiol Plant Mol Biol 42: 145-188 [1991]; Heitz et al., Plant Physiol 114: 1085-1093 [1997]; Bell E, et al., Proc Natl Acad Sci USA 92: 8675-8679 [1995]; Royo et al., J. Biol. Chem. 271: 21012-21019, [1996]). Heterologous genes encoding mutants and variants of LOX are prepared as described above for DES. Heterologous genes encoding a fusion DES/LOX is prepared as described previously.

Heterologous genes intended for expression in plants are first assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.).

In general, these vectors comprise a nucleic acid sequence encoding DES (as described above) operably linked to a promoter and other regulatory sequences (e.g., enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al., Plant Physiol 120: 979-992 [1999]); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (e.g., phaseolin, napin, oleosin, and a promoter for soybean beta conglycin (Beachy et al., EMBO J. 4: 3047-3053 [1985])). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al., Nature 313:810 [1985]; Rosenberg et al., Gene, 56:125 [1987]; Guerineau et al., Mol. Gen. Genet., 262:141 [1991]; Proudfoot, Cell, 64:671 [1991]; Sanfacon et al., Genes Dev., 5:141; Mogen et al., Plant Cell, 2:1261 [1990]; Munroe et al., Gene, 91:151 [1990]; Ballas et al., Nucleic Acids Res. 17:7891 [1989]; Joshi et al., Nucleic Acid Res., 15:9627 [1987]).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., Genes Develop. 1: 1183 [1987]). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al., Cell 39:499 [1984]; Lassner et al., Plant Molecular Biology 17:229 [1991]), a plant translational consensus sequence (Joshi, Nucleic Acids Research 15:6643 [1987]), an intron (Luehrsen and Walbot, Mol. Gen. Genet. 225:81 [1991]), and the like, operably linked to the nucleic acid sequence encoding DES.

In preparing the construct comprising the nucleic acid sequence encoding DES, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vieira, Gene 19: 259 [1982]; Bevan et al., Nature 304:184 [1983]), the bar gene which confers resistance to the herbicide phosphinothricin (White et al., Nucl Acids Res. 18:1062 [1990]; Spencer et al., Theor. Appl. Genet. 79: 625 [1990]), the hph gene which confers resistance to the antibiotic hygromycin (Blochlinger and Diggelmann, Mol. Cell. Biol. 4:2929 [1984]), and the dhfr gene, which confers resistance to methotrexate (Bourouis et al., EMBO J., 2:1099 [1983]).

In some preferred embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention is utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted DES polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention, where the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

c. Transformation Techniques

Once a nucleic acid sequence encoding DES is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., PNAS, 87:8526 [1990]; Staub and Maliga, Plant Cell, 4:39 [1992]). The presence of cloning sites between these markers allowed creation of a plastid targeting vector introduction of foreign DNA molecules (Staub and Maliga, EMBO J., 12:601 [1993]). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, PNAS, 90:913 [1993]). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway, Mol. Gen. Genet, 202:179 [1985]). In still other embodiments, the vector is transferred into the plant cell by using polyethylene glycol (Krens et al., Nature, 296:72 [1982]; Crossway et al., BioTechniques, 4:320 [1986]); fusion of protoplasts with other entities, either minicells, cells, lysosomes or other fusible lipid-surfaced bodies (Fraley et al., Proc. Natl. Acad. Sci., USA, 79:1859 [1982]); protoplast transformation (EP 0 292 435); direct gene transfer (Paszkowski et al., EMBO J., 3:2717 [1984]; Hayashimoto et al., Plant Physiol. 93:857 [1990]).

In still further embodiments, the vector may also be introduced into the plant cells by electroporation. (Fromm, et al., Pro. Natl Acad. Sci. USA 82:5824, 1985; Riggs et al., Proc. Natl. Acad. Sci. USA 83:5602 [1986]). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.). (See e.g., U.S. Pat. No. 4,945,050; and McCabe et al., Biotechnology 6:923 [1988]). See also, Weissinger et al., Annual Rev. Genet. 22:421 [1988]; Sanford et al., Particulate Science and Technology, 5:27 [1987] (onion); Svab et al., Proc. Natl. Acad. Sci. USA, 87:8526 [1990] (tobacco chloroplast); Christou et al., Plant Physiol., 87:671 [1988] (soybean); McCabe et al., Bio/Technology 6:923 [1988] (soybean); Klein et al., Proc. Natl. Acad. Sci. USA, 85:4305 [1988] (maize); Klein et al., Bio/Technology, 6:559 [1988] (maize); Klein et al., Plant Physiol., 91:4404 [1988] (maize); Fromm et al., Bio/Technology, 8:833 [1990]; and Gordon-Kamm et al., Plant Cell, 2:603 [1990] (maize); Koziel et al., Biotechnology, 11:194 [1993] (maize); Hill et al., Euphytica, 85:119 [1995] and Koziel et al., Annals of the New York Academy of Sciences 792:164 [1996]; Shimamoto et al., Nature 338: 274 [1989] (rice); Christou et al., Biotechnology, 9:957 [1991] (rice); Datta et al., Bio/Technology 8:736 [1990] (rice); European Patent Application EP 0 332 581 (orchardgrass and other Pooideae); Vasil et al., Biotechnology, 11: 1553 [1993] (wheat); Weeks et al., Plant Physiol., 102: 1077 [1993] (wheat); Wan et al., Plant Physiol. 104: 37 [1994] (barley); Jahne et al., Theor. Appl. Genet. 89:525 [1994] (barley); Knudsen and Muller, Planta, 185:330 [1991]

(barley); Umbeck et al., Bio/Technology 5: 263 [1987] (cotton); Casas et al., Proc. Natl. Acad. Sci. USA 90:11212 [1993] (sorghum); Somers et al., Bio/Technology 10:1589 [1992] (oat); Torbert et al., Plant Cell Reports, 14:635 [1995] (oat); Weeks et al., Plant Physiol., 102:1077 [1993] (wheat); Chang et al., WO 94/13822 (wheat) and Nehra et al., The Plant Journal, 5:285 [1994] (wheat).

In addition to direct transformation, in some embodiments, the vectors comprising a nucleic acid sequence encoding DES are transferred using *Agrobacterium*-mediated transformation (Hinchee et al., Biotechnology, 6:915 [1988]; Ishida et al., Nature Biotechnology 14:745 [1996]). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237: 1176 [1987]). Species which are susceptible infection by *Agrobacterium* may be transformed in vitro.

d. Regeneration

After selecting for transformed plant material which can express the heterologous gene encoding DES, whole plants are regenerated. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. III, 1986. It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

e. Generation of Transgenic Lines

Transgenic lines are established from transgenic plants by tissue culture propagation. The presence of nucleic acid sequences encoding exogenous DES or mutants or variants thereof may be transferred to related varieties by traditional plant breeding techniques.

These transgenic lines are then utilized for evaluation of pathogen resistance and other agronomic traits.

2. Evaluation of Resistance to Pathogens

Both confirmed transgenic lines and the untransformed line are first tested for response to a pathogen in replicated, controlled environment trials.

Plants are tested at a period of time appropriate to the particular type of plant following transfer from tissue culture to cm pots containing a potting medium in the greenhouse. A typical controlled environment chamber is approximately 3 $m^3$ and is enclosed with six mill clear plastic. The relative humidity in the chamber is maintained at a level appropriate to the particular type of plant, as for example above 90% by misting the atmosphere for 15 minutes every hour (6 liters of deionized water per 24-hour period) with gravity-fed humidifiers (Hermidifier Series 500) for potato. Air temperature inside the chamber is maintained at an appropriate level for the particular plant, as for example between 18° C. and 25° C. for transformed potato.

The pathogenic inoculum is verified by appropriate tests; and prepared in advance of each inoculation by procedures appropriate to the pathogen and well known in the art. Plants are inoculated by any of several known techniques, including inoculation with a hand held sprayer. Plants are evaluated at the appropriate time periods after inoculation (DAI) for the effect of the pathogen. Analysis of variance (ANOVA) is conducted by known techniques, as for example by using SAS proc glm, and transgenic lines are compared to the non-transgenic control line using Dunnett's T Test (SAS Institute, 1996).

Following controlled environment trials, all transgenic lines and the untransformed line are then field tested for at least one year in inoculated field trials.

In typical field trials, plants are grown in a randomized complete block design with four replications and five plants per plot with two feet between plots to facilitate evaluation. Pathogenic cultures are prepared appropriate to the particular pathogen, and the plants are inoculated by known techniques, as for example via a sprinkler irrigation system. Moisture can be maintained in the foliage via mist irrigation for the duration of the experiment. At appropriate times after inoculation, plots are evaluated for presence and effects of the pathogen. The area under the disease progress curve (AUDPC) is calculated for each transgenic line as described by Shaner and Finney [1977] and divided by the maximum AUDPC to convert the value to relative AUDPC (RAUDPC) for comparison across years. Statistical analyses are performed as cited above for controlled environment trials.

The present invention is not limited to the degree of pathogen resistance conferred by the presence of the heterologous gene or genes in transgenic plants. Indeed, a variety of levels of resistance are contemplated. For example, one level of resistance is complete inhibition of growth of the pathogen, such that no symptoms are observed. Another level of resistance is a decreased rate of growth of the pathogen, compared to its growth rate in a plant not comprising the heterologous gene or genes. Different levels of resistance are commercially useful. For example, a decreased pathogen growth rate which allows the plant to set seed at normal or near normal levels (i.e., at levels observed in the absence of the pathogen) is commercially acceptable. A pathogen growth rate which is sufficiently decreased to allow longer storage of harvested plant materials and/or less spoilage upon storage is also commercially acceptable.

V. Uses of Divinyl Ether Fatty Acid and Divinyl Ether Synthase

In another aspect of the invention, divinyl ether fatty acids produced in accordance with the present invention are utilized industrially (i.e., in applications and products other than for pathogen resistance in plants). Many "unusual" fatty acids are used in the production of soaps, detergents, lubricants, surfactants, coatings, paints, plasticizers, varnishers, cosmetics, and polymers. It is contemplated that, in accordance with the present invention, polyunsaturated fatty acids are treated with LOX and DES on industrial scale to generate oils that contain divinyl ether fatty acids. The divinyl ether fatty acids are envisioned to have useful properties in themselves (e.g., altered viscosity), and further to provide an ether function to make another derivative, e.g., by cleaving the hydrocarbon backbone.

In yet another aspect of the present invention, it is contemplated that divinyl ether fatty acids produced in accordance with the present invention are utilized as dietary supplements and medicinals. Thus, the double bond of the vinyl ether is an antioxidant and thus believed to be a crucial element in cellular protection. Moreover, divinyl ethers are thought to prevent hepatic ischemia, and are increasingly used as anticancer drugs.

The use of divinyl ethers as dietary supplements comprises administering an effective amount of a divinyl ether fatty acid to an individual in need thereof. The divinyl ether fatty acid may be administered as a free fatty acid, as a salt, or as an ester product as for example in a glycerolipid.

Alternatively, the divinyl fatty acid may be administered via an extract prepared from a plant. In some embodiments, the extract is obtained from a plant enriched in endogenous LOX, to which exogenous DES is added; in other embodiments, the extract is obtained from a plant in which exogenous LOX and DES is added; in yet other embodiments, the extract is obtained from a plant in which exogenous LOX, DES, and fatty acid substrates for LOX are added. In yet other embodiments, the extract is obtained from transgenic plants; such plants may be transformed with both LOX and DES, or alternatively, plants with high endogenous levels of LOX are transformed with DES alone. Any of these extracts may comprise exogenously added substrates for LOX. In all of these embodiments, divinyl ether fatty acids can be produced in the plants before extraction, or in the plant extraction during an incubation period, or both.

In yet other aspects of the present invention, it is further contemplated that the divinyl ether fatty acids are used as the platform for drug development.

In yet another aspect of the present invention, it is further contemplated that the general ability of DES (and other CYP74 P450s) to cleave carbon-carbon bonds is useful, for example in the breakdown of oils (oil spills). In yet other aspects of the present invention, it is contemplated that DES is used as an industrial catalyst, in reactions in which hydroxyl groups are converted to hydroperoxy groups and then converted to the ether moieties. The DES may be added to an in vitro synthetic system, as is described above, to which the substrates are added and from which the products are extracted. Thus, in some embodiments, the present invention provides a method of catalyzing a reaction, comprising combining a purified divinyl ether synthase and a hydroperoxy substrate under conditions effective to convert the hydroperoxy substrate to a divinyl ether product. Alternatively, the DES may be present in a cell (e.g., a bacteria or a yeast cell) or in a tissue or organ (such as culture plant tissues) and used in a fermentation system, to which the substrates are added and from which the products are extracted. Thus, in other embodiments, the present invention provides a method of catalyzing a reaction, comprising combining a transgenic organism and a hydroperoxy substrate under conditions effective to convert the hydroperoxy substrate to a divinyl ether product, wherein the transgenic organism comprises a heterologous gene encoding a divinyl ether synthase.

VI. Expression of Divinyl Ether Synthase in Transgenic Plants

It is contemplated that the nucleic acids encoding DES of the present invention may be utilized to either increase or decrease the level of DES mRNA and/or protein in transfected cells as compared to the levels in wild-type cells. Such transgenic cells have great utility, including but not limited to as a source of DES for industrial uses, as described above, and for further research into the effects of the overexpression of DES into the effects of the under expression or lack of DES.

Accordingly, in some embodiments, expression in plants by the methods described above leads to the overexpression of DES in transgenic plants, plant tissues, or plant cells. DES may be isolated as described above, and subsequently used as described above, as for example, in in vitro systems for producing divinyl ether fatty acids, or in industrial processes as a catalyst.

In other embodiments of the present invention, the DES polynucleotides are utilized to decrease the level of DES protein or mRNA in transgenic plants, plant tissues, or plant cells as compared to wild-type plants, plant tissues, or plant cells. One method of reducing DES expression utilizes expression of antisense transcripts. Antisense RNA has been used to inhibit plant target genes in a tissue-specific manner (e.g., van der Krol et al., Biotechniques 6:958-976 [1988]). Antisense inhibition has been shown using the entire cDNA sequence as well as a partial cDNA sequence (e.g., Sheehy et al., Proc. Natl. Acad. Sci. USA 85:8805-8809 [1988]; Cannon et al., Plant Mol. Biol. 15:39-47 [1990]). There is also evidence that 3' non-coding sequence fragment and 5' coding sequence fragments, containing as few as 41 base-pairs of a 1.87 kb cDNA, can play important roles in antisense inhibition (Ch'ng et al., Proc. Natl. Acad. Sci. USA 86:10006-10010 [1989]).

Accordingly, in some embodiments, the DES nucleic acids of the present invention (e.g., SEQ ID NO: 1, and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al., Nature 334:585-591 (1988).

Another method of reducing DES expression utilizes the phenomenon of cosuppression or gene silencing (See e.g., U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al., Plant Cell 2:279-289 [1990]; van der Krol et al., Plant Cell 2:291-299 [1990]; Smith et al., Mol. Gen. Genetics 224:477-481 [1990]). Accordingly, in some embodiments the nucleic acid sequences encoding DES acids (e.g., SEQ ID NOs 1, and fragments and variants thereof) are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); PCR (polymerase chain reaction); RT-PCR (reverse-transcriptase-PCR); TAIL-PCR (thermal asymmetric interlaced-PCR); LOX (lipoxygenase); AOS (allene oxide synthase); CYP74D1 and DES (DES); HPL (fatty acid hydroperoxide lyase); JA (jasmonic acid); 9-HPOD (9(S)-hydroperoxy-10(E),12(Z)-octadecadienoic acid); 9-HPOT (9(S)-hydroperoxy-10(E),12(Z),15(Z)-octadecatrienoic acid); 13-HPOD (13(S)-hydroperoxy-9(Z),11(E)-octadecadienoic acid); 13-HPOT (13(S)-hydroperoxy-9(Z),11(E),15(Z)-octadecatrienoic acid); colneleic acid (9-[1'(E),3'(Z)-nonadienyloxy]-8(E)-nonenoic acid); colnelenic acid (9-[1'(E),3"(Z),6'(Z)-nonatrienyloxy]-8(E)-nonenoic acid); CA (colneleic acid); CnA (colnelenic acid).

EXAMPLE 1

Experimental Procedures

A. Plant Materials and Growth Conditions

Tomato (*Lycopersicon esculentum* cv. Castlemart) plants were grown in Jiffy peat pots (Hummert International) in a growth chamber maintained under 17 h of light (300 (E m$^{-2}$ s$^{-1}$) at 28° C. and 7 h of dark at 18° C. Flowers and fruits were harvested from plants maintained in a greenhouse. Seeds of *L. pennellii* (LA716) and the introgression lines used for RFLP mapping were obtained from the Tomato Genetics Resource Center (Davis, Calif.).

B. cDNA Cloning and Sequencing

Basic molecular techniques were performed as described previously (Sambrook et al., Molecular Cloning: A Laboratory Manual, 2$^{nd}$ Ed., Cold Spring Harbor Laboratory, Cold Spring Harbor, N.Y. [1989]). The tomato EST clone (EST277670; GenBank No. AW034008) was obtained from the Clemson University Genomics Institute. The cDNA insert was sequenced in its entirety on both strands at the DNA sequencing facility in the MSU-DOE Plant Research Lab. The cDNA was 1631 base pairs (bp) in length, and included 18 bp upstream of the initiator AUG codon and 145 bp in the 3' untranslated region (excluding 31 poly(A) residues). Thermal asymmetric interlaced (TAIL) PCR was used to obtain additional sequence information at the 5' end of the gene as previously described (Liu & Whither, Genomics 25: 674-681 [1995]; Liu et al., Plant J. 8: 457-463 [1995]). Briefly, 20 ng of tomato genomic DNA was used as a template for an initial PCR reaction using a gene specific primer (GSP1: 5'-ACG-GAT-TTT-TCT-GAT-CAC-AAA-GCA-3') (SEQ ID NO:6) and a shorter arbitrary degenerate primer [AD3: 5'-(A/T) GTGNAG(A/T)ANCANAGA)-3] (SEQ ID NO:7). The resulting PCR product was used as a template for a second PCR reaction using the same AD3 primer and a second nested gene specific primer (GSP2: 5'-CGT-CAT-AGT-CGG-AAG-CAA-AGC-ATT-3') (SEQ ID NO:8). The PCR product obtained from this reaction was used as template for a final PCR reaction using the AD3 primer and a third nested gene specific primer (GSP3, 5'-TGT-ACC-ACC-AAG-AGT-GTC-AGT-TTT-A-3') (SEQ ID NO:9). TAIL-PCR products of approximately 1 kb were obtained from two independent reactions. DNA sequencing using the GSP3 primer revealed an in-frame stop codon (UAA) 27 nucleotides upstream of the first initiation AUG. Reverse transcription (RT)-PCR was used to exclude the possibility that the in-frame stop codon was located in an intron that was amplified by TAIL-PCR. Reverse transcription was performed with oligo(dT) primers and Superscript II reverse transcriptase (GIBCO/BRL). PCR was performed using a primer (5'-CAT-CAC-CTA-CAA- TGT-TAA-TA-3') (SEQ ID NO:10) located upstream of the in-frame stop codon and the GSP3 primer. Direct sequencing of the RT-PCR product confirmed the position of the stop codon relative to the initiator AUG codon. Database searches were performed using the BLAST program Altschul et al., J. Mol. Biol. 215: 403-410 [1990]) available at the U.S. National Center for Biotechnology. Amino acid sequence alignments were performed using the Clustal method in the Megalign program (DNAStar, Madison, Wis.).

C. Expression and Purification of Recombinant CYP74D1

A PCR-based approach was used to construct the expression vector for CYP74D1 containing an N-terminal 6×-Histidine (His)-tag (6H-CYP74D). Forward and reverse primers that amplify the cDNA were designed to contain BamHI and HindIII restriction sites, respectively. The sequence of the forward primer was 5'-CGG-GAT-CCC-TTC-CGA-TTC-GTG-AAA-TTC-CA-3' (SEQ ID NO:11) and that of reverse primer 5'-CCC-AAG-CTT-GCA-ACG-TGA-GCG-GGC-ACA-CA-3' (SEQ ID NO:12). PCR amplification of EST277670 yielded a 1.4 kb product that was subsequently cut with BamHI and HindIII and subcloned into the same sites of expression vector pQE-30 (Qiagen Corp., Santa Clarita, Calif.). The resulting construct, which replaced the first nine amino acids of CYP74D1 with the sequence MRGSHHHH-HHGS (SEQ ID NO:13), was transformed into $E.$ $coli$ host strain M15 for expression. A similar strategy was used for construction of the C-terminal His-tagged protein (CYP74D-6H). Forward and reverse primers were designed to contain NdeI and XhoI restriction sites, respectively. The sequence of the forward primer was 5'-GGA-ATT-CCA-TAT-GTC-TTC-TTA-TTC-AGA-GCT-3' (SEQ ID NO:14) and that of reverse primer 5'-CCG-CTC-GAG-TTT-ACT-TGC-TTT-AGT-TAA-TG-3' (SEQ ID NO:15). PCR amplification of EST277670 yielded a 1.45 kb product that was cut with NdeI and XhoI prior to subcloning into the same sites of the expression vector pET-23b (Novagen, Madison, Wis.). $E.$ $coli$ strain BL21(DE3) was used for expression of CYP74D-6H, which contains an additional eight amino acids (LEHHHHHH) (SEQ ID NO:16) on the C-terminus of CYP74D1.

His-tagged recombinant proteins were expressed in the appropriate host strains as follows. An overnight culture (5 ml) was inoculated into 100 ml of Terrific Broth (TB) medium supplemented with 200 g/ml ampicillin. Bacteria were grown at 37° C. in a shaker at 250 rpm until the $OD_{600}$ was 0.6-0.8. Cultures were cooled to 25° C., and IPTG and -aminole- vulinic acid were added to final concentrations 0.05 mM and 0.5 mM, respectively. Induced cultures were incubated for approximately 40 hr at 25° C., with gently shaking (130 rpm). Cells were collected by centrifugation and stored at −20° C. until further use.

D. Product Analyses

Crude extracts from $E.$ $coli$ (M15) cells expressing 6H-CYP74D were used as enzyme source. Extracts from cells expressing the pQE-30 vector were used as a mock control. Frozen cell paste was thawed, sonicated as described below, and centrifuged at 2,500×g for 10 min at 4° C. A portion of the supernatant corresponding to 10 mg protein was incubated with 300 (g of hydroperoxide substrate (9-HPOD or 9-HPOT) dissolved in 30 ml of 50 mM potassium phosphate buffer (pH 7.0). Reactions proceeded for 10 min at 25° C. and then were stopped by acidification to pH 4.0 with 1 M citrate. Products were extracted twice with diethyl ether, dried under $N_2$ gas, and taken up in 0.25 ml of methanol. Extracted compounds were methylated by treatment with ethereal diazomethane at 0° C. for 10 min, dried under $N_2$ gas, and taken up in 50 µl of hexane. Derivatized compounds (5 µl) were analyzed by GC-MS at the MSU-NIH Mass Spectrometry Facility as previously described (Howe et al., Plant Physiol. 123, 711-724 [2000]). The cis-tuns configuration of the double bonds in the divinyl ether products was not determined.

E. Purification of CYP74D-6H

Protein purification was performed at 4° C. except where noted. Bacterial cells expressing CYP74D-6H were harvested from 200 ml of culture medium, followed by resuspension in 10 ml of buffer A (50 mM sodium phosphate, 300 mM NaCl, pH 7.0). Cells were lysed using three 30 sec pulses from a probe-type sonicator (Branson Sonifier Model 450). Cell homogenates were centrifuged at 2,500×g for 10 min and the resulting supernatant was re-centrifuged at 100,000×g for 60 min. The pellet fraction containing CYP74D-6H was solubilized in 2 ml of solubilization buffer (50 mM sodium phosphate, 1.5% TritonX-100R, pH 7.0) on ice for 30 min. The suspension was centrifuged at 100,000×g for 60 min, and the supernatant was diluted to 10 ml with buffer A. Following the addition of 1 ml of TALON metal affinity resin (cobalt-based IMAC, Clontech) pre-equilibrated with buffer A, the suspension was gently agitated at 25° C. for 40 min to allow binding of CYP74D-6H. The resin was collected by centrifugation and washed three times at 25° C. with 10 ml of buffer A containing 0.1% TritonX-100R and 5 mM imidazole (pH 7.0). The resin was applied to a column (0.7×2.5 cm, BioRad) and CYP74D-6H was eluted with buffer A containing 0.1% TritonX-100R and 150 mM imidazole (pH 7.0). The reddish brown-colored fractions containing CYP74D-6H were pooled and concentrated in a Millipore Biomax centrifugal filter (10,000 MWCO) according to the manufacturer's instructions. Imidazole was removed by diluting the preparation approximately 10-fold with 50 mM sodium phosphate buffer (pH 7.0) containing 0.02% TritonX-100R and 5% glycerol, followed by concentration on a centrifugal filter as described above. Protein measurements were performed by the method of Bradford, using BSA as a standard. The relative purity of CYP74D-6H was judged by Coomassie Brilliant Blue R-250 staining of samples analyzed on SDS-polyacrylamide gels (10% polyacrylamide).

F. Biochemical Analysis of CYP74D1

The hydroperoxide-metabolizing activity of recombinant CYP74D1 was measured spectrophotometrically by monitoring the rate of decrease in $A_{234}$ that results from disruption of the conjugated diene bond of the substrate (Zimmerman & Vick, Plant Physiol. 46: 445-453 [1970]). Kinetic assays were performed at 25° C. in 1 ml of 100 mM sodium phosphate (pH 7.0) containing 30 ng of purified CYP74D-6H and varying amounts of substrate. Activity slopes obtained during the first 0.5 min of the reaction were used for calculation of kinetic parameters. Specific activity measurements were performed in a similar fashion using a substrate concentration of 50 µM. Fatty acid hydroperoxide substrates were obtained from Cayman Chemical (Ann Arbor, Mich.). Extinction coefficients provided by the manufacturer were used for calculations. Absorbance spectra were obtained using affinity purified CYP74D-6H in 1 ml of 50 mM sodium phosphate buffer (pH 7.0). Protein concentration was determined using the Bradford assay. CO treatments were performed by bubbling CO gas through the sample for 1 min, and reduction of the protein was achieved by adding a few grains of sodium dithionite.

G. Preparation of [1-$^{14}$C] 9-HPOD

[1-$^{14}$C] 9-HPOD was prepared using ripened tomato fruits as a source of 9-LOX activity, using a modification of a previously described procedure (Smith et al., Phytochemistry 45: 453-458 [1997]). Diced fruit pericarp was homogenized in 0.1 M sodium phosphate buffer (pH 7.0) containing 1 mM EDTA and 0.1% (w/v) TritonX-100R, filtered through three layers of Miracloth (Calbiochem), and centrifuged for 15 min at 10,000×g. 9-LOX activity in the supernatant was precipitated by $(NH_4)_2SO_4$ in the 30 to 60% fraction. Following centrifugation for 20 min at 15,000×g the pellet was resuspended in 0.1 M sodium phosphate buffer (pH 6.0) containing 20% (v/v) glycerol and stored at −80° C. until use. [$1$-$^{14}C$] Linoleic acid (51 Ci mol$^{-1}$) was purchased from NEN Life Science Products, Inc. (Boston, Mass.). Radiolabeled fatty acid was diluted with unlabeled linoleic acid (NuChek-Prep, Elysian, Minn.) to achieve a final specific activity of 1.9 Ci mol$^{-1}$. This preparation was converted to the ammonium salt, and then diluted with 1% TritonX-100R to achieve a final fatty acid concentration of 10 mM. One-half ml of this solution was added to 4.5 ml of an oxygen-saturated solution containing 0.1 M sodium phosphate (pH 6.0). To this substrate was added 0.5 ml of the tomato fruit LOX fraction (12 mg protein) described above. The reaction was allowed to proceed for 45 min at 0° C. in the presence of bubbling oxygen, and then stopped by acidification to pH 4.0 with 1M citrate. Lipid products were extracted with chloroform, dried under $N_2$, and dissolved in a small amount of chloroform. The mixture was fractionated by thin layer chromatography (TLC) using a high performance (HP) silica gel plate (HPTLC 60 $F_{254}$, Merck) developed with diethyl ether:hexane:formic acid (70:30:1). The major radiolabeled product, [$1$-$^{14}C$] 9-HPOD, was scraped from the TLC plate and stored in ETOH at −80° C. until use.

H. DES Activity in Plant Extracts

A modification of a previously described TLC assay (Caldelari and Farmer., Phytochemistry 47: 599-604 [1998]) was used to monitor the transformation of [$1$-$^{14}C$] 9-HPOD to [$1$-$^{14}C$] CA in cell-free extracts obtained from various tomato tissues. Briefly, extract from freshly ground tomato roots, stems, or leaves was centrifuged at 10,000×g at 4° C. for 2 min. A volume of supernatant containing 60 µg protein was immediately added to 0.4 ml of 40 mM sodium phosphate buffer (pH 7.0) containing of 0.1% TritonX-100 and 10% glycerol (v/v). Reactions were initiated by addition of 5 µg of [$1$-$^{14}C$] 9-HPOT prepared as described above. After an incubation period of 10 rain at 25° C., reactions were acidified to pH 4 and extracted with 0.4 ml of chloroform:MeOH (2:1). Lipid products obtained after evaporation of the solvent were dissolved in chloroform and separated on HP-TLC plates as described above. Labeled metabolites were visualized by autoradiography using Kodak XAR-5 film. The identity of CA among the chromatographed products was determined by GC-MS analysis of bands scraped from the TLC plate.

I. RNA and DNA Blot Analysis

RNA extraction and blot hybridization analysis of mRNA levels was performed as previously described (Howe et al., Plant Physiol. 123: 711-724 [2000]). Full-length LeDES and LeAOS (33) cDNAs were PCR-amplified from the plasmid vector (pBlueScript) using T3 and T7 primers. Tomato genomic DNA preparations and Southern blot analysis was as previously described (Howe et al., Plant Physiol. 123: 711-724 [2000]).

EXAMPLE 2

Identification and Cloning of Nucleic Acid Sequence Encoding Divinyl Ether Synthase A. Identification of a Tomato cDNA Encoding a Novel CYP74 P45

A BLAST search (Altschul et al., J. Mol. Biol. 215: 403-410 ([1990]) of the tomato EST database was conducted to search for potential novel CYP74 sequences.

A tentative consensus sequence (TC17776), constructed from multiple overlapping ESTs (Quackenbush et al., Nucleic Acids Res., 28, 141-145 [2000]) was identified that was similar to but clearly distinct from known CYP74 sequences in tomato and other plants. DNA sequencing of one EST clone (EST277670) revealed a 1,631-bp cDNA insert containing an open reading frame predicted to encode a 478 amino acid protein. TAIL- and RT-PCR experiments provided additional sequence information at the 5' end of the transcript. DNA sequencing of this region revealed an in-frame stop codon 27 bp upstream of the first AUG, indicating that the cDNA encodes a full-length protein. A BLAST search of sequences in GenBank showed that the novel CYP74 was most similar (45% identity) to a HPL from *Cucumis sativus* (GenBank AF229811) that is classified as CYP74C1. The next strongest match (approximately 42% identity) was to members of the CYP74A subfamily (AOS). The third and final significant match (approximately 30% identity) was to HPL sequences that make up the CYP74B subfamily. According to guidelines for cytochrome P450 nomenclature, the novel tomato CYP74 is classified as the first member (CYP74D1) of a new CYP74 subfamily designated CYP74D (D. Nelson, personal communication). A comparison of the deduced CYP74D1 sequence to tomato AOS (LeAOS1 and LeAOS2) and HPL (LeHPL) is shown in FIG. 3.

The sequence of CYP74D1 displayed many of the features that differentiate CYP74 enzymes from $O_2$- and NADPH-requiring P450 monooxygenases. However, some differences between CYP74D1 and other CYP74 subfamilies were noted. P450 monooxygenases have a consensus sequence of (A/G)Gx(D/E)T(T/S) (SEQ ID NO:17) within the I-helix that forms part of the oxygen-binding pocket (Chapple, C., Annu. Rev. Plant Physiol. Plant Mol. Biol. 49: 311-343 (1998]). In both bacterial and mammalian microsomal P450, the invariant threonine residue (underlined) is thought to play a critical role in the binding and activation of oxygen (Poulos, et al., J. Mol. Biol. 195: 687-700 [1987]; Williams et al., Mol. Cell. 5: 121-31. [2000]). All previously reported CYP74 sequences have an isoleucine or valine in place of the conserved threonine, and conform to the consensus sequence Ggxx(I/V) (SEQ ID NO:18). The corresponding region of CYP74D1 has the sequence AgxxAF (SEQ ID NO:19), which differs from all other CYP74 sequences in two positions (bolded residues) within this hexapeptide motif. The heme-binding domain of CYP74D1 is characteristic of other CYP74 enzymes. The CYP74 consensus sequence for residues surrounding the cysteinyl heme ligand near the C-terminus is NKQC(A/P)(G/A) K(D/N)xV (SEQ ID NO:20), and is conserved in CYP74D1. When variant positions within this consensus are considered, CYP74D1 most closely resembles CsHPL (CYP74C1) and two barley AOS (CYP74A) that utilize 9- and 13-hydroperoxides (Maucher, et al., Plant J. 21: 199-213 [2000]). The predicted amino acid sequence of CYP74D1 lacks a hydrophobic N-terminus that assists in anchoring many eukaryotic P450s to the endoplasmic reticulum (Chapple, Annu. Rev. Plant Physiol. Plant Mol. Biol. 49: 311-343 [1998]). CYP74D1 also lacks a typical N-terminal targeting sequence that directs many CYP74 proteins, including tomato AOS (Froehlich et al., Plant Physiol. In press [2000]), to the chloroplast.

B. CYP74D1 is a Divinyl Ether Synthase

To investigate the catalytic function of CYP74D1, the protein was expressed in *E. coli* with an N-terminal 6×-His tag (6H-CYP74D). Bacterial cultures expressing the construct accumulated low levels of the recombinant protein as determined by SDS-PAGE analysis of bacterial extracts. A spectrophotometric assay was used to test the extracts for their ability to metabolize fatty acid hydroperoxides. Extracts containing 6H-CYP74D, but not those derived from control cells expressing the empty vector, efficiently metabolized 9-HPOD and 9-HPOT (see Table I).

TABLE 1

Substrate specificity of CYP74D1 expressed in E. coli

| Substrate | Enzyme Source | |
|---|---|---|
| | pQE-30 | H-CYPD74D |
| | nmol/min/mg protein | |
| 9-HPOD | 22 ± 1 | 606 ± 12 |
| 13-HPOD | 29 ± 1 | 49 ± 1 |
| 9-HPOT | 15 ± 1 | 395 ± 9 |
| 13-HPOD | 22 ± 1 | 38 ± 1 |

Assays were performed at 25© in 1 ml of 100 mM sodium phosphate (pH 7.0). Each assay contained the indicated substrate at a concentration of 50 (M and crude extract (equivalent of 5 (g protein) from cells expressing either 6H-CYP74D or the empty expression vector (pQE-30). Activity was determined from the rate of decrease in $A_{234}$ of the substrate. Values represent the mean and SE of activity values determined from three enzyme preparations of each culture.

In repeated experiments using different enzyme preparations, the rate of 9-HPOD metabolism was consistently greater than that observed for 9-HPOT. Interestingly, 13-HPOD and 13-HPOT were poor substrates for 6H-CYP74D. This finding indicated that CYP74D1 is specific for the metabolism of 9-hydroperoxides, the first such example among CYP74 enzymes.

Figure 4:
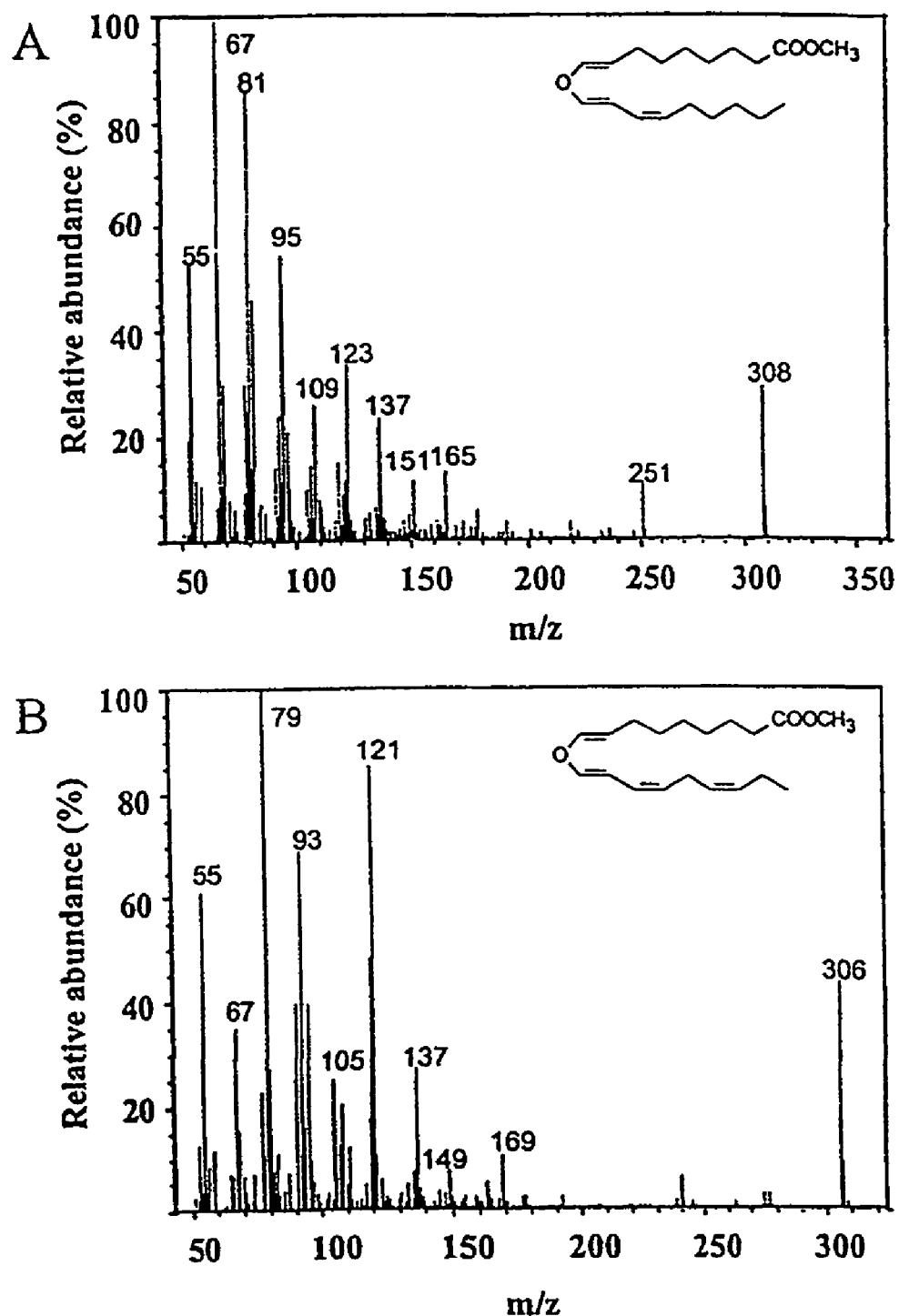
FIG. 4 shows a mass spectra of products formed by metabolism of 9-hydroperoxides by CYP74D1. (A) Extracts from *E. coli* cells expressing 6H-CYP74D were incubated with 9(S)-hydroperoxy-10(E),12(Z)-octadecadienoic acid (9(S)-HPOD). Reaction products were analyzed as methyl ester derivatives by GC-MS. The major product identified, methyl colneleic acid, is shown. (B) Same as above except that 9(S)-hydroperoxy-10(E),12(Z),15(Z)-octadecatrienoic acid) (9(S)-HPOT) was used as substrate. The identified product, methyl colnelenic acid, is shown.
Figure 5:
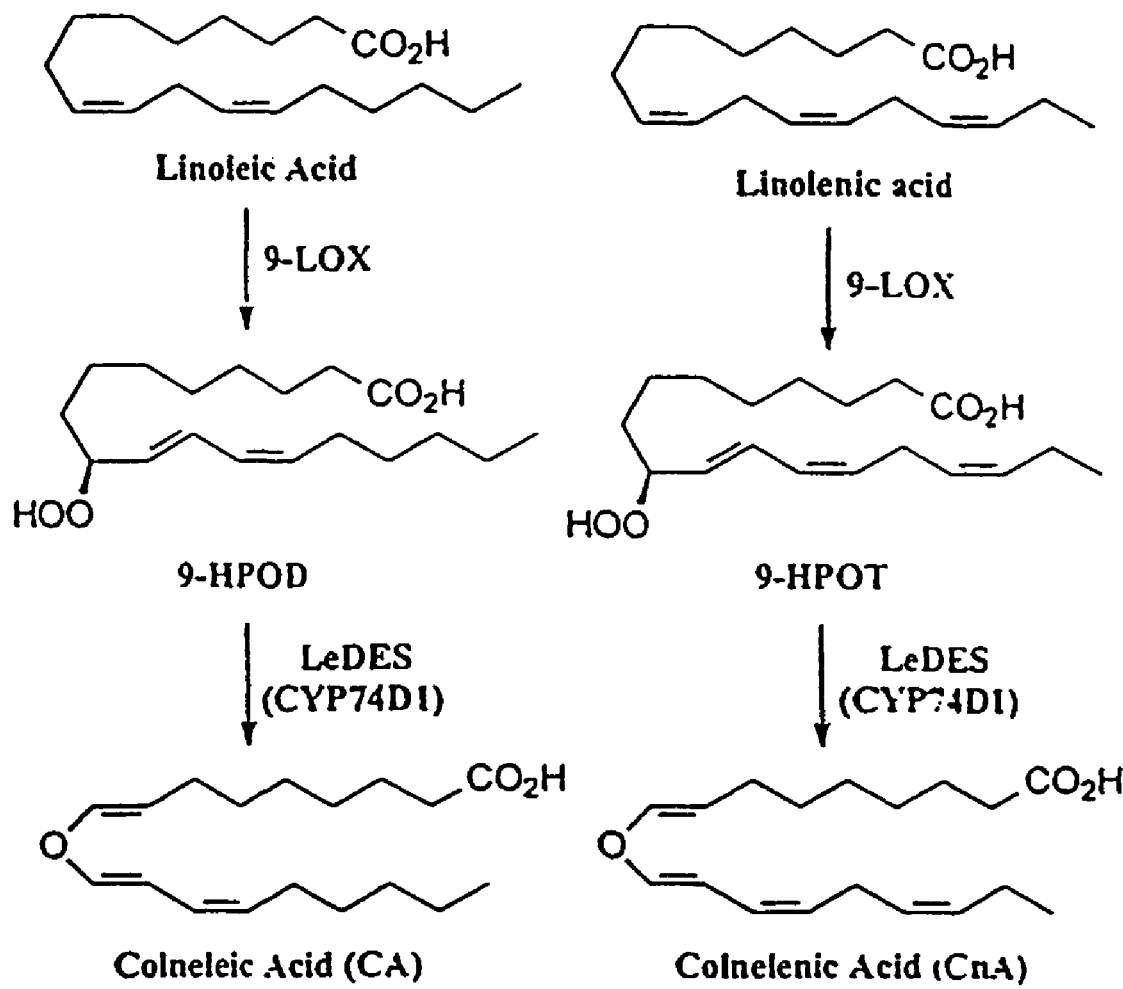
FIG. 5 shows the role of CYP74D1 in the biosynthesis of divinyl ether oxylipins. The pathways shown are those elucidated for the in vitro synthesis of colneleic acid (CA) and colnelenic acid (can) in potato tubers. The reaction step catalyzed by CYP74D1 is indicated.

Gas chromatography-mass spectrometry (GC-MS) was used to identify the methylated derivatives of metabolites produced upon incubation of 6H-CYP74D with 9-hydroperoxy fatty acids. With 9-HPOD as substrate, the product showed one major peak on GC-MS analysis that was not present in a mock control reaction. The mass spectrum recorded on this peak showed prominent ions at m/z 308 ($M^+$; 29%), 251 (10%), 165 (14%), 151 (1%), 137 (22%), 123 (33%), 109 (25%), 95 (54%), 81 (86%) and 67 (100%) (FIG. 5A). This spectrum is in agreement with published spectra for the methyl ester of colneleic acid (CA), a divinyl ether derived from 9(S)-HPOD (Gallard and Phillips, Biochem. J. 129: 743-753 [1972]; Caldelari and Farmer, Phytochemistry, 47: 599-604 [1998]; Crombie et al., J. Chem. Soc. Perkin Trans. 1: 567-575. [1991]). With 9-HPOT as substrate, the methylated product also showed one major peak on GC-MS analysis. The mass spectrum recorded on this peak showed prominent ions at m/z 306 ($M^+$; 43%), 169 (10%), 149 (8%), 137 (25%), 121 (89%), 105 (25%), 93 (68%) and 79 (100%) (FIG. 4B). This spectrum identified the compound as the methyl ester of colnelenic acid (CnA), and was in agreement with published spectra (Caldelari and Farmer, Phytochemistry, 47: 599-604 [1998]; Crombie et al., J. Chem. Soc. Perkin Trans. 1: 567-575. [1991]). These results show that CYP74D1 has DES activity that converts 9-HPOD and 9-HPOT to the divinyl ether fatty acids CA and CnA, respectively (FIG. 5). In keeping with previous nomenclature that describes the plant origin and function of CYP74 enzymes, the trivial name LeDES is assigned to the tomato gene encoding CYP74D1.

EXAMPLE 3

Characterization of Divinyl Ether Synthase Protein and Gene

Figure 6:
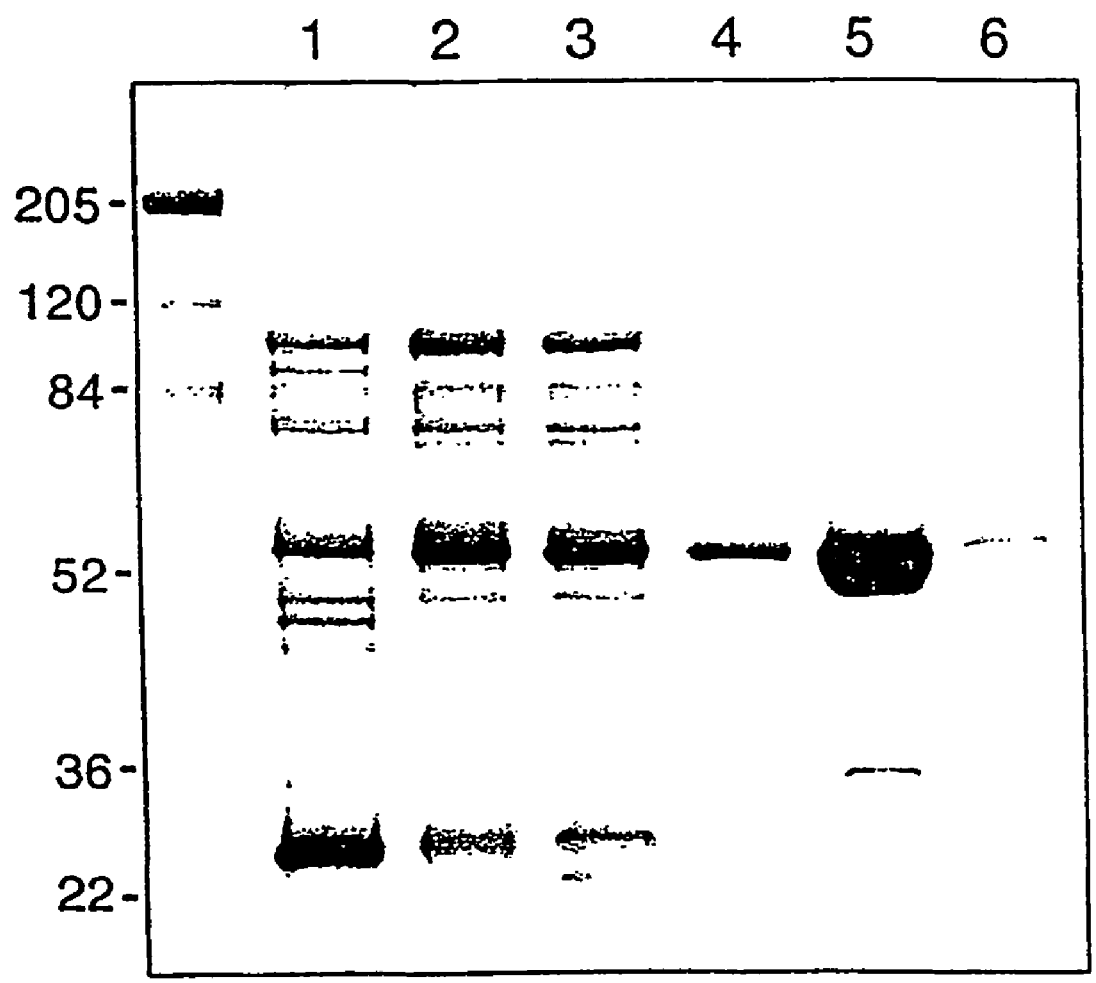
FIG. 6 shows affinity purification of CYP74D1 expressed in *E. coli*. An SDS-polyacrylamide gel stained with Coomassie Brilliant Blue R250 is shown. Crude cell extract (2,500×g supernatant) (lane 1) from cells expressing CYP74D-6H was centrifuged at 100,000×g. The pellet (lane 2) was resuspended in solubilization buffer and re-centrifuged at 100,000×g. The resulting supernatant (lane 3) was applied to a cobalt-affinity column that was subsequently eluted with 150 mM imidazole. Lanes 4-6 show the protein content of three successive fractions (1 ml each) after elution. Protein standards of the indicated molecular mass are shown on the left.

A. Purification and Biochemical Properties of the Protein
To enable purification of CYPD74D1 by affinity chromatography, this protein was initially expressed in E. coli with an N-terminal 6×-His tag, as 6H-CYPD74D1; the presence of the histidine tag was intended to improve the affinity of the protein for resins. However, attempts to purify 6H-CYP74D1 using metal-affinity chromatography were unsuccessful, due to poor binding of the protein to the resins. An alternative solution to this problem was to construct an expression vector with a 6×-His tag added to the C-terminus of the protein. This form of CYP74D1, designated CYP74D-6H, accumulated to relatively high levels in bacterial cells that were induced for expression (FIG. 6). Approximately 85% of the DES activity in the crude homogenate was recovered in the 100,000×g pellet, indicating that the protein is associated with E. coli membranes. Solubilization of membranes with TritonX-100R and subsequent cobalt-chelate chromatography allowed purification of CYP74D-6H to >95% homogeneity (FIG. 6, lanes 4-6).

The molecular weight of the purified protein as determined by SDS gel electrophoresis was in good agreement with the calculated M of 55,254. Total recovery of CYP74D-6H after the affinity purification step was approximately 1.2 mg per liter of cultured cells. The specific activity of the enzyme, with 9-HPOD as substrate, increased 750-fold during the purification procedure. The apparent $K_m$ of 9-HPOD and 9-HPOT was 67 (M and 48 (M, respectively. Assuming the total protein content of CYP74D-6H to be active, the estimated turnover rate ($k_{cat}$) of 9-HPOD was 890 $s^{-1}$, whereas that for 9-HPOT was 500 $s^{-1}$. These values are comparable to the turnover number of 13-hydroperoxides by AOS and HPL (Song and Brash, Science 252: 781-784 [1991]; Pan et al., J. Biol. Chem. 15: 8487-8494 [1995]; Tijet et al., Lipids 35: 709-20 [2000]). 13-HPOD and 13-HPOT, as well as various commercially available hydroperoxides (5-, 12-, or 15-substituted) of arachidonic acid, were metabolized at <5% of the rate observed for 9-HPOD.

Figure 7:
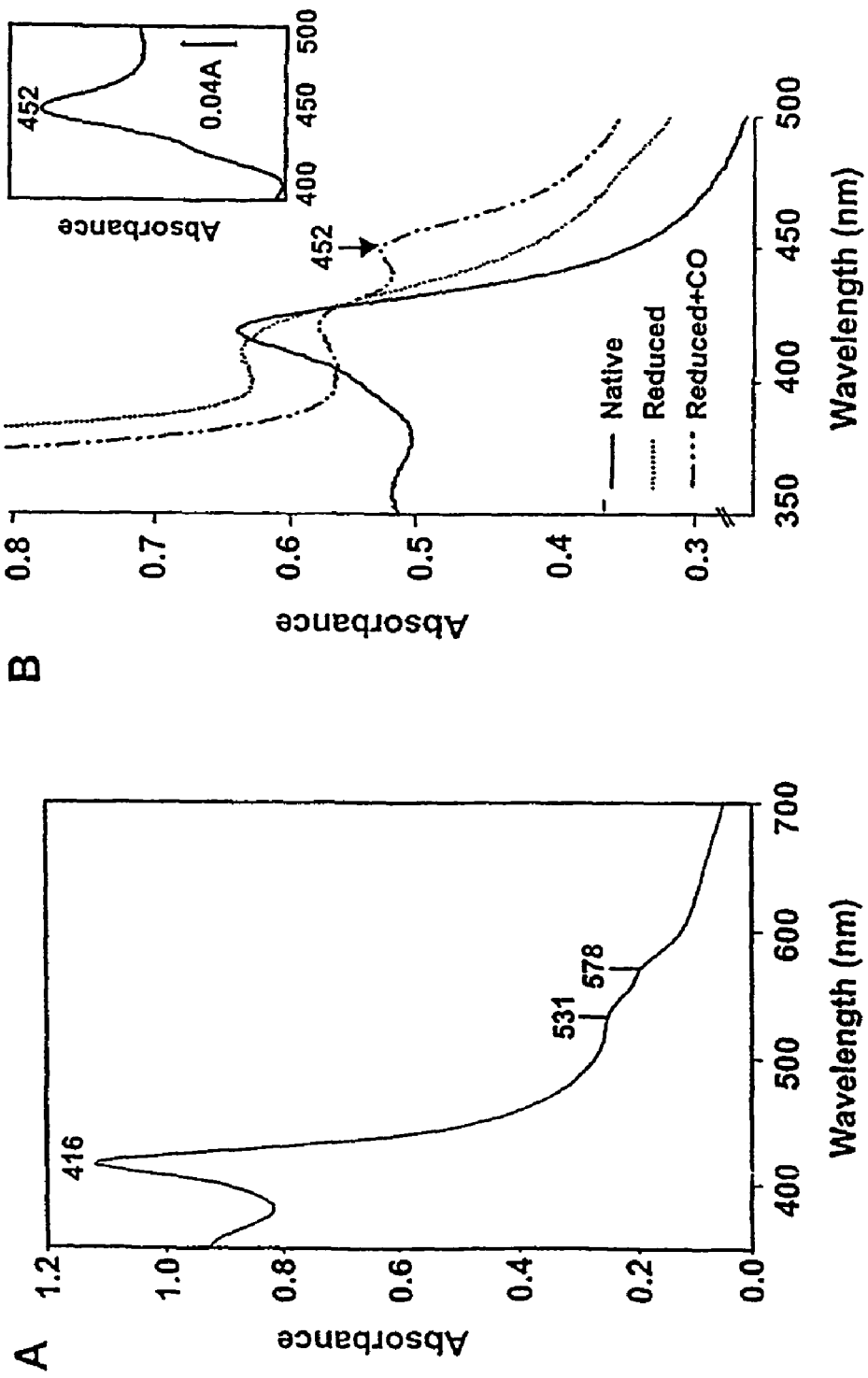
FIG. 7 shows an absorption spectra of CYP74D1. (A) UV-visible spectrum of affinity purified CYP74D-6H (280 (g). (B) Spectrum of purified CYP74D-6H (180 (g) that was: untreated (solid line); reduced with dithionite (dotted line); reduced with dithionite and bubbled with CO for 1 min (dashed line). The inset shows the difference spectrum obtained by subtraction of the reduced spectrum from the reduced, CO-treated spectrum. All spectra were recorded in 1 ml 50 mM sodium phosphate buffer, pH 7.0.

The spectral properties of purified CYP74D-6H were typical of low spin cytochrome P450. The UV-visible spectrum showed a Soret band at 416 nm and minor shoulders at 531 nm and 578 nm (FIG. 7A). Treatment of the dithionite-reduced enzyme with CO resulted in the formation of a 452 nm band, indicative of the heme-CO complex of cytochrome P450 (FIG. 7B). This peak was highlighted in a difference spectrum between the reduced CO-heme complex and resting CYP74D1 (FIG. 7B, inset). A reproducible feature of the reduced CO spectrum was the persistence of a P420 chromophore. This could reflect a weak interaction of the protein with CO (Song and Brash, Science 252: 781-784 [1991]; Lau et al., Biochemistry 32: 945-1950 [1993]), or the presence of inactive P420 form of CYP74D-6H. Incomplete conversion to the P450 form was also observed in the presence of methyl viologen, suggesting the latter possibility.

Figure 8:
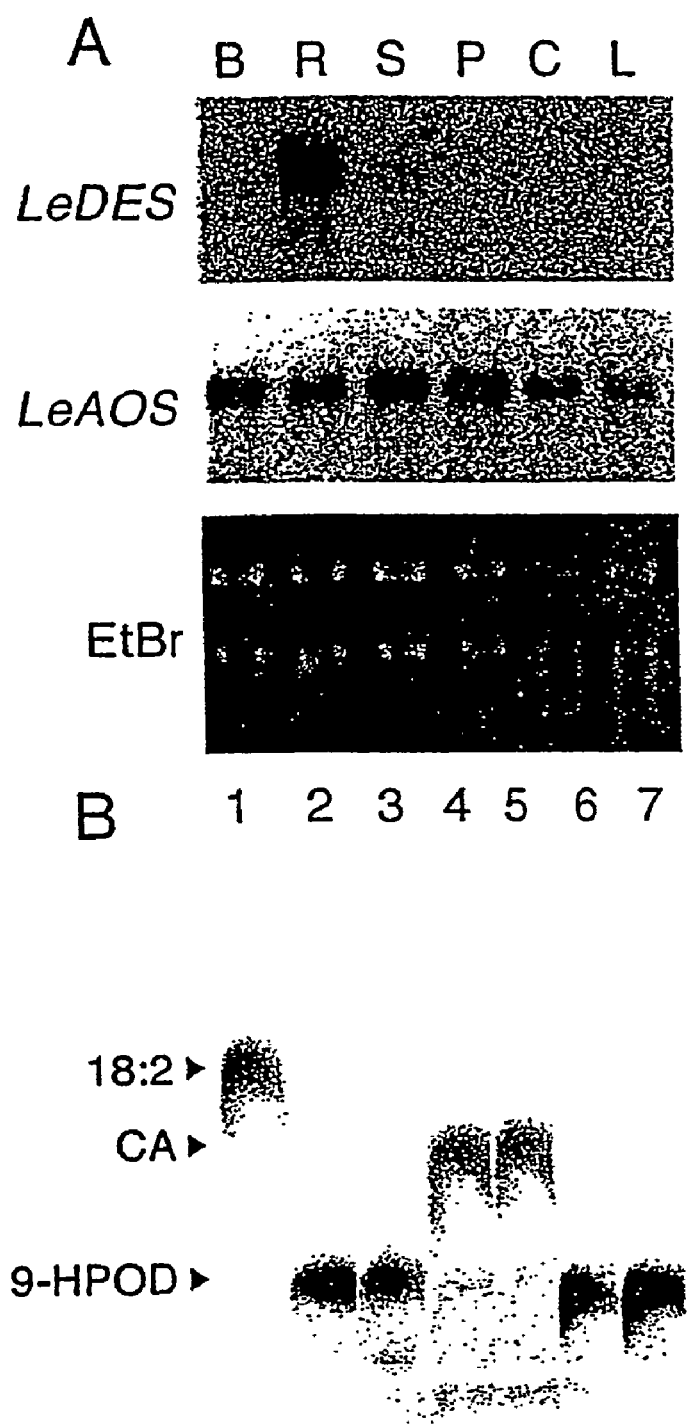
FIG. 8 shows tissue-specific expression of LeDES mRNA and DES activity. (A) Total RNA was extracted from unopened flower buds (B) of six-week-old tomato plants, and from roots (R), stems (S), petioles (P), cotyledons (C), and leaves (L) of 18-day-old plants. Five (g samples of RNA were subjected to RNA-blot analysis. Duplicate blots were hybridized to full-length LeDES and LeAOS (CYP74A2) cDNA probes. The autoradiograph of the blot is shown together with a photograph of an ethidium bromide-stained gel of the same RNA (EtBr). (B) Plant juice was expressed from roots (lane 5), stems (lane 6), and leaves (lane 7) of 18-day-old plants. An amount of juice corresponding to 60 (g protein was incubated with [1-$^{14}$C] 9-HPOD. As controls, *E. coli* extract (5 (g protein) obtained from cells expressing the pQE-30 vector (lane 3) or 6H-CYP74D (lane 4) was incubated with the substrate. Reaction products were extracted and analyzed by TLC. [1-$^{14}$C] linoleic acid and [1-$^{14}$C] 9-HPOD standards were chromatographed in lanes 1 and 2, respectively. Following development of the chromatograph (origin at bottom), labeled products were visualized by autoradiography.

B. Developmental Expression of LeDES
RNA blot analysis was used to investigate the distribution of LeDES mRNA in different organs of tomato (FIG. 8A). LeDES transcripts were most abundant in roots. A low level of LeDES mRNA was observed in stem tissue, but no accumulation was detected in flower buds, petioles, cotyledons, or leaves. This expression pattern contrasted the broad distribution of LeAOS transcripts that encode CYP74A2 (Howe, Plant Physiol. 123: 711-724 [2000]). Previously it was reported that cell-free extracts from tomato roots but not leaves support the in vitro synthesis of CA and CnA from linoleic acid and linolenic acid, respectively (Caldelari and Farmer, Phytochemistry, 47: 599-604 [1998]). The results shown in FIG. 8A suggest that tissue-specific synthesis of these compounds can be accounted for by the tissue-specific expression of DES activity. To further test this hypothesis, a radio-TLC assay was used to examine the ability of cell-free extracts from different tissues to catalyze the direct transformation of 9-HPOD to CA. The results showed that extracts from roots, but not extracts from stem or leaf tissue, catalyze efficient formation of CA from the hydroperoxide precursor (FIG. 8B, lanes 5-7). The identity of the labeled product as CA (lane 5) was confirmed by GC-MS (data not shown) and by its co-migration with a CA standard generated with recombinant 6H-CYP74D (lane 4). These findings demonstrate that control of divinyl ether biosynthesis in various tomato tissues is regulated by tissue-specific expression of LeDES.

C. LeDES Gene Copy Number and Chromosomal Location

Tomato genomic DNA was cleaved separately with four different restriction endonucleases DraI, EcoRI, HinDIII) and subjected to DNA-blot analysis using the LeDES cDNA as a probe. The results showed a single hybridizing fragment in each of the endonuclease-digested samples. The chromosomal location of the LeDES gene was mapped using a set of 50 introgression lines that harbor defined segments of *L. pennellii* DNA (Eshed and Zamir, Euphytica 79, 175-179 [1994]). Each line was screened for the presence of a DraI-generated restriction fragment length polymorphism (RFLP) that distinguishes the LeDES gene in *L. pennellii* from its ortholog in *L. esculentum*. Only one line (LA3479) displayed the *L. pennellii* RFLP pattern. The introgressed DNA present in LA3479 is located on the end of the long arm of chromosome one, and encompasses the region flanked by RFLP markers TG245 and TG259 on the tomato RFLP map (Tanksley, et al., Genetics 132: 1141-1160 [1992]). Hybridization of blots to a RFLP marker (TG369) known to map to this interval confirmed the identity of LA3479. These results show that in tomato LeDES is a single copy gene located on the distal half of the long arm of chromosome one.

EXAMPLE 4

Variants of DES

Certain embodiments of the present invention include variant forms of DES which are equivalent to SEQ ID NO:2; these embodiments include the nucleic acid sequences encoding these variants. In some embodiments, conservative mutations result in changes to the amino acid sequence which do not result in a major effect on the biological activity of the resulting polypeptide. Exemplary embodiments include some embodiments in which at least one amino acid of SEQ ID NO:2 is replaced by a structurally related amino acids, and other embodiments in which at least one amino acid of SEQ ID NO:2 is deleted or added. Some preferred examples of such amino acid changes are shown in Table 2.

TABLE 2

| Conservative amino acid changes to SEQ ID NO: 2 | |
|---|---|
| Additions | Phe 133 → Leu |
| | Asp 91 → Glu |
| | Ala 60 → Pro |
| | Asp 119 → Glu |
| | Asp 178 → Asn |

TABLE 2-continued

| Conservative amino acid changes to SEQ ID NO: 2 | |
|---|---|
| | Ile 180 → Leu |
| | Ala 249 → Phe |
| Deletions | Asp 151 |
| | Lys 219 |
| Additions | Histidine tag, amino terminal |
| | Histidine tag, carboxyl terminal |

EXAMPLE 5

Protection of Potato Plants from Pathogens

A. Generation of Divinyl Ether Synthase Transgenic Lines

A cDNA construct encoding DES from tomato was prepared as described in Example 1 and is present in a construct suitable for expression in potato plants. This construct is Clontech's pBI121 vector that contains a GUS gene driven by 35S, and a NOS termination. The vector also contains an NPTII gene for selection in *E. coli, Agrobacterium*, and plants. The GUS gene was removed and replaced with the LeDES cDNA in the "sense" orientation to produce a chimeric 35S::DES::NOS construct. A second construct was prepared as described, except that it contained LeDES cDNA in the "antisense" orientation.

Initial transgenic potato lines are generated from MSU potato breeding line MSE149, which is characterized by easy propagation and production of numerous transgenic shoots. MSU potato breeding line MSE149-is propagated by tissue culture propagated and then transformed with the DES construct via *Agrobacterium*-mediated transformation as described previously (Li et al., J. Amer. Soc. Hort. Sci. 124: 218-223 [1999]). All putative transgenic plants are tested by Southern analysis (to verify transgene insertion and copy number) as well as northern and western analyses to verify transgene expression (Li et al., J. Amer. Soc. Hort. Sci. 124: 218-223 [1999]). Transgenic lines ("MSE149-5Y:DES lines") are established from transgenic plants by tissue culture propagation, and then utilized for late blight evaluations and other agronomic trials.

Subsequent transgenic potato lines are generated from two partially late blight resistant potato cultivars/breeding lines (MSG274-3 and Libertas); these lines are also transformed with the DES construct and evaluated as described for the MSE149-5Y:DES lines.

B. Evaluation of Resistance to Late Blight

Both confirmed transgenic MSE149-5Y:DES lines and untransformed MSE149-5Y line are first tested for response to *P. infestans* in replicated, controlled environment trials.

Plants are tested 5 to 6 weeks following transfer from tissue culture to 10 cm pots containing Baccto potting medium in the greenhouse. The controlled environment chamber is approximately 3 $m^3$ and is enclosed with six mill clear plastic. The relative humidity in the chamber is maintained above 90% by misting the atmosphere for 15 minutes every hour (6 liters of deionized water per 24-hour period) with gravity-fed humidifiers (Hermidifier Series 500). Air temperature inside the chamber is maintained between 18© and 25 (C.

The *P. infestans* inoculum is the US-8 genotype/A2 mating type as determined by the gel-acetate electrophoretic technique (Goodwin et al., Plant Disease 79:1181-1185 [1995B]) and the production of oospores when grown with an isolate known to be the A1 mating type. Cultures are started ten days in advance of each inoculation. A $10^5$ sporangia $ml^{-1}$ suspension culture is used and is stored for four hours at 4 to stimulate zoospore release prior to inoculation with a hand held sprayer. Plants are evaluated at 7 and 14 days after inoculation (DAI) for percent plant area infected. Analysis of variance (ANOVA) is conducted using SAS proc glm, and transgenic MSE149-5Y:DES lines are compared to the non-transgenic control MSE149-5Y line using Dunnett's T Test (SAS Institute, 1996).

Following controlled environment trials, all transgenic MSE149-5Y:DES lines and untransformed MSE149-5Y line are then field tested for two years in inoculated field trials at the Muck Soils Research Farm (Bath, Mich.).

Plants are grown in a randomized complete block design with four replications and five plants per plot with two feet between plots to facilitate evaluation. Zoospore suspension cultures are prepared as described above and the plants are inoculated via a sprinkler irrigation system. Moisture is maintained in the foliage via mist irrigation for the duration of the experiment. Beginning at 7 days after infection (DAI), plots are evaluated for percent area infected until no further disease progress is observed. The area under the disease progress curve (AUDPC) is calculated for each transgenic line as described by Shaner and Finney [1977] and divided by the maximum AUDPC to convert the value to relative AUDPC (RAUDPC) for comparison across years. Statistical analyses are performed as cited above for controlled environment trials.

C. Resistance to Other Pathogens

Both confirmed transgenic lines and the untransformed line are first tested for response to a pathogen in replicated, controlled environment trials, and subsequently for at least one year in field trials as described previously.

D. Increased Resistance

In both the controlled environment trials and in the field trials, it is contemplated that increased resistance to *P. infestans* is observed in the transgenic MSE149-5Y:DES lines.

In both the controlled environment trials and in the field trials, it is contemplated that increased resistance to other pathogens are observed in the transgenic MSE149-5Y:DES lines.

E. Mechanism of Resistance

The levels of colneleic and colnelenic acid in various tissues of transgenic and untransformed plants are evaluated by HPLC (Weber et al., Plant Cell 11: 485-493 [1999]). Assays will be conducted at various times after pathogen inoculation of plants grown in an environmental chamber and in the field. Uninoculated plants are used as a control. Increased resistance is correlated with increased accumulation of divinyl ether fatty acids.

F. Increasing Levels of LOX Activity

In transgenic potato plants, the level of resistance to pathogens, and in particular to *P. infestans*, is correlated with the levels of both DES and LOX activity. In some plants and for some pathogens, low levels of resistance to pathogens is correlated with low levels of LOX activity even when levels of DES activity are increased over non-transgenic plants. Thus, it may be desirable to increase the level of LOX activity as well. The level of LOX activity is increased in at least two ways. In one method, plants with high levels of endogenous LOX activity are transformed with a heterologous gene for DES and the plants tested for resistance to pathogens, as described above. Such plants may be individuals selected from a population of similar plants, such as a variety or cultivar, or they may be particular varieties within a crop plant, or they may be a particular crop plant. In another method, plants are co-transformed with two heterologous genes encoding DES and LOX, or with a single heterologous gene encoding a fusion protein having both enzyme activities.

EXAMPLE 6

Protection of Tomato Plants from Pathogens

Tomato plants generally have levels of LOX activity which are greater than those of other crop plants, such as potato. Therefore, transgenic tomato plants comprising a heterologous gene for DES were prepared as described above for potato plants, using the same construct and the same protocol. These transgenic plants are examined for resistance to pathogens, also as described above. It is contemplated that the transgenic tomato plants show increased resistance to plant pathogens, especially those susceptible to divinyl ether fatty acids.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. An isolated nucleic acid sequence encoding a divinyl ether synthase that
    a) catalyzes conversion of hydroperoxide fatty acids to divinyl ether fatty acids that contain an oxygen within the hydrocarbon chain,
    b) has greater than 90% sequence identity to amino acid sequence SEQ ID NO: 2, and
    c) comprises motif sequence AGxxAF (SEQ ID NO:19).

2. The nucleic acid sequence according to claim 1, wherein said divinyl ether synthase has greater than 95% sequence identity to amino acid sequence SEQ ID NO: 2.

3. The isolated nucleic acid sequence of claim 1, wherein said divinyl ether synthase competes for binding to a dihydroperoxide fatty acid substrate with a protein encoded by a nucleic acid sequence comprising SEQ ID NO: 1.

4. An isolated antisense sequence corresponding to a nucleic acid sequence encoding a divinyl ether synthase of claim 1.

5. The nucleic acid sequence according to claim 1 operably linked to a heterologous promoter.

6. A vector comprising a nucleic acid sequence according to claim 1.

7. A vector comprising a nucleic acid sequence according to claim 5.

8. The nucleic acid sequence according to claim 1, wherein said divinyl ether synthase has greater than 98% sequence identity to amino acid sequence SEQ ID NO: 2.

9. An isolated nucleic acid sequence encoding a divinyl ether synthase that catalyzes conversion of hydroperoxide fatty acids to divinyl ether fatty acids that contain an oxygen within the hydrocarbon chain, wherein said isolated nucleic acid sequence hybridizes under conditions of low stringency to a nucleic sequence comprising SEQ ID NO: 1, and wherein said nucleic acid is identified by a method comprising
    a) hybridization to SEQ ID NO: 1 at 42° C. in a solution comprising 43.8 g/l NaCl, 6.9 g/l $NaH_2PO_4.H_2O$, 1.85 g/l EDTA, 0.1% SDS, 1 g/l Ficoll, 5 g/l bovine serum albumin Fraction V, and 100 μg/ml denatured salmon sperm DNA at pH 7.4, and
    b) washing in a solution comprising 43.8 g/l NaCl, 6.9 g/l $NaH_2PO_4.H_2O$, 1.85 g/l EDTA, and 0.1% SDS at 42° C. at pH 7.4.

10. The method of claim 9, wherein said divinyl ether synthase comprises motif sequence AGxxAF (SEQ ID NO:19).

11. An isolated nucleic acid sequence encoding a divinyl ether synthase that catalyzes conversion of hydroperoxide fatty acids to divinyl ether fatty acids that contain an oxygen within the hydrocarbon chain, wherein said isolated nucleic acid sequence hybridizes under conditions of high stringency to a nucleic sequence comprising SEQ ID NO: 1, and wherein said nucleic acid is identified by a method comprising
    a) hybridization to SEQ ID NO: 1 at 43.8 g/l NaCl, 6.9 g/l $NaH_2PO_4.H_2O$, 1.85 g/l EDTA, 0.5% SDS, 1 g/l Ficoll, 5 g/l bovine serum albumin Fraction V, and 100 μg/ml denatured salmon sperm DNA at pH 7.4, and
    b) washing in a solution comprising 0.876 g/l NaCl, 0.138 g/l $NaH_2PO_4.H_2O$, 0.037 g/l EDTA, and 1.0% SDS at 42° C. at pH 7.4.

12. The method of claim 11, wherein said divinyl ether synthase comprises motif sequence AGxxAF (SEQ ID NO:19).

* * * * *

SEQUENCE LISTING

```
<160> NUMBER OF SEQ ID NOS: 20

<210> SEQ ID NO 1
<211> LENGTH: 1679
<212> TYPE: DNA
<213> ORGANISM: Lycopersicon esculentum
<220> FEATURE:
<221> NAME/KEY: CDS
<222> LOCATION: (67)..(1500)

<400> SEQUENCE: 1
acatcaccta caatgttaat aaaactcact aaaccaaaat aacaacacca aaacttgtta      60 agaaaa atg tct tct tat tca gag cta tca aat ctt ccg att cgt gaa        108
```

-continued

|  |  |  |  |  |  |  |  |  |  |  |  |  |
|---|---|---|---|---|---|---|---|---|---|---|---|---|
| Met | Ser | Ser | Tyr | Ser | Glu | Leu | Ser | Asn | Leu | Pro | Ile | Arg | Glu |
| 1 |  |  |  | 5 |  |  |  |  | 10 |  |  |  |  |

```
att cca ggg gac tat ggt ttc cct ata att agc gcg att aaa gat cga      156
Ile Pro Gly Asp Tyr Gly Phe Pro Ile Ile Ser Ala Ile Lys Asp Arg
15              20                  25                  30 tac gat tat ttc tat aac caa ggt gaa gat gct tgg ttc cat aac aaa      204
Tyr Asp Tyr Phe Tyr Asn Gln Gly Glu Asp Ala Trp Phe His Asn Lys
                    35                  40                  45 gct gaa aaa tac aaa tct act gtt gtc aaa atc aac atg gca cca ggt      252
Ala Glu Lys Tyr Lys Ser Thr Val Val Lys Ile Asn Met Ala Pro Gly
                50                  55                  60 cca ttc aca tct aat gac tac aaa ttg gta gcc ttt tta gat gcc aat      300
Pro Phe Thr Ser Asn Asp Tyr Lys Leu Val Ala Phe Leu Asp Ala Asn
            65                  70                  75 agc ttt gtt tgc atg ttt gat aat tcc ctc att gat aaa act gac act      348
Ser Phe Val Cys Met Phe Asp Asn Ser Leu Ile Asp Lys Thr Asp Thr
        80                  85                  90 ctt ggt ggt aca ttt aag cct ggt aaa gaa tac tac ggt ggt tat cgt      396
Leu Gly Gly Thr Phe Lys Pro Gly Lys Glu Tyr Tyr Gly Gly Tyr Arg
95                 100                 105                 110 ccc gtc gcg ttt atc gat acc aaa gat cca aac cac gca gca tta aaa      444
Pro Val Ala Phe Ile Asp Thr Lys Asp Pro Asn His Ala Ala Leu Lys
                    115                 120                 125 ggc tac att tta tca tca ttc gca aag cga cat aac tta ttc att cct      492
Gly Tyr Ile Leu Ser Ser Phe Ala Lys Arg His Asn Leu Phe Ile Pro
                130                 135                 140 ctg ttc aga aac acg tta tcc gat cat ctt ttt aat aat ctc gaa aaa      540
Leu Phe Arg Asn Thr Leu Ser Asp His Leu Phe Asn Asn Leu Glu Lys
            145                 150                 155 cag gtt act gaa cag ggg aaa gca gat ttc aat gct ttg ctt ccg act      588
Gln Val Thr Glu Gln Gly Lys Ala Asp Phe Asn Ala Leu Leu Pro Thr
        160                 165                 170 atg acg ttt gat ttc att ttt cgt ttg ctt tgt gat cag aaa aat ccg      636
Met Thr Phe Asp Phe Ile Phe Arg Leu Leu Cys Asp Gln Lys Asn Pro
175                 180                 185                 190 tct gat aca gtt ctt ggc gct caa gga cca gaa cat cta cgt aaa tgg      684
Ser Asp Thr Val Leu Gly Ala Gln Gly Pro Glu His Leu Arg Lys Trp
                    195                 200                 205 ctt ttc cca cag cta att ccg tcc ttg agc gcc aag aaa ctt cct aac      732
Leu Phe Pro Gln Leu Ile Pro Ser Leu Ser Ala Lys Lys Leu Pro Asn
                210                 215                 220 atc ata gaa gat atg ctc ttc cat aat ttt tta ata cca ttt ggt ttt      780
Ile Ile Glu Asp Met Leu Phe His Asn Phe Leu Ile Pro Phe Gly Phe
            225                 230                 235 ata aag agt gat tac aac aaa ctt gtt gat gca ttt agc aag tct gct      828
Ile Lys Ser Asp Tyr Asn Lys Leu Val Asp Ala Phe Ser Lys Ser Ala
        240                 245                 250 gtg tcc atg ttg gat gaa gca gaa aaa ctt gga atc aaa aga gaa gaa      876
Val Ser Met Leu Asp Glu Ala Glu Lys Leu Gly Ile Lys Arg Glu Glu
255                 260                 265                 270 gct gta caa aac att ctt ttt ctc gtg ggg atc aat atg ttt gcg ggg      924
Ala Val Gln Asn Ile Leu Phe Leu Val Gly Ile Asn Met Phe Ala Gly
                    275                 280                 285 ctg aac gcc ttt ttc cct cat cta ttc agg ttt gtg ggc gaa gca ggg      972
Leu Asn Ala Phe Phe Pro His Leu Phe Arg Phe Val Gly Glu Ala Gly
                290                 295                 300 gct agt cta cac aca caa ctt gct aaa gaa atc agg agt gtt att aaa     1020
Ala Ser Leu His Thr Gln Leu Ala Lys Glu Ile Arg Ser Val Ile Lys
            305                 310                 315 gaa gaa ggt ggt gca atc aca tta tca gcg att aac aaa atg agt ttg     1068
```

```
Glu Glu Gly Gly Ala Ile Thr Leu Ser Ala Ile Asn Lys Met Ser Leu
    320                 325                 330 gtc aaa tcg gta gtg tac gag aca ttg aga ctt cgc cca cca gta cca        1116
Val Lys Ser Val Val Tyr Glu Thr Leu Arg Leu Arg Pro Pro Val Pro
335                 340                 345                 350 tta cag tat ggt aag gcg aag aaa gag ttc atg gtt caa agc cac gat        1164
Leu Gln Tyr Gly Lys Ala Lys Lys Glu Phe Met Val Gln Ser His Asp
                355                 360                 365 gca tct tac aag atc aat aaa gga caa ttc gta gtt gga tat cag ccc        1212
Ala Ser Tyr Lys Ile Asn Lys Gly Gln Phe Val Val Gly Tyr Gln Pro
            370                 375                 380 atg gct agt agg gac cct aag att ttc gca aac ccg gat gag ttt gta        1260
Met Ala Ser Arg Asp Pro Lys Ile Phe Ala Asn Pro Asp Glu Phe Val
        385                 390                 395 cct gat agg ttc atg aat gat ggt gag aaa atg ctg aaa cat gtc cta        1308
Pro Asp Arg Phe Met Asn Asp Gly Glu Lys Met Leu Lys His Val Leu
    400                 405                 410 tgg tct aat gga agg gaa aca gag agt cca gca cca gat aac aag caa        1356
Trp Ser Asn Gly Arg Glu Thr Glu Ser Pro Ala Pro Asp Asn Lys Gln
415                 420                 425                 430 tgt cca ggc aaa gat ttg gtg cac cta ttg ggt agg tta ata ttg gtt        1404
Cys Pro Gly Lys Asp Leu Val His Leu Leu Gly Arg Leu Ile Leu Val
                435                 440                 445 gaa ttt ttc atc aga tac gat aca ttc acc ctg gaa att aca cct cta        1452
Glu Phe Phe Ile Arg Tyr Asp Thr Phe Thr Leu Glu Ile Thr Pro Leu
            450                 455                 460 ttt cgt gca cca aat gtt gcg ttc aac aca tta act aaa gca agt aaa        1500
Phe Arg Ala Pro Asn Val Ala Phe Asn Thr Leu Thr Lys Ala Ser Lys
        465                 470                 475 tagtttgtta tgtgatcaaa ctgtgtgtgc ccgctcacgt tgcatattct cttattgatt      1560
attttatttt tttggttgta tttatttagt ttttgttgta aatcttcttt atgattcaaa      1620
tgaataaacg ttgattctag atcggatcaa aaaaaaaaaa aaaaaaaaaa aaaaaaaa        1679

<210> SEQ ID NO 2
<211> LENGTH: 478
<212> TYPE: PRT
<213> ORGANISM: Lycopersicon esculentum

<400> SEQUENCE: 2

Met Ser Ser Tyr Ser Glu Leu Ser Asn Leu Pro Ile Arg Glu Ile Pro
1               5                   10                  15

Gly Asp Tyr Gly Phe Pro Ile Ile Ser Ala Ile Lys Asp Arg Tyr Asp
            20                  25                  30

Tyr Phe Tyr Asn Gln Gly Glu Asp Ala Trp Phe His Asn Lys Ala Glu
        35                  40                  45

Lys Tyr Lys Ser Thr Val Val Lys Ile Asn Met Ala Pro Gly Pro Phe
    50                  55                  60

Thr Ser Asn Asp Tyr Lys Leu Val Ala Phe Leu Asp Ala Asn Ser Phe
65                  70                  75                  80

Val Cys Met Phe Asp Asn Ser Leu Ile Asp Lys Thr Asp Thr Leu Gly
                85                  90                  95

Gly Thr Phe Lys Pro Gly Lys Glu Tyr Tyr Gly Gly Tyr Arg Pro Val
            100                 105                 110

Ala Phe Ile Asp Thr Lys Asp Pro Asn His Ala Ala Leu Lys Gly Tyr
        115                 120                 125

Ile Leu Ser Ser Phe Ala Lys Arg His Asn Leu Phe Ile Pro Leu Phe
    130                 135                 140
```

```
Arg Asn Thr Leu Ser Asp His Leu Phe Asn Asn Leu Glu Lys Gln Val
145                 150                 155                 160

Thr Glu Gln Gly Lys Ala Asp Phe Asn Ala Leu Leu Pro Thr Met Thr
                165                 170                 175

Phe Asp Phe Ile Phe Arg Leu Leu Cys Asp Gln Lys Asn Pro Ser Asp
            180                 185                 190

Thr Val Leu Gly Ala Gln Gly Pro Glu His Leu Arg Lys Trp Leu Phe
        195                 200                 205

Pro Gln Leu Ile Pro Ser Leu Ser Ala Lys Lys Leu Pro Asn Ile Ile
    210                 215                 220

Glu Asp Met Leu Phe His Asn Phe Leu Ile Pro Phe Gly Phe Ile Lys
225                 230                 235                 240

Ser Asp Tyr Asn Lys Leu Val Asp Ala Phe Ser Lys Ser Ala Val Ser
                245                 250                 255

Met Leu Asp Glu Ala Glu Lys Leu Gly Ile Lys Arg Glu Glu Ala Val
            260                 265                 270

Gln Asn Ile Leu Phe Leu Val Gly Ile Asn Met Phe Ala Gly Leu Asn
        275                 280                 285

Ala Phe Phe Pro His Leu Phe Arg Phe Val Gly Glu Ala Gly Ala Ser
    290                 295                 300

Leu His Thr Gln Leu Ala Lys Glu Ile Arg Ser Val Ile Lys Glu Glu
305                 310                 315                 320

Gly Gly Ala Ile Thr Leu Ser Ala Ile Asn Lys Met Ser Leu Val Lys
                325                 330                 335

Ser Val Val Tyr Glu Thr Leu Arg Leu Arg Pro Pro Val Pro Leu Gln
            340                 345                 350

Tyr Gly Lys Ala Lys Lys Glu Phe Met Val Gln Ser His Asp Ala Ser
        355                 360                 365

Tyr Lys Ile Asn Lys Gly Gln Phe Val Val Gly Tyr Gln Pro Met Ala
    370                 375                 380

Ser Arg Asp Pro Lys Ile Phe Ala Asn Pro Asp Glu Phe Val Pro Asp
385                 390                 395                 400

Arg Phe Met Asn Asp Gly Glu Lys Met Leu Lys His Val Leu Trp Ser
                405                 410                 415

Asn Gly Arg Glu Thr Glu Ser Pro Ala Pro Asp Asn Lys Gln Cys Pro
            420                 425                 430

Gly Lys Asp Leu Val His Leu Leu Gly Arg Leu Ile Leu Val Glu Phe
        435                 440                 445

Phe Ile Arg Tyr Asp Thr Phe Thr Leu Glu Ile Thr Pro Leu Phe Arg
    450                 455                 460

Ala Pro Asn Val Ala Phe Asn Thr Leu Thr Lys Ala Ser Lys
465                 470                 475

<210> SEQ ID NO 3
<211> LENGTH: 534
<212> TYPE: PRT
<213> ORGANISM: Lycopersicon esculentum

<400> SEQUENCE: 3

Met Ala Ser Thr Ser Leu Ser Leu Pro Ser Leu Lys Leu Gln Phe Pro
1               5                   10                  15

Ser His Thr Ser Ser Ser Ser Arg Lys Asn Ser Ser Ser Tyr Arg Val
                20                  25                  30

Ser Ile Arg Pro Ile Gln Ala Ser Val Ser Glu Ile Pro Pro Tyr Ile
            35                  40                  45
```

```
Ser Ser Pro Ser Gln Ser Pro Ser Ser Ser Ser Pro Val Lys
    50              55                  60

Gln Ala Lys Leu Pro Ala Gln Lys Val Pro Gly Asp Tyr Ala Leu Pro
65              70                  75                  80

Leu Val Gly Pro Trp Lys Asp Arg Leu Asp Tyr Phe Tyr Asn Gln Gly
                85                  90                  95

Lys Asn Glu Phe Phe Lys Ser Arg Ile Gln Lys His Gln Ser Thr Val
            100                 105                 110

Phe Arg Thr Asn Met Pro Pro Gly Pro Phe Ile Ser Phe Asn Pro Asn
        115                 120                 125

Val Val Val Leu Leu Asp Gly Lys Ser Phe Pro Val Leu Phe Asp Val
    130                 135                 140

Ser Lys Val Glu Lys Lys Asp Leu Phe Thr Gly Thr Phe Met Pro Ser
145                 150                 155                 160

Thr Asp Leu Thr Gly Gly Tyr Arg Val Leu Ser Tyr Leu Asp Pro Ser
                165                 170                 175

Glu Pro Asn His Ala Lys Leu Lys Lys Leu Met Phe Tyr Leu Leu Ser
            180                 185                 190

Ser Arg Arg Asn Glu Val Ile Pro Glu Phe His Asn Ser Tyr Ser Glu
        195                 200                 205

Leu Phe Glu Thr Leu Glu Asn Glu Leu Ser Thr Lys Gly Lys Ala Gly
    210                 215                 220

Leu Asn Ala Ala Asn Asp Gln Ala Ala Val Asn Phe Leu Ala Arg Ser
225                 230                 235                 240

Leu Tyr Gly Ile Asn Pro Gln Asp Thr Glu Leu Gly Thr Asp Gly Pro
                245                 250                 255

Lys Leu Ile Gly Lys Trp Val Leu Phe Gln Leu His Pro Leu Leu Ile
            260                 265                 270

Leu Gly Leu Pro Lys Val Leu Glu Asp Leu Val Met His Thr Phe Arg
        275                 280                 285

Leu Pro Pro Ala Leu Val Lys Lys Asp Tyr Gln Arg Leu Tyr Asn Phe
    290                 295                 300

Phe Tyr Glu Asn Ser Thr Ser Val Leu Asp Glu Ala Glu Lys Ile Gly
305                 310                 315                 320

Ile Ser Arg Glu Glu Ala Cys His Asn Leu Leu Phe Ala Thr Cys Phe
                325                 330                 335

Asn Ser Phe Gly Gly Ile Lys Ile Phe Phe Pro Asn Met Leu Lys Trp
            340                 345                 350

Ile Gly Arg Ala Gly Ala Lys Leu His Ser Gln Leu Ala Gln Glu Ile
        355                 360                 365

Arg Ser Val Ile Ser Ser Asn Ser Gly Lys Val Thr Met Ala Ala Met
    370                 375                 380

Glu Lys Met Pro Leu Met Lys Ser Val Val Tyr Glu Ser Leu Arg Ile
385                 390                 395                 400

Glu Pro Pro Val Ala Ser Gln Tyr Gly Arg Ala Lys His Asp Met Val
                405                 410                 415

Ile Glu Ser His Asp Ala Ser Phe Glu Ile Lys Glu Gly Glu Leu Leu
            420                 425                 430

Tyr Gly Tyr Gln Pro Phe Ala Thr Lys Asp Pro Lys Ile Phe Asp Arg
        435                 440                 445

Ser Glu Glu Phe Val Ala Asp Arg Phe Lys Gly Glu Gly Glu Lys
    450                 455                 460

Leu Leu Lys His Val Leu Trp Ser Asn Gly Ser Glu Thr Glu Asn Ala
465                 470                 475                 480
```

```
Ser Ile Asn Asn Lys Gln Cys Ala Gly Lys Asp Phe Val Leu Val
            485                 490                 495

Ser Arg Leu Leu Leu Val Glu Leu Phe Leu Arg Tyr Asp Ser Phe Glu
        500                 505                 510

Ile Glu Val Gly Ala Ser Pro Leu Gly Ala Ala Ile Thr Leu Thr Ser
            515                 520                 525

Leu Arg Arg Ala Ser Phe
        530

<210> SEQ ID NO 4
<211> LENGTH: 510
<212> TYPE: PRT
<213> ORGANISM: Lycopersicon esculentum

<400> SEQUENCE: 4

Met Ala Leu Thr Leu Ser Phe Ser Leu Pro Leu Pro Ser Leu His Gln
1               5                   10                  15

Lys Ile Pro Ser Lys Tyr Ser Thr Phe Arg Pro Ile Ile Val Ser Leu
            20                  25                  30

Ser Asp Lys Ser Thr Ile Glu Ile Thr Gln Pro Ile Lys Leu Ser Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asn Asp Phe Phe Glu
65                  70                  75                  80

Ser Arg Ile Ala Lys Tyr Lys Ser Thr Ile Phe Arg Thr Asn Met Pro
                85                  90                  95

Pro Gly Pro Phe Ile Thr Ser Asn Pro Lys Val Ile Val Leu Leu Asp
            100                 105                 110

Gly Lys Ser Phe Pro Val Leu Phe Asp Ala Ser Lys Val Glu Lys Lys
        115                 120                 125

Asp Leu Phe Thr Gly Thr Phe Val Pro Ser Thr Glu Leu Thr Gly Gly
    130                 135                 140

Tyr Arg Ile Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Glu Phe His Glu Thr Tyr Thr Glu Leu Phe Glu Thr Leu Asp
            180                 185                 190

Lys Glu Met Glu Glu Lys Gly Thr Val Gly Phe Asn Ser Gly Ser Asp
        195                 200                 205

Gln Ala Ala Phe Asn Phe Leu Ala Arg Ser Leu Phe Gly Val Asn Pro
    210                 215                 220

Val Glu Thr Lys Leu Gly Thr Asp Gly Pro Ala Leu Ile Gly Lys Trp
225                 230                 235                 240

Ile Leu Leu Gln Leu His Pro Val Ile Thr Leu Gly Leu Pro Lys Phe
                245                 250                 255

Leu Asp Asp Val Leu Leu His Thr Phe Arg Leu Pro Pro Ile Leu Val
            260                 265                 270

Lys Lys Asp Tyr Gln Arg Leu Tyr Asp Phe Phe Tyr Thr Asn Ser Ala
        275                 280                 285

Asn Leu Phe Ile Glu Ala Glu Lys Leu Gly Ile Ser Lys Asp Glu Ala
    290                 295                 300

Cys His Asn Leu Leu Phe Ala Thr Cys Phe Asn Ser Phe Gly Gly Met
305                 310                 315                 320
```

```
Lys Ile Phe Phe Pro Asn Met Leu Lys Ser Ile Ala Lys Ala Gly Val
                325                 330                 335

Glu Ile His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Ile Leu Phe Gly Tyr Gln Pro Phe
                405                 410                 415

Ala Thr Lys Asp Pro Lys Ile Phe Asp Arg Pro Gly Glu Phe Val Ala
            420                 425                 430

Asp Arg Phe Val Gly Glu Glu Gly Lys Leu Leu Lys His Val Leu
        435                 440                 445

Trp Ser Asn Gly Pro Glu Thr Glu Ser Pro Thr Val Gly Asn Lys Gln
450                 455                 460

Cys Ala Gly Lys Asp Phe Val Val Met Val Ser Arg Leu Phe Val Thr
465                 470                 475                 480

Glu Phe Phe Leu Arg Tyr Gly Thr Leu Asn Val Asp Val Gly Thr Ser
                485                 490                 495

Ala Leu Gly Ser Ser Ile Thr Ile Thr Ser Leu Lys Lys Ala
            500                 505                 510

<210> SEQ ID NO 5
<211> LENGTH: 476
<212> TYPE: PRT
<213> ORGANISM: Lycopersicon esculentum

<400> SEQUENCE: 5

Met Asn Ser Ala Pro Leu Ser Thr Pro Ala Pro Val Thr Leu Pro Val
1               5                   10                  15

Arg Ser Ile Pro Gly Ser Tyr Gly Leu Pro Leu Val Gly Pro Ile Ala
            20                  25                  30

Asp Arg Leu Asp Tyr Phe Trp Phe Gln Lys Pro Glu Asn Phe Phe Thr
        35                  40                  45

Lys Arg Met Glu Lys His Lys Ser Thr Val Phe Arg Thr Asn Val Pro
    50                  55                  60

Pro Cys Phe Pro Phe Phe Gly Ser Val Asn Pro Asn Val Val Ala Val
65                  70                  75                  80

Leu Asp Val Lys Ser Phe Ser His Leu Phe Asp Met Glu Ile Val Glu
                85                  90                  95

Lys Ala Asn Val Leu Val Gly Asp Phe Met Pro Ser Val Val Tyr Thr
            100                 105                 110

Gly Asp Met Arg Val Cys Ala Tyr Leu Asp Thr Ser Glu Pro Lys His
        115                 120                 125

Ala Gln Ile Lys Asn Phe Ser Gln Asp Ile Leu Lys Arg Gly Ser Lys
    130                 135                 140

Thr Trp Val Pro Thr Leu Leu Lys Glu Leu Asp Thr Met Phe Thr Thr
145                 150                 155                 160

Phe Glu Ala Asp Leu Ser Lys Ser Asn Thr Ala Ser Leu Leu Pro Ala
                165                 170                 175

Leu Gln Lys Phe Leu Phe Asn Phe Phe Ser Leu Thr Ile Leu Gly Ala
            180                 185                 190
```

-continued

Asp Ser Ser Val Ser Pro Glu Ile Ala Asn Ser Gly Tyr Ile Phe Leu
        195                 200                 205

Asp Ser Trp Leu Ala Ile Gln Leu Ala Pro Thr Val Ser Ile Gly Val
        210                 215                 220

Leu Gln Pro Leu Glu Glu Ile Leu Val His Ser Phe Ala Tyr Pro Phe
225                 230                 235                 240

Phe Leu Val Lys Gly Asn Tyr Glu Lys Leu Val Gln Phe Val Lys Asn
            245                 250                 255

Glu Ala Lys Glu Val Leu Ser Arg Ala Gln Thr Glu Phe Gln Leu Thr
        260                 265                 270

Glu Gln Glu Ala Ile His Asn Leu Leu Phe Ile Leu Gly Phe Asn Ala
        275                 280                 285

Phe Gly Gly Phe Ser Ile Phe Leu Pro Thr Leu Leu Gly Asn Leu Gly
        290                 295                 300

Asp Glu Lys Asn Ala Asp Met Gln Glu Lys Leu Arg Lys Glu Val Arg
305                 310                 315                 320

Asp Lys Val Gly Val Asn Pro Glu Asn Leu Ser Phe Glu Ser Val Lys
            325                 330                 335

Glu Met Glu Leu Val Gln Ser Phe Val Tyr Glu Thr Leu Arg Leu Ser
        340                 345                 350

Pro Pro Val Pro Ser Gln Tyr Ala Arg Ala Arg Lys Asp Phe Lys Leu
        355                 360                 365

Ser Ser His Asp Ser Val Tyr Glu Ile Lys Lys Gly Glu Leu Leu Cys
        370                 375                 380

Gly Tyr Gln Pro Leu Val Met Lys Asp Pro Lys Val Phe Asp Glu Pro
385                 390                 395                 400

Glu Lys Phe Val Leu Glu Arg Phe Thr Lys Lys Gly Lys Glu Leu
            405                 410                 415

Leu Asn Tyr Leu Phe Trp Ser Asn Gly Pro Gln Thr Gly Arg Pro Thr
        420                 425                 430

Glu Ser Asn Lys Gln Cys Ala Ala Lys Asp Met Val Thr Leu Thr Ala
        435                 440                 445

Ser Leu Ile Val Ala Tyr Ile Phe Gln Lys Tyr Asp Ser Val Ser Phe
        450                 455                 460

Ser Ser Gly Ser Leu Thr Ser Val Lys Lys Ala Ser
465                 470                 475

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
acggattttt ctgatcacaa agca                                          24

<210> SEQ ID NO 7
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The nucleotide at this position can be Adenine
      or Thymine.
<220> FEATURE:

```
<221> NAME/KEY: misc_feature
<222> LOCATION: (5)..(5)
<223> OTHER INFORMATION: The nucleotide at this position can be any
      amino acid.
<220> FEATURE:
<221> NAME/KEY: misc_feature
<222> LOCATION: (8)..(8)
<223> OTHER INFORMATION: The nucleotide at this position can be Adenine
      or Thymine.
<220> FEATURE:
<221> NAME/KEY: misc_feature
<222> LOCATION: (10)..(10)
<223> OTHER INFORMATION: The nucleotide at this position can be any
      amino acid.
<220> FEATURE:
<221> NAME/KEY: misc_feature
<222> LOCATION: (13)..(13)
<223> OTHER INFORMATION: The nucleotide at this position can be any
      amino acid.

<400> SEQUENCE: 7
ngtgnagnan canaga                                                       16

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
cgtcatagtc ggaagcaaag catt                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
tgtaccacca agagtgtcag tttt                                              24

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
catcacctac aatgttaata                                                   20

<210> SEQ ID NO 11
<211> LENGTH: 29
<212> TYPE: DNA
<213> ORGANISM: Artificial Sequence
<220> FEATURE:
<223> OTHER INFORMATION: Synthetic

<400> SEQUENCE: 11
cgggatccct tccgattcgt gaaattcca                                         29

<210> SEQ ID NO 12
<211> LENGTH: 29
<212> TYPE: DNA
<213> ORGANISM: Artificial Sequence
<220> FEATURE:
<223> OTHER INFORMATION: Synthetic
```

-continued

```
<400> SEQUENCE: 12
cccaagcttg caacgtgagc gggcacaca                                          29

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Met Arg Gly Ser His His His His His His Gly Ser
1               5                   10

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
ggaattccat atgtcttctt attcagagct                                         30

<210> SEQ ID NO 15
<211> LENGTH: 29
<212> TYPE: DNA
<213> ORGANISM: Artificial Sequence
<220> FEATURE:
<223> OTHER INFORMATION: Synthetic

<400> SEQUENCE: 15
ccgctcgagt ttacttgctt tagttaatg                                          29

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Leu Glu His His His His His His
1               5

<210> SEQ ID NO 17
<211> LENGTH: 6
<212> TYPE: PRT
<213> ORGANISM: Lycopersicon esculentum
<220> FEATURE:
<221> NAME/KEY: SITE
<222> LOCATION: (1)..(1)
<223> OTHER INFORMATION: The amino acid at this position can be Alanine
      or Glycine.
<220> FEATURE:
<221> NAME/KEY: SITE
<222> LOCATION: (3)..(3)
<223> OTHER INFORMATION: The amino acid at this position can be any
      amino acid.
<220> FEATURE:
<221> NAME/KEY: SITE
<222> LOCATION: (4)..(4)
<223> OTHER INFORMATION: The amino acid at this position can be Aspartic
      acid or Glutamic acid
<220> FEATURE:
<221> NAME/KEY: SITE
<222> LOCATION: (6)..(6)
<223> OTHER INFORMATION: The amino acid at this position can be
      Threonine or Serine.
```

```
<400> SEQUENCE: 17

Xaa Gly Xaa Xaa Thr Xaa
1               5

<210> SEQ ID NO 18
<211> LENGTH: 6
<212> TYPE: PRT
<213> ORGANISM: Lycopersicon esculentum
<220> FEATURE:
<221> NAME/KEY: SITE
<222> LOCATION: (3)..(4)
<223> OTHER INFORMATION: The amino acid at these positions can be any
      amino acid.
<220> FEATURE:
<221> NAME/KEY: SITE
<222> LOCATION: (5)..(5)
<223> OTHER INFORMATION: The amino acid at these positions can be
      Isoleucine or Valine.
<220> FEATURE:
<221> NAME/KEY: SITE
<222> LOCATION: (6)..(6)
<223> OTHER INFORMATION: The amino acid at these positions can be
      Leucine or Phenylalanine.

<400> SEQUENCE: 18

Gly Gly Xaa Xaa Xaa Xaa
1               5

<210> SEQ ID NO 19
<211> LENGTH: 6
<212> TYPE: PRT
<213> ORGANISM: Lycopersicon esculentum
<220> FEATURE:
<221> NAME/KEY: SITE
<222> LOCATION: (3)..(4)
<223> OTHER INFORMATION: The amino acid at these positions can be any
      amino acid.

<400> SEQUENCE: 19

Ala Gly Xaa Xaa Ala Phe
1               5

<210> SEQ ID NO 20
<211> LENGTH: 10
<212> TYPE: PRT
<213> ORGANISM: Lycopersicon esculentum
<220> FEATURE:
<221> NAME/KEY: SITE
<222> LOCATION: (5)..(5)
<223> OTHER INFORMATION: The amino acid at this position can be Alanine
      or Proline.
<220> FEATURE:
<221> NAME/KEY: SITE
<222> LOCATION: (6)..(6)
<223> OTHER INFORMATION: The amino acid at this position can be Glycine
      or Alanine.
<220> FEATURE:
<221> NAME/KEY: SITE
<222> LOCATION: (8)..(8)
<223> OTHER INFORMATION: The amino acid at this position can be Aspartic
      acid or Asparagine.
<220> FEATURE:
<221> NAME/KEY: SITE
<222> LOCATION: (9)..(9)
<223> OTHER INFORMATION: The amino acid at this position can be any
      amino acid.

<400> SEQUENCE: 20

Asn Lys Gln Cys Xaa Xaa Lys Xaa Xaa Val
1               5                   10
```